(12) United States Patent
Branch et al.

(10) Patent No.: US 6,465,485 B1
(45) Date of Patent: Oct. 15, 2002

(54) TETRAHYDROISOQUINOLINE DERIVATIVES AS MODULATORS OF DOPAMINE $D_3$ RECEPTORS

(75) Inventors: Clive Leslie Branch, Dorking; Christopher Norbert Johnson, Saffron Walden; Geoffrey Stemp, Bishops Stortford, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/656,379

(22) Filed: Sep. 6, 2000

Related U.S. Application Data

(63) Continuation of application No. 09/423,163, filed as application No. PCT/EP98/02583 on Apr. 27, 1998, now abandoned.

(30) Foreign Application Priority Data

May 3, 1997 (GB) .............................................. 9708976
Nov. 4, 1997 (GB) .............................................. 9723294

(51) Int. Cl.[7] ........................ C07D 217/04; A61K 31/47
(52) U.S. Cl. ........................................ 514/307; 546/146
(58) Field of Search ........................... 546/146; 514/307

(56) References Cited

U.S. PATENT DOCUMENTS 5,891,877 A    4/1999    Brocchini et al. ........ 514/235.8

FOREIGN PATENT DOCUMENTS

| WO | WO 95/21832 | 8/1995 |
|----|-------------|--------|
| WO | WO 97/11070 | 3/1997 |
| WO | WO 98/49145 | 11/1998 |
| WO | WO 98/50363 | 11/1998 |

*Primary Examiner*—Zinna Northington Davis
(74) *Attorney, Agent, or Firm*—Nora Stein-Fernandez; Stephen A. Venetianer; Charles M. Kinzig

(57) ABSTRACT

Compounds of formula (I):

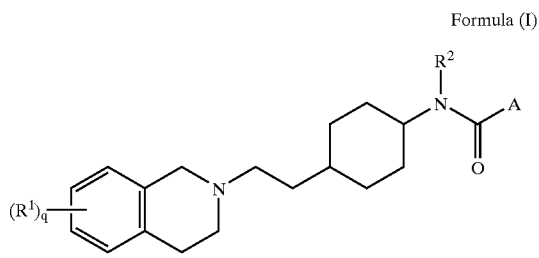

Formula (I)

and their salts having affinity for dopamine receptors, in particular the $D_3$ receptor, and thus potential in the treatment of conditions wherein modulation of the $D_3$ receptor is beneficial, e.g., as antipsychotic agents.

26 Claims, No Drawings

TETRAHYDROISOQUINOLINE DERIVATIVES AS MODULATORS OF DOPAMINE D₃ RECEPTORS

This is a continuation of application Ser. No. 09/423,163, filed Nov. 2, 1999; now abandoned which is a 371 of International Application No. PCT/EP97/02583, filed Apr. 27, 1998, which claims priority from GB Application Nos. 9708976.7 filed May 3, 1997 and 9723294.6, filed Nov. 4, 1997.

The present invention relates to novel tetrahydroisoquinoline derivatives, processes for their preparation, pharmaceutical compositions containing them and their use in therapy, as modulators of dopamine $D_3$ receptors, in particular as antipsychotic agents.

U.S. Pat. No. 5,294,621 describes tetrahydropyridine derivatives of the formula:

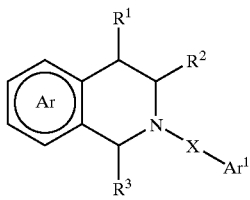

wherein

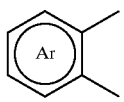

is an optionally substituted thienyl or optionally substituted phenyl ring $R^1$, $R^2$ and $R^3$ are each inter alia hydrogen; X is inter alia $(CH_2)mNR^7CO$; m is 2–4; and $Ar^1$ is an optionally substituted heterocyclic ring or an optionally substituted phenyl ring. The compounds are said to be useful as anti-arrhythmic agents.

EPA 431,580 describes compounds of formula

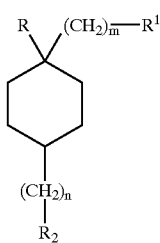

wherein R is $OR^3$, $NR^4R^5$, or $N(OR^4)R^5$, $R^4$ and $R^5$ are inter alia hydrogen, lower alkyl, aroyl or heteroaroyl; m is zero, 1 or 2; $R^1$ is hydrogen, aryl or various heteroaryl groups; n is zero or 1–4; and $R^2$ is:

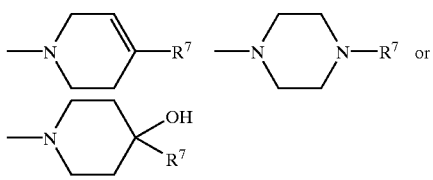

The compounds are said to be dopaminergic agents useful as antipsychotics, antihypertensives and also of use in the treatment of hyperprolactinaemia-related conditions and several central nervous system disorders.

WO 95/10513 describes benzothiophene derivatives and related compounds as estrogen agonists.

We have now found a class of tetrahydroisoquinoline derivatives which have affinity for dopamine receptors, in particular the $D_3$ receptor, and thus potential in the treatment of conditions wherein modulation of the $D_3$ receptor is beneficial eg as antipsychotic agents.

In a first aspect the present invention provides compounds of formula (I):

Formula (I)

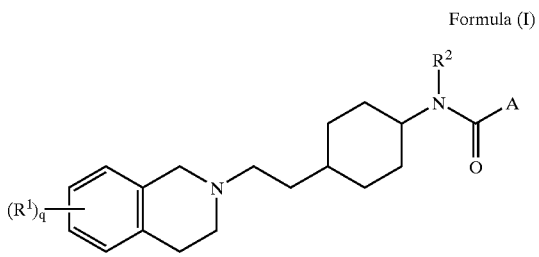

wherein:

$R^1$ represents a substituent selected from: a hydrogen or halogen atom; a hydroxy, cyano, nitro, trifluoromethyl, trifluoromethoxy, trifluoromethanesulfonyloxy, pentafluoroethyl, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulfonyl, $C_{1-4}$alkylsulfonyloxy, $C_{1-4}$alkylsulfonyl$C_{1-4}$alkyl, arylsulfonyl, arylsulfonyloxy, arylsulfonyl$C_{1-4}$alkyl, $C_{1-4}$alkylsulfonamido, $C_{1-4}$alkylamido, $C_{1-4}$alkylsulfonamido$C_{1-4}$alkyl, $C_{1-4}$alkylamido$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^3$—Z, wherein $Ar^3$ represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

q is 1 or 2;

A represents a group of the formula (a), (b) or (c):

(a)

(b)

(c)

wherein

Ar represents an optionally substituted phenyl ring or an optionally substituted 5- or 6-membered aromatic heterocyclic ring; or an optionally substituted bicyclic ring system;

$Ar^1$ and $Ar^2$ each independently represent an optionally substituted phenyl ring or an optionally substituted 5- or 6-membered aromatic heterocyclic ring; and Y represents a bond, —NHCO—, —CONH—, —CH$_2$—, or (CH$_2$)$_m$Y$^1$(CH$_2$)$_n$—, wherein Y$^1$ represents O, S, SO$_2$, or CO and m and n each represent zero or 1 such that the sum of m+n is zero or 1; providing that when A represents a group of formula (a), any substituent present in Ar ortho to the carboxamide moiety is necessarily a hydrogen or a methoxy group;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-butyl, and the like.

Examples of compounds of formula (I) include those in which Ar is a bicyclic aromatic or heteroaromatic ring system and in which R$^1$ is other than pentafluoroethyl.

When R$^1$ represents an arylC$_{1-4}$alkoxy, arylsulfonyl, arylsulfonyloxy, arylsulfonylC$_{1-4}$alkyl, arylsulfonamido, arylcarboxamido, arylsulfonamidoC$_{1-4}$alkyl, arylcarboxamidoC$_{1-4}$alkyl, aroyl, aroylC$_{1-4}$alkyl, or arylC$_{1-4}$alkanoyl group, the aryl moiety may be selected from an optionally substituted phenyl ring or an optionally substituted 5- or 6-membered heterocyclic ring. In the group R$^1$ an aryl moiety may be optionally substituted by one or more substituents selected from hydrogen, halogen, amino, cyano, C$_{1-4}$alkyl, C$_{1-4}$alkylamino, C$_{1-4}$dialkylamino, C$_{1-4}$alkylamido, C$_{1-4}$alkanoyl, or R$^5$R$^6$NCO where each of R$^5$ and R$^6$ independently represents a hydrogen atom or C$_{1-4}$alkyl group.

A halogen atom present in the compounds of formula (I) may be fluorine, chlorine, bromine or iodine.

When q is 2, the substituents R$^1$ may be the same or different.

An optionally substituted 5- or 6-membered heterocyclic aromatic ring, as defined for any of the groups Ar, Ar$^1$, Ar$^2$ or Ar$^3$ may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl.

Examples of bicyclic, for example bicyclic aromatic or heteroaromatic, ring systems for Ar include naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl, isoquinolinyl, pyrazolo[1,5-a]pyrimidyl, pyrrolo[3,2-b]pyridyl, pyrrolo[3,2-c]pyridyl, thieno[3,2-b]thiophenyl, 1,2-dihydro-2-oxo-quinolinyl, 2,3-dihydro-3-oxo-4H-benzoxazinyl, 1,2-dihydro-2-oxo-3H-indolyl.

The rings Ar, Ar$^1$, or Ar$^2$ may each independently be optionally substituted by one or more substituents selected from: a hydrogen or halogen atom, or a hydroxy, oxo, cyano, nitro, C$_{1-4}$alkyl, C$_{1-4}$alkoxy, C$_{1-4}$alkylenedioxy, C$_{1-4}$alkanoyl, C$_{1-4}$alkylsulfonyl, C$_{1-4}$alkylsulfinyl, C$_{1-4}$alkylthio, R$^7$SO$_2$NR$^8$)—, R$^7$R$^8$NSO$_2$—, R$^7$R$^8$N—, R$^7$R$^8$NCO—, or R$^7$CON(R$^8$)— group wherein each of R$^7$ and R$^8$ independently represents a hydrogen atom or a C$_{1-4}$alkyl group, or R$^7$R$^8$ together form a C$_{3-6}$ alkylene chain.

Alternatively, Ar and Ar$^2$ may be optionally substituted by one or more 5- or 6-membered heterocyclic rings, as defined above, optionally substituted by a C$_{1-2}$ alkyl or R$^7$R$^8$N— group; wherein R$^7$ and R$^8$ are as defined above.

In the rings Ar and Ar$^2$ substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulfuric, nitric or phosphoric acid; and organic acids eg. succinic, maleic, acetic, fumaric, citric, tartaric, benzoic, p-toluenesulfonic, methanesulfonic or naphthalenesulfonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

The compounds of formula (I) can exist in the form of cis- and trans-isomers with respect to the configuration at the cyclohexyl ring. When A represents a group (c) the compounds may also exist as geometric isomers around the double bond. The present invention includes within its scope all such isomers, including mixtures. Preferably the compounds of the invention are in the trans configuration with respect to the cyclohexyl ring. For compounds of formula (I) where A represents a group (c), trans geometry of the double bond is preferred.

In compounds of formula (I), it is preferred that R$^1$ represents a substituent selected from: a halogen atom, methyl, cyano, trifluoromethyl, pentafluoroethyl, or trifluoromethoxy group. A cyano group, for example in the 6- or 7-position of the tetrahydroisoquinoline ring, is especially preferred. Preferably q is 1. R$^2$ is preferably a hydrogen atom.

The group A is preferably a group of formula (a) or (c). With regard to (a), preferred examples of Ar include optionally substituted indolyl, pyrazolo[1,5-a]pyrimidyl, cinnolinyl, quinolinyl, benzo[b]furanyl or pyrrolopyridyl. With regard to (c), preferred examples are optionally substituted phenyl groups.

It is also preferred that the rings Ar, Ar$^1$, or Ar$^2$ are each independently optionally substituted by one or more substituents selected from: a hydrogen or halogen atom, cyano, methoxy, methylenedioxy, acetyl, acetylamino, methylsulfonyl, methylsulfonyloxy, methylaminosulfonyl, methylsulfonylamino, or methylaminocarbonyl group.

Certain of the substituted heteroaromatic ring systems included in compounds of formula (I) may exist in one or more tautomeric forms. The present invention includes within its scope all such tautomeric forms, including mixtures.

Particular compounds according to the invention include those specifically exemplified and named hereinafter. Preferred compounds according to the present invention include the first-mentioned compounds in each of Examples 1–33, the compound of Example 19, namely trans-6-cyano-2-(2-(1-(4(4quinolinyl)-carboxamido)cyclohexyl)ethyl)-1,2,3,4-tetrahydroisoquinoline, being especially preferred. These compounds may be in the form of their free base or physiologically acceptable salts thereof, particularly the monohydrochloride or monomesylate salts.

The present invention also provides a process for preparing compounds of formula (I) which process comprises:

(a) reacting a compound of formula (II):

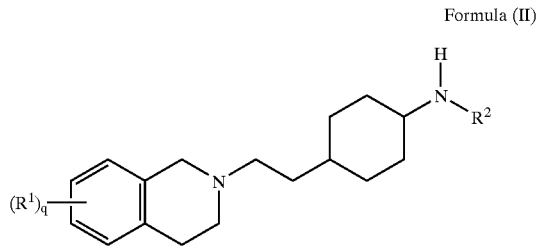

Formula (II)

wherein R¹, R² and q are as hereinbefore defined, with a compound of formula (III):

A—COX  Formula (III)

wherein A is as hereinbefore defined and X is a halogen atom or the residue of an activated ester, (b) to prepare a compound of formula (I) by reacting a compound of formula (II) with a compound A—Br, or A—I, or A—OSO$_2$CF$_3$ in the presence of carbon monoxide and a catalyst such as trans-bis-triphenylphosphinepalladium(II)bromide;

(c) to prepare a compound of formula (I) wherein R¹ is Ar³—Z and Z is a bond, reacting a compound of formula (IV):

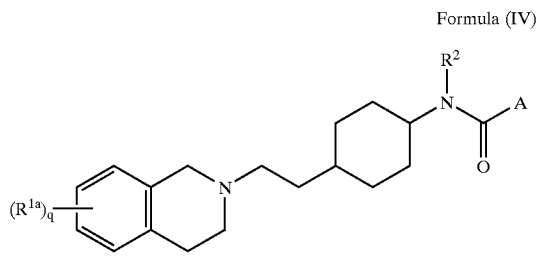

Formula (IV)

wherein R² and A are as hereinbefore defined and one R1a represents a group W wherein W is a halogen atom or a trifluoromethylsulfonyloxy group, or W is a group M selected from a boron derivative e.g. a boronic acid function B(OH)$_2$ or a metal function such as trialkylstannyl e.g. SnBu$_3$, zinc halide or magnesium halide, and when q is 2 the other R$^{1a}$ is R¹; with a compound Ar³—W¹, wherein W¹ is a halogen atom or a trifluoromethylsulfonyloxy group when W is a group M or W¹ is a group M when W is a halogen atom or a trifluoromethylsulfonyloxy group;

(d) to prepare a compound of formula (I) wherein R¹ is Ar³—Z and Z is O or S, reacting a compound of formula (V):

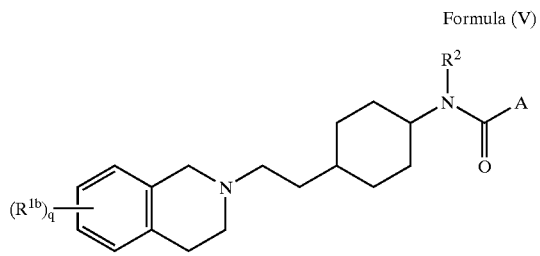

Formula (V)

wherein R² and A are as hereinbefore defined and one R$^{1b}$ represents a group ZH and when q is 2 the other R$^{1b}$ represents R¹; with a reagent serving to introduce the group Ar³;

(e) to prepare a compound of formula (I) where Y is a bond, reaction of a compound of formula (VI):

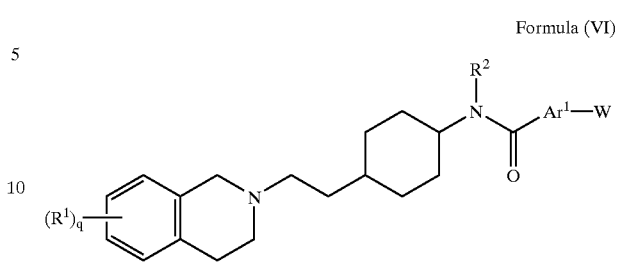

Formula (VI)

wherein R¹, R², Ar, W and q are as hereinbefore defined, with a compound Ar²—W¹, wherein W¹ is a halogen atom or a trifluoromethylsulfonyloxy group when W is a group M, or W¹ is a group M when W is a halogen atom or a trifluoromethylsulfonyloxy group.

(f) interconversion of one compound of formula (I) to a different compound of formula (I) e.g. (i) alkylation of a compound (I) wherein R² represents hydrogen, (ii) conversion of one R¹ from alkoxy (e.g.methoxy) to hydroxy, or (iii) conversion of R¹ from hydroxy to sulfonyloxy, eg alkylsulfonyloxy or trifluoromethanesulfonyloxy; (iv) conversion of a compound wherein Y represents S to a compound wherein Y is SO$_2$ or (v) conversion of Y from CO to CH$_2$;

(g) separation of cis- and trans-isomers of compounds of formula (I) by conventional methods, e.g. chromatography or crystallisation; and optionally thereafter forming a salt of formula (I).

Process (a) may be effected using conventional methods for the formation of an amide bond. When X is the residue of an activated ester this may be formed with e.g. a carbodiimide such as 1-ethyl-3-(3-dimethylaminopropyl) carbodiimide. The reaction may be carried out in a solvent such as dichloromethane.

Reaction of a compound of formula (IV) with Ar³W¹, according to process (c) or a compound of formula (VI) with Ar²—W¹ according to process (e) may be effected in the presence of a transition metal eg palladium catalyst such as bis-triphenylphosphinepalladium dichloride or tetrakis-triphenylphosphinepalladium (0). When M represents a boronic acid function such as B(OH)$_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulfonyloxy group such as trifluoromethylsulfonyloxy; and W¹ is preferably a goup M, such as trialkylstannyl or B(OH)$_2$.

In process (d) the reagent serving to introduce the group Ar³ is preferably a compound of formula Ar³—Hal, wherein Hal is a halogen atom. The reaction may be effected in the presence of a base, such as potassium carbonate, in a solvent such as dimethylformamide.

Interconversion reactions according to process (f) may be effected using methods well known in the art.

Compounds of formula (II) may be prepared by conversion of a compound of formula (VII), wherein R¹ and q are as hereinbefore defined, Formula (VII)

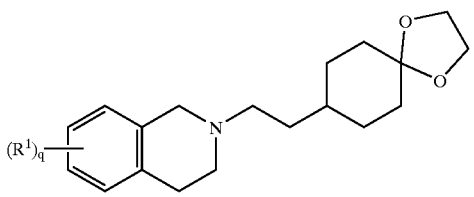

into a corresponding ketone, followed by reductive amination. This may be effected by methods well known in the art for (i) conversion of a ketal to a ketone in the presence of aqueous acid; followed by (ii) reductive amination of the ketone with $R^2NH_2$ or ammonium acetate in the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as methanol, ethanol or dichloroethane.

A compound of formula (VII) may itself be prepared by reacting a compound of formula (VIII):

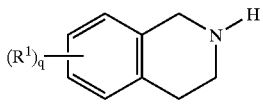

wherein $R^1$ and q are as hereinbefore defined;
with a compound of formula (IX):

Formula (IX)

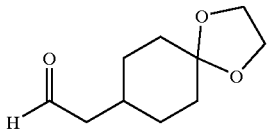

in the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol or dichloroethane.

The individual cis- and trans-isomers of a compound of formula (II) may be prepared starting from cis- or trans-4-amino-cyclohexaneacetic acid (T. P. Johnson, et al., J. Med. Chem., 1997, (20), 279–290) followed by functional group interchange and/or protection using methods well known in the art, to give the individual cis- or trans-isomers of a compound of formula (X):

Formula (X)

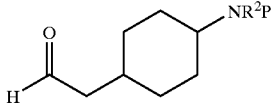

wherein $R^2$ is as hereinbefore defined, and P is a protecting group, for example trifluoroacetyl or tert-butoxycarbonyl. Subsequent reaction of a compound of formula (X) with a compound of formula (VIII) in the presence of a reducing agent as described above followed by deprotection using standard methodology gives the individual isomers of a compound of formula (II) wherein $R^2$ is as hereinbefore defined.

Compounds of formula (III) are known or may be prepared using standard procedures.

Compounds of formula (IV), (V) or (VI) may be prepared by processes analogous to (a), (b), (c) and (d) described above. Compounds $Ar^2W^1$, $Ar^3W^1$ and $Ar^3Hal$ are commercially available or may be prepared by standard methods. Compounds of formula (VIII) are known in the literature or may be prepared by known methods. The compound of formula (IX) is likewise known in the literature.

Compounds of formula (I) have been found to exhibit affinity for dopamine receptors, in particular the $D_3$ receptor, and are expected to be useful in the treatment of disease states which require modulation of such receptors, such as psychotic conditions. Compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4,295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors.

We have found that certain compounds of formula (I) are dopamine $D_3$ receptor antagonists, others may be agonists or partial agonists. The functional activity of compounds of the invention (i.e. whether they are antagonists, agonists or partial agonists) can be readily determined using the test method described hereinafter, which does not require undue experimentation. $D_3$ antagonists are of potential use as antipsychotic agents for example in the treatment of schizophrenia, schizo-affective disorders, psychotic depression, mania, paranoid and delusional disorders. Conditions which may be treated by dopamine $D_3$ receptor agonists include dyskinetic disorders such as Parkinson's disease, neuroleptic-induced parkinsonism and tardive dyskinesias; depression; anxiety, memory disorders, sexual dysfunction and drug (eg. cocaine) dependency.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

A preferred use for $D_3$ antagonists according to the present invention is in the treatment of psychoses such as schizophrenia.

A preferred use for $D_3$ agonists according to the present invention is in the treatment of dyskinetic disorders such as Parkinson's disease.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants $(K_i)$ of test compounds for displacement of $[^{125}I]$ iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homnogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @37° C.). The final pellet was resuspended in 50 mM Tris salts (pH 7.4 @37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM $[^{125}I]$ iodosulpride (~2000 Ci/mmol; Amersham, U. K.), and the test compound in a buffer containing 50 mM Tris salts (pH 7.4 @37° C.), 120 mM NaCl, 5 mM KCl, 2 mM $CaCl_2$, 1 mM $MgCl_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @37° C. ), 120 mM NaCl, 5 mM KCl, 2 mM $CaCl_2$, 1 mM $MgCl_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used. Competition curves were analysed simultaneously whenever possible using non-linear least-squares fitting procedures, capable of fitting one, two or three site models.

Compounds of Examples tested according to this method had pKi values in the range 7.0–9.1 at the human cloned dopamine $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell H M et al Science 1992 257 1906–1912) In Microphysiometer experiments, cells (hD2_CHO or hD3_ CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 μl/min. Each pump cycle lasted 90s. The pump was on for the first 60s and the acidification rate determined between 68 and 88s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. & Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Compounds of Examples tested according to this method were shown to be antagonists with pKb values within the range 7.0–10.0 at the human cloned dopamine $D_3$ receptor.

Pharmaceutical Formulations

The following represent typical pharmaceutical formulations according to the present invention, which may be prepared using standard methods.

| IV Infusion | |
| --- | --- |
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

| Tablet | |
| --- | --- |
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins

Diluent: e.g. Microcrystalline cellulose, lactose, starch

Binder: e.g. Polyvinylpyrrolidone, hydroxypropymethylcellulose

Disintegrant: e.g. Sodium starch glycollate, crospovidone

Lubricant: e.g. Magnesium stearate, sodium stearyl fumarate.

| Oral Suspension | |
| --- | --- |
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose

Diluent: e.g. sorbitol solution, typically water

Preservative: e.g. sodium benzoate

Buffer: e.g. citrate

Co-solvent: e.g. alcohol, propylene glycol, polyethylene glycol, cyclodextrin

The invention is further illustrated by the following non-limiting examples:

DESCRIPTION 1

7-Bromo-1,2,3,4-tetrahydroisoquinoline

A mixture of 7-bromo-2-trifluoroacetyl-1,2,3,4-tetrahydoisoquinoline (G. E. Stokker, Tetrahedron Letters 1996, 37, 5453) (43.4g, 0.14 mol), potassium carbonate (104.3g, 0.75 mol), methanol (1 L) and water (150ml) was heated at reflux for 1 h, then cooled and evaporated in vacuo. Residue was partitioned between water (1 L) and dichloromethane (4×200 ml). Combined extracts were dried ($Na_2SO_4$) and evaporated in vacuo to give an oil which was dissolved in hexane. The mixture was filtered and the filtrate evaporated in vacuo to give the title compound as an oil (17.7 g, 60%).

$^1$H NMR (CDCl$_3$) δ: 1.77 (1H, br s), 2.73 (2H, t, J=7 Hz), 3.13 (2H, t, J=7 Hz), 3.98 (2H, s), 6.96 (1H, d, J=9 Hz), 7.16 (1H, d, J=2 Hz), 7.26 (1H, dd, J=9, 2 Hz).

The following compounds were prepared in a similar manner to Description 1

(a) 7-Cyano-1,2,3,4-tetrahydroisoquinoline

Mass spectrum (API$^+$): Found 159 (MH$^+$). $C_{10}H_{10}N_2$ requires 158.

(b) 5-Trifluoromethyl-1,2,3,4-tetrahydroisoquinoline

Mass spectrum (API$^+$): Found 202 (MH$^+$). $C_{10}H_{10}F_3N$ requires 201.

(c) 5-Pentafluoroethyl-1,2,3,4-tetrahydroisoquinoline

Mass spectrum (API$^+$): Found 252 (MH$^+$). $C_{11}H_{10}F_5N$ requires 251.

(d) 6-Pentafluoroethyl-1,2,3,4-tetrahydroisoquinoline

Mass spectrum (API$^+$): Found 252 (MH$^+$). $C_{11}H_{10}F_5N$ requires 251

(e) 5,6-Difluoro-1,2,3,4-tetrahydroisoquinoline

Mass spectrum (API$^+$): Found 170 (MH$^+$). $C_9H_9F_2N$ requires 169.

DESCRIPTION 2

7Cyano-2-trifluoroacetyl-1,2,3,4-tetrahydroisoquinoline

A mixture of 7-bromo-2-trifluoroacetyl-1,2,3,4-tetrahydroisoquinoline (51.7 g, 0.168 mol), copper (I) cyanide (31.8 g, 0.35 mol) and N-methyl-2-pyrrolidinone (620 ml) was heated at reflux for 4 h, cooled, then partitioned between dilute aqueous ammonia (1.5 L) and dichloromethane (5×300ml). The combined organic extracts were dried (Na$_2$O$_4$) and evaporated in vacuo to give the title compound (42.6 g, 100%) as an oil.

Mass spectrum (API$^+$): Found 253 (M–H)$^+$. $C_{12}H_9F_3N_2O$ requires 254.

DESCRIPTION 3

2-(8-(1,4-Dioxa)spiro[4.5]decyl)acetaldehyde

A solution of 8-(2-hydroxyethyl)-1,4dioxaspiro[4.5]decane (20.7 g, 111 mmol) (M. A. Ciufolini, N. E. Byrne, J. Am. Chem. Soc. 113, 8016 (1991)) in dimethylsulfoxide (800 ml) was treated with triethylamine (150 ml), followed by sulfur trioxide pyridine complex (56.2 g, 350 mmol). The resulting mixture was stirred at room temperature for 0.5 h, and saturated sodium bicarbonate (1 L) was added with stirring. The resultant mixture was extracted with dichloromethane (3×1.5 L) and the combined extracts were dried (Na$_2$SO$_4$) and evaporated in vacuo to give a yellow oil which was purified by chromatography on silica gel (~300 g) with 0–15% ethyl acetate in hexane gradient elution to give the title compound as a yellow oil (17.68 g, 87%).

Mass spectrum (API$^+$): Found 185 (MH$^+$). $C_{10}H_{16}O$ requires 184. $^1$H NMR (CDCl$_3$) δ: 1.34 (2H, m), 1.58 (2H, m), 1.75 (4H, m), 1.96 (1H, m), 2.37 (2H dd, J=7, 2 Hz), 3.94 (4H, s), 9.87 (1H, t, J=2 Hz).

DESCRIPTION 4

8-(2-(2-(7-Cyano-1,2,3,4-tetrahydro)isoquinolyl)ethyl)-4dioxaspiro[4.5]decane

A mixture of 2-(8-(1,4-dioxa)spiro[4.5]decyl)acetaidehyde (3.9 g. 21.2 mmol), 7-cyano-1,2,3,4-tetrahdyroisoquinoline (3.35 g, 21.2 mmol), sodium triacetoxyborohydride (6.8 g, 32.1 mmol) and 1,2-dichloroethane (200 ml) was stirred at room temperature for 16 h. The reaction mixture was partitioned between dichloromethane (200 ml), and saturated potassium carbonate (400 ml). The organic extract was washed with brine (200 ml), dried (Na$_2$SO$_4$) and evaporated in vacuo to give an oil, which was purified by filtration through silica gel (~100 g) in ethyl acetate to give the title compound as an orange oil (6.11 g, 88%).

Mass spectrum (API$^+$): Found 327 (MH$^+$). $C_{20}H_{26}N_2O_2$ requires 326. $^1$H NMR (CDCl$_3$) δ: 1.35 (3H, m), 1.53 (4H, m), 1.72 (4H, m), 2.52 (2H, m), 2.73 (2H, t, J=7 Hz), 2.94 (2H, m), 3.60 (2H, s), 3.93 (4H, s), 7.18 (1H, d, J=9 Hz), 7.41 (1H, d, J=9 Hz).

DESCRIPTION 5

7-Cyano-2-(2-(1-(4-oxo)cyclohexyl)ethyl-1,2,3,4-tetrahydroisoquinoline 8-(2-(2-(7-cyano-1,2,3,-tetrahydro)isoquinolyl)ethyl)-1,4-dioxaspiro[4.5]decane (5.9 g, 18.1 mmol) was dissolved in a mixture of tetrahydrofuran (600 ml), and water (600 ml), then concentrated sulfuric acid (2.65 g, 27 mmol) was added and the mixture was stirred at room temperature for 66 h. The reaction mixture was evaporated in vacuo and the residues partitioned between ethyl acetate (1 L) and saturated potassium carbonate (400 ml). The organic extract was dried (Na$_2$SO$_4$) and evaporated in vacuo to give the title compound as a brown oil (5.1 g, 100%).

Mass spectrum (API$^+$): Found 283 (MH$^+$). $C_{18}H_{22}N_2O$ requires 282. $^1$H NMR (CDCl$_3$) δ: 1.44 (2H, m), 1.62 (2H, m), 1.85 (1H, m), 2.11 (3H, m), 2.38 (3H, m), 2.61 (2H, m), 2.78 (2H, m), 2.96 (2H, m), 3.64 (2H, s), 7.21 (1H, d, J=9Hz), 7.34 (1H, s), 7.43 (1H, d, J=9 Hz).

DESCRIPTION 6 cis and trans-2-(2(1-(4-Amino)cyclohexyl)ethyl-7-cyano-1,2,3,4-tetrahydroisoquinoline A mixture of 7-cyano-2-(2-(1-(4-oxo)cyclohexyl)ethyl-1,2,3,4-tetrahydroisoquinoline (4.5 g, 15.9 mmol), ammonium acetate (12.5 g, 158 mmol) sodium cyanoborohydride (6.9 g, 110 mmol) and methanol (225 ml) was heated at reflux for 1 h, then cooled and acidified to pH2 with 5N hydrochloric acid. The mixture was then basified using 2M sodium hydroxide and extracted with dichloromethane (2×400 ml). Combined extracts were dried (Na$_2$SO$_4$) and evaporated in vacuo to give the title compound as a brown oil (4.12 g, 92%).

Mass spectrum (API$^+$): Found 284 (MH$^+$). $C_{18}H_{25}N_3$ requires 283 $^1$H NMR (CDCl$_3$) δ: 0.92–1.19 (3H, m), 1.26 (1H, m), 1.46–1.65 (5H, m), 1.72–2.03 (5H, m), 2.53 (2H, m), 2.72 (2H, m), 2.94 (2H, t, J=7 Hz), 3.60 (2H, s), 7.18 (1H, d, J=8 Hz), 7.32 (1H, s), 7.41 (1H, d, J=8 Hz).

DESCRIPTION 7

6-Cyano-1,2,3,4-tetrahydroisoquinoline

Prepared in a similar manner to that described in H. G. Selnick et al., Synthetic Communications 25 (20) 3255 (1995).

Mass spectrum (API$^+$): Found 159 (MH$^+$). $C_{10}H_{10}N_2$ requires 158. $^1$H NMR (CDCl$_3$) δ: 2.47 (1H, br s), 2.82 (2H, m), 3.15 (2H, m), 4.05 (2H, s), 7.10 (1H, d, J=8 Hz), 7.40 (2H, m).

The following compound was prepared in a similar manner to Description 7

(a) 2-t-Butyloxycarbonyl-8cyano-1,2,3,4-tetrahydroisoquinoline $^1$H NMR (CDCl$_3$) δ: 1.51 (9H, s), 2.87 (2H, m), 3.68 (2H, m), 4.76 (2H, s), 7.26 (1H, m), 7.37 (1H, d, J=7 Hz), 7.52 (1H, d, J=7 Hz).

DESCRIPTION 8 trans-2-(1-(4-(N-tert-Butyloxycarbonyl)amino)cyclohexyl)acetic Acid, Methyl Ester A mixture of trans-(4-amino)cyclohexylactic acid hydrogen sulfate (T. P. Johnston et al; J. Med Chem., 1977, 20 (2), 279–290), (27.0 g, 106 mmol), conc. $H_2SO_4$ (3 ml), and methanol (300 ml) was stirred at reflux for 5 h. Resulting solution was filtered and the filtrate evaporated in vacuo to give a brown oil (36 g). A mixture of this material, triethylamine (36 ml; 26.1 g, 259 mmol), dichloromethane (600 ml) and di-t-butyl dicarbonate (25.5 g, 117 mmol) was stirred at 20° C. for 18 h. Resulting solution was partitioned between saturated aqueous $NaHCO_3$ (500 ml) and dichloromethane (3×200 ml), and the combined extracts were dried ($Na_2SO_4$) and evaporated in vacuo to give the tide compound (24.6 g, 86%) as a colourless solid.

$^1$H NMR (CDCl$_3$) δ: 1.08 (4H, m), 1.43 (9H, s), 1.76 (3H, m), 2.00 (2H, m), 2.20 (2H, d, J=7 Hz), 3.37 (1H, m), 3.66 (3H, s), 4.39 (1H, br s).

DESCRIPTION 9 trans-2-(1(4-(N-tert-Butyloxycarbonyl)amino) cyclohexyl)acetaldehyde

To a stirred solution of trans-2-(1-(4-(N-tert-butyloxycarbonyl)amino)cyclohexyl)acetic acid, methyl ester (46.0 g, 170 mmol) in dry toluene (920 ml) at −78° C. under argon was added a solution of di-isobutylaluminium hydride (1M; 285 ml; 285 mmol), dropwise over 0.5 h. Resulting solution was stirred for a further 0.3 h and quenched with a mixture of methanol (28 ml) in toluene (50 ml) and then poured into saturated aqueous potassium sodium tartrate (1.2 L). The resultant mixture was extracted with ether (4×1 L). The combined organic extracts were dried ($Na_2SO_4$) and evaporated in vacuo to give a waxy solid which was purified using silica gel, eluting with 10–50% ethyl acetate/hexane to give the title compound (21.77 g, 53%) as a colourless solid.

$^1$H NMR (CDCl$_3$) δ: 1.12 (4H, m), 1.44 (9H, s), 1.78 (3H, m), 2.00 (2H, m), 2.33 (2H, dd, J=7, 2 Hz), 3.37 (1H, m), 4.40 (1H, m), 9.75 (1H, m).

DESCRIPTION 10 trans-2-(2-(1-(4-(N-tert-Butyloxycarbonyl)amino) cyclohexyl)ethyl)-6-cyano-1,2,3,4-tetrahydroisoquinoline A mixture of trans-2-(1-(4-(N-tert-butyloxycarbonyl) amino)cyclohexyl)acetaldehyde (6.0 g, 24.9 mmol), 6-cyano-1,2,3,4-tetrahydroisoquinoline (3.93 g, 24.9 mmol), sodium triacetoxyborohydride (7.7 g, 36.3 mmol) in 1,2-dichloroethane (270 ml) was stirred at 20° C. for 16 h. Resulting solution was partitioned between aqueous $K_2CO_3$ (200 ml) and dichloromethane (100 ml), and the combined extracts were washed with brine (200 ml), dried (NaSO,) and evaporated in vacuo to a minimum volume and filtered through a pad of silica (100 g), washing with ethyl acetate. The filtrate was evaporated in vacuo to give the title compound (8.33 g, 87%) as a yellow solid.

$^1$H NMR (CDCl$_3$) δ: 1.08 (4H, m), 1.28 (1H, m), 1.44 (9H, s), 1.48 (2H, m), 1.78 (2H, m), 1.99 (2H, m), 2.52 (2H, m), 2.72 (2H, t, J=7 Hz), 2.91 (2H, ,m), 3.37 (1H, m), 3.63 (2H, m), 4.40 (1H, m), 7.12 (1H, d, J=8 Hz), 7.39 (2H, m).

The following compounds were prepared in a similar manner to Description 10.

(a) trans-2-(2-(1-(4-(N-tert-Butyloxycarbonyl)amino) cyclohexyl)ethyl)-7-cyano-1,2,3,4-tetrahydroisoquinoline $^1$H NMR (CDCl$_3$) δ: 1.06 (4H, m), 1.28 (1H, m), 1.44 (9H, s), 1.47 (2H, m), 1.77 (2H, m), 1.99 (2H, m), 2.52 (2H, m), 2.72 (2H, t, J=7 Hz), 2.94 (2H, m), 3.37 (1H, m), 3.60 (2H, s), 4.37 (1H, m), 7.18 (1H, d, J=8 Hz), 7.32 (1H, s), 7.39 (1H, d, J=8 Hz).

(b) trans-2-(2-(1-(4-(N-tert-Butyloxycarbonyl)amino) cyclohexyl)ethyl)-5-cyano-1,2,3,4-tetrahydroisoquinoline $^1$H NMR (CDCl$_3$) δ: 1.07 (4H, m), 1.28 (1H, m), 1.45 (9H, s), 1.49 (2H, m), 1.71 (2H, m), 2.01 (2H, m), 2.55 (2H, m), 2.78 (2H, t, J=7 Hz), 3.07 (2H, t, J=7 Hz), 3.38 (1H, m), 3.62 (2H, s), 4.39 (1H, m), 7.23 (2H, m), 7.49 (1H, dd, J=9, 2 Hz).

(c) trans-2-(2-(1-(4N-tert-Butyloxycarbonyl)methylamino) cyclohexyl)ethyl-7-cyano-1,2,3,4-tetrahydroisoquinoline $^1$H NMR (CDCl$_3$) δ: 1.10 (2H, m), 1.25 (1H, m), 1.40 (2H, m), 1.46 (9H, s), 1.50 (2H, m), 1.68 (2H, m), 1.84 (2H, m), 2.54 (2H, m), 2.73 (5H, m), 2.95 (2H, m), 3.59 (2H, s), 3.90 (1H, m), 7.18 (1H, d, J=9 Hz), 7.31 (1H, d, J=1 Hz), 7.40 (1H, dd, J=9 1 Hz).

(d) trans-6-Bromo-2-(2-(1-(4-N-tert-Butyloxycarbonyl) amino)cyclohexyl)ethyl-1,2,3,4-tetrahydroisoquinoline Mass Spectrum (API$^+$): Found 437 (MH$^+$). $C_{22}H_{33}{}^{79}BrN_2O_2$ requires 436.

(e) trans-2-(2-(1-(4-N tert-Butyloxycarbonyl)amino) cyclohexyl)ethyl-6-trifluoromethyl-1,2,3,4-tetrahydroisoquinoline Mass Spectrum (API$^+$): Found 427 (MH$^+$). $C_{23}H_{33}F_3N_2O_2$ requires 426.

(f) trans-2-(2-(1-(4-N-tert-butyloxycarbonyl)amino) cyclohexyl)ethyl6-trifluoromethoxy-1,2,3,4-tetrahydroisoquinoline Mass Spectrum (API$^+$): Found 443 (MH$^+$). $C_{23}H_{33}F_3N_2O_3$ requires 442.

(g) trans-2-(2-(1-(4-(N-t-Butyloxycarbonyl)amino) cyclohexyl)ethyl)-7-cyano-5-methyl-1,2,3,4-tetrahydroisoquinoline Mass spectrum (API$^+$): Found 398 (MH$^+$). $C_{24}H_{33}N_3O_2$ requires 397.

(h) trans-2-(2(1-(4(N-t-Butyloxycarbonyl)amino) cyclohexyl)ethyl)-7-cyano-6-methyl-1,2,3,4-tetrahydroisoquinoline Mass spectrum (API$^+$): Found 398 (MH$^+$). $C_{24}H_{35}N_3O_2$ requires 397.

(i) trans-2-(2-(1-(4-(N-t-Butyloxycarbonyl)amino) cyclohexyl)ethyl)-6-trifluoromethyl-1,2,3,4-tetrahydroisoquinoline Mass spectrum (API$^+$): Found 427 (MH$^+$). $C_{23}H_{33}F_3N_2O_2$ requires 426.

(j) trans-2-(2-(1-(4-(N-1-Butyloxycarbonyl)amino) cyclohexyl)ethyl)-6-trifluoromethoxy-1,2,3,4-tetrahydroisoquinoline Mass spectrum (API$^+$): Found 443 (MH$^+$). $C_{23}H_{33}F_3N_2O_3$ requires 442.

(k) trans2-(2-(1-(4-(N-1-Butyloxycarbonyl)amino) cyclohexyl)ethyl)-5-trifluoromethyl-1,2,3,4-tetrahydroisoquinoline Mass spectrum (API$^+$): Found 427 (MH$^+$). $C_{23}H_{33}F_3NO_2O_2$ requires 426.

(l) trans-2-(2-(1-(4-(N-t-Butyloxycarbonyl)amino) cyclohexyl)ethyl)-5-pentafluoroethyl-1,2,3,4-tetrahydroisoquinoline Mass spectrum (API$^+$): Found 477 (MH$^+$). $C_{24}H_{33}F_5N_2O_2$ requires 476.

(m) trans-2-(2-(1-(4-(N-t-Butyloxycarbonyl)amino) cyclohexyl)ethyl)-6-pentafluoroethyl-1,2,3,4-tetrahydroisoquinoline Mass spectrum (API$^+$): Found 477 (MH$^+$). $C_{24}H_{33}F_5N_2O_2$ requires 476.

(n) trans-2-(2-(1-(4-(N-t-Butyloxycarbonyl)amino) cyclohexyl)ethyl)-8-cyano-1,2,3,4-tetrahydroisoquinoline Mass spectrum (API⁺): Found 384 (MH⁺). $C_{23}H_{33}N_3O_2$ requires 383. ¹H NMR (CDCl₃) δ: 1.00–1.60 (16H, m), 1.69–2.10 (4H, m), 2.54–2.61 (2H, m), 2.72 (2H, m), 2.92 (2H, m), 3.37 (1H, br s), 3.77 (2H, s), 4.38 (1H, br s), 7.21 (1H, t, J=7 Hz), 7.33 (1H, d, J=7 Hz), 7.45 (1H, d, J=7 Hz).
(o) trans-2-(2-(1-(4-(N-t-Butyloxycarbonyl)amino)cyclohexyl)ethyl-5,6-difluoro-1,2,3,4-tetrahydroisoquinoline
Mass spectrum (API⁺): Found 395 (MH⁺). $C_{22}H_{32}F_2N_2O_2$ requires 394.

DESCRIPTION 11 trans-2-(2-(1-(4-Amino)cyclohexyl)ethyl)-6-cyano-1,2,3,4-tetrahydroisoquinoline A mixture of trans-2-(2-(1-(4-(N-tert-butyloxycarbonyl)amino)cyclohexyl)ethyl)-6-cyano-1,2,3,4-tetrahydroisoquinoline (8.3 g, 21.7 mmol), trifluoroacetic acid (15 ml) and dichloromethane (180 ml) was stirred at 20° C. for 2 h. Resulting solution was evaporated in vacuo and the residue partitioned between saturated aqueous $K_2CO_3$ (200 ml) and dichloromethane (2×100 ml). The combined organic extracts were washed with brine (100 ml), dried ($Na_2SO_4$) and evaporated in vacuo to give the title compound (4.99 g, 81%) as a brown oil.

Mass spectrum (API⁺): Found 284 (MH⁺). $C_{18}H_{25}N_3$ requires 283. ¹H NMR (CDCl₃) δ: 0.91–1.16 (4H, m), 1.22–1.40 (3H, m), 1.47 (2H, m), 1.72–191 (4H, m), 2.52 (2H, m), 2.59 (1H, m), 2.72 (2H, t, J=7 Hz), 2.92 (2H, m), 3.64 (2H, s), 7.11 (1H, d, J=8 Hz), 7.39 (2H, m).

The following compounds were prepared in a similar manner to Description 11
(a) trans-2-(2-(1-(4-Amino)cyclohexyl)ethyl)-7-cyano-1,2,3,4-tetrahydroisoquinoline
Mass spectrum (API⁺): Found 284 (MH⁺). $C_{18}H_{25}N_3$ requires 283. ¹H NMR (CDCl₃) δ: 0.91–1.16 (4H, m), 1.18–1.40(3H, m), 1.47 (2H, m), 1.73–1.92 (4H, m), 2.53 (2H, m), 2.62 (1H, m), 2.72 (2H, t, J=7 Hz), 2.94 (2H, m), 3.60 (2H, s), 7.19 (1H, d, J=8 Hz), 7.32 (1H, s), 7.41 (1H, d, J=8 Hz).
(b) trans-2-(2-(1-(4-Amino)cyclohexyl)ethyl)-5-cyano-1,2,3,4-tetrahydroisoquinoline
Mass spectrum (API⁺): Found 284 (MH⁺). $C_{18}H_{27}N_3$ requires 283. ¹H NMR (CDCl₃) δ: 0.92–1.18 (4H, m), 1.28 (1H, m), 1.50 (4H, m), 1.84 (4H, m), 2.48–2.70 (3H, m), 2.79 (2H, t, J=7 Hz), 3.06 (2H, t, J=7 Hz), 3.64 (2H, m), (2H, m), 7.49 (1H, dd, J=9, 2 Hz).
(c) trans-7-Cyano-2-(2-(1-(4-methylamino)cyclohexyl)ethyl)-1,2,3,4-tetrahydroisoquinoline
Mass spectrum (API⁺): Found 298 (MH⁺). $C_{19}H_{27}N_3$ requires 297.
(d) trans-2-(2(1-(4-Amino)cyclohexyl)ethyl)-6-bromo-1,2,3,4-tetrahydroisoquinoline
Mass spectrum (API⁺): Found 337 (MH⁺). $C_{17}H_{25}{}^{79}BrN_2$ requires 336.
(e) trans-2-(2-(1-(4-Amino)cyclohexyl)ethyl)-6-trifluoromethyl-1,2,3,4-tetrahydroisoquinoline
Mass spectrum (API⁺): Found 327 (MH⁺). $C_{18}H_{25}F_3N_2$ requires 326.
(f) trans-2-(2-(1-(4-Amino)cyclohexyl)ethyl)-6-trifluoromethoxy-1,2,3,4-tetrahydroisoquinoline
Mass spectrum (API⁺): Found 343 (MH⁺). $C_{18}H_{25}F_3N_2O$ requires 342.
(g) trans-2-(2-(1-(4-Amino)cyclohexyl)ethyl)-7-cyano-5-methyl-1,2,3,4-tetrahydroisoquinoline
Mass spectrum (API⁺): Found 298 (MH⁺). $C_{19}H_{27}N_3$ requires 297.
(h) trans-2(2-(1-(4-Amino)cyclohexyl)ethyl)-7-cyano-6-methyl-1,2,3,4-tetrahydroisoquinoline
Mass spectrum (API⁺): Found 298 (MH⁺). $C_{19}H_{27}N_3$ requires 297.
(i) trans-2-(2-(1-(4-Amino)cyclohexyl)ethyl)-6-trifluoromethyl-1,2,3,4-tetrahydroisoquinoline
Mass spectrum (API⁺): Found 327 (MH⁺). $C_{18}H_{25}F_3N_2$ requires 326.
(j) trans-2(2-(1-(4-Amino)cyclohexyl)ethyl)-6-trifluoromethoxy-1,2,3,4-tetrahydroisoquinoline
Mass spectrum (API⁺): Found 343 (MH⁺). $C_{18}H_{25}F_3N_2O$ requires 342.
(k) trans-2-(2-(1-(4-Amino)cyclohexyl)ethyl)-5-trifluoromethyl-1,2,3,4-tetrahydroisoquinoline
Mass spectrum (API⁺): Found 327 (MH⁺). $C_{18}H_{25}F_3N_2$ requires 326.
(l) trans-2-(2-(1-(4-Amino)cyclohexyl)ethyl)-5-pentafluoroethyl-1,2,3,4-tetrahydroisoquinoline
Mass spectrum (API⁺): Found 377 (MH⁺). $C_{19}H_{25}F_5N_2$ requires 376.
(m) trans-2-(2-(1-(4-Amino)cyclohexyl)ethyl)-6pentafluoroethyl-1,2,3,4-tetrahydroisoquinoline
Mass spectrum (API⁺): Found 377 (MH⁺). $C_{19}H_{25}F_5N_2$ requires 376.
(n) trans-2-(2-(1-(4-Amino)cyclohexyl)ethyl)-8-cyano-1,2,3,4-tetrahydroisoquinoline
Mass spectrum (API⁺): Found 284 (MH⁺). $C_{18}H_{25}N_3$ requires 283. ¹H NMR (CDCl₃) δ: 0.98–1.29 (9H, m), 1.70–1.90 (4H, m), 2.50–2.65 (3H, m), 2.73 (2H, m), 2.92 (2H, m), 3.78 (2H, s), 7.21 (1H, t, J=7 Hz), 7.33 (1H, d, J=7 Hz), 7.45 (1H, d, J=7 Hz).
(o) trans-2-(2-(1-(4-Amino)cyclohexyl)ethyl)-5,6-difluoro-1,2,3,4-tetrahydroisoquinoline
Mass spectrum (API⁺): Found 295 (MH⁺). $C_{17}H_{24}F_2N_2$ requires 294.

DESCRIPTION 12

(E)-3-(3-Methylsulfonyl)phenylpropenoic Acid

A mixture of methyl phenyl sulfone (15.0 g, 96 mmol), water (180 ml) and sulfuric acid (98%; 180 ml) was treated with N-bromosuccinimide (17.2 g, 96.6 mmol) then stirred at 85–90° C. for 4 h. Mixture was cooled, then partitioned between water (200 ml) and ether (3×150 ml). Combined organic extracts were washed with 10% aqueous NaOH (200 ml), dried (NaSO₄) and evaporated in vacuo to give a solid (19.4 g). The latter was heated at 140° C. with triethylamine (22 ml; 0.155 mol), ethyl acrylate (16.8 ml; 0.155 mol), tri-(2-tolyl)phosphine (3.0 g, 10 mmol) and palladium (II) acetate (1.2 g, 5 mmol) in acetonitrile (20 ml) under argon with stirring for 2 h. Mixture was cooled, then partitioned between ether (500 ml) and water (3×300 ml). Organic phase was dried ($Na_2O_4$) and evaporated in vacuo to give a solid. Chromatography on silica eluting with 20–100% ethyl acetate-hexane gave a solid (20.2 g), which was heated with sodium hydroxide (6.4 g, 0.16 mol) and water (500 ml) at reflux for 3 h. Resultant was cooled, then washed with ethyl acetate (500 ml). Aqueous phase was acidified with 10 M HCl (16 ml) and resulting solid filtered, to give the title compound (15.5 g, 71%) as a colourless solid.

Mass spectrum (API⁺): Found 225 (M–H⁺). $C_{10}H_{10}O_4S$ requires 226. ¹H NMR (DMSO-d₆) δ: 3.40 (3H, s), 6.845 (1H, d, J=16 Hz), 7.79 (1H, t, J=8 Hz), 7.80 (1H, d, J=16 Hz), 8.05 (1H, d, J=8 Hz), 8.18 (1H, d, J=8 Hz), 8.36 (1H, s), 12.75 (1H, br s).

DESCRIPTION 13

6-Cyanoindole-2-carboxylic Acid

A solution of 4-cyanobenzaldehyde (1.27 g, 9.69 mmol) and ethyl azidoacetate (5 g, 38.76 mmol) in methanol (6 ml)

was added dropwise over 0.16 h to a stirred solution of sodium methoxide (2.143 g, 39.7 mmol) in methanol (24 ml) at −8° C. The reaction was stirred with ice cooling for a further 3 h before being poured into ice/water (500 ml). The precipitate was filtered, washed with water and dried in vacuo. A sample of the residue (0.55 g) was dissolved in xylene (15 ml) and added dropwise to refluxing xylene (35 ml) over 0.75 h. After a further 1.5 h reflux the mixture was cooled and the precipitate filtered, washed with a small amount of xylene and dried in vacuo. The residue was dissolved in aqueous methanol (20 ml, 1:1) and sodium hydroxide (1 equivalent) added. The mixture was stirred at room temperature for 18 h, concentrated to half volume and poured into water (50 ml). The resultant solution was washed with ethyl acetate (50 ml) and the aqueous layer acidified with 2N HCl. The precipitate was filtered, washed with water and dried in vacuo to afford the title compound as a pale yellow solid (0.209 g, 11%).

$^1$H NMR (DMSO-d$_6$) δ: 7.25 (1H, d, J=1 Hz), 7.46 (1H, dd, J=8, 1 Hz), 7.91 (2H, m), 12.40 (1H, s), 13.40 (1H, br s).

DESCRIPTION 14

5-Bromo-2-trifluoroacetyl-1,2,3,4-tetrahydroisoquinoline

Prepared using a method similar to that described in G. E. Stokker, Tetrahedron Letters 1996, 37, 5453, in 90% yield.

$^1$H NMR (CDCl$_3$) δ: 2.97 (2H, m), 3.90 (2H, m), 4.75 and 4.82 (2H, 2×s), 7.13 (2H, m), 7.52 (1H, m).

The following compounds were prepared in a similar manner to Description 14

(a) 7-Bromo-5-methyl-2-trifluoroacetyl-1,2,3,4-tetrahydroisoquinoline $^1$H NMR (CDCl$_3$) δ: 2.25 (3H, s), 2.77 (2H, m), 3.88 (2H, m), 4.70 and 4.76 (2H, 2×s), 7.15 and 7.24 (1H, 2×m), 7.24 and 7.43 (1H, 2×m).

(b) 2-Trifluoroacetyl-5-trifluoromethyl-1,2,3,4-tetrahydroisoquinoline

Mass spectrum (API$^+$): Found 298 (MH$^+$). $C_{12}H_9F_6NO$ requires 297.

(c) 5,6-Difluoro-2-trifluoroacetyl-1,2,3,4-tetrahydroisoquinoline

Mass spectrum (API$^+$): Found 266 (MH$^+$). $C_{11}H_8F_5NO$ requires 265.

DESCRIPTION 15

5-Cyano-1,2,3,4-tetrahydroisoquinoline

Treatment of 5-bromo-2-trifluoroacetyl-1,2,3,4-tetrahydroisoquinoline in a manner similar to Description 2 gave the title compound (3.95 g, 86%) as a solid.

Mass spectrum (API$^+$): Found 159 (MH$^+$). $C_{10}H_{10}N_2$ requires 158. $^1$H NMR (DMSO-d$_6$) δ: 3.15 (2H, m), 3.51 (2H, m), 4.30 (2H, m), 7.45 (1H, t, J=9 Hz), 7.68 (1H, d, J=9 Hz), 7.80 (1H, d, J=9 Hz), 9.87 (2H, br s), (.HCl salt).

The following compound was prepared in a similar manner to Description 15
(a) 7-Cyano-5-methyl-1,2,3,4-tetrahydroisoquinoline Mass spectrum (API$^+$): Found 173 (MH$^+$). $C_{11}H_{12}N_2$ requires 172.

DESCRIPTION 16

2-(1-(4-(N-tert-Butyloxycarbonyl)methylamino) cyclohexyl)ethanol

A mixture of 2-(1-(4-(N-tert-butyloxycarbonyl)amino) cyclohexyl)acetic acid, methyl ester (2.10 g, 7.75 mmol), lithium aluminium hydride (0.62 g, 16.3 mmol) and ether (100 ml) was heated at reflux for 1.5 h, cooled, then treated dropwise with ice cooling, with saturated aqueous potassium sodium tartrate. Resulting supernatant solution was decanted off and evaporated in vacuo to give an oil (1.3 g). Chromatography on silica eluting with 50% ethyl acetate-hexane gave 2-(1-(4-(N-tert-butyloxycarbonyl)amino)cyclohexyl) ethanol. Further evaluation with 90:10:1 ethyl acetate-methanol-.880 ammonia gave a solid (0.64 g) which was treated wtih di-t-butyl dicarbonate (0.99 g, 4.5 mmol) in dichloromethane (20 ml) at 20° C. for 3 h. Mixture was evaporated in vacuo to give an oil. Chromatography on silica with 25–100% ethyl acetate-hexane gradient elution gave the title compound (0.89 g, 45%) as an oil.

$^1$H NMR (CDCl$_3$) δ: 1.11 (2H, m), 1.25–1.54 (6H, m), 1.47 (9H, s), 1.84 (2H, m), 2.72 (3H, s), 3.69 (2H, t, J=6 Hz), 3.95 (1H, br s).

DESCRIPTION 17

2-(1-(4-(N-tert-Butyloxycarbonyl)methylamino) cyclohexyl)acetaldehyde

To a stirred solution of oxalyl chloride (0.33 ml; 3.9 mmol) in dichloromethane (20 ml) under argon at −65° C. was added dry dimethyl sulfoxide (0.58 ml; 82 mmol). Mixture stirred at −65° C. for 0.2 h then a solution of 2-(1-(4-(N-tert-butyloxycarbonyl)methyl)cyclohexyl) ethanol (0.87 g, 3.4 mmol) in dichloromethane (5 ml) was added dropwise over 0.1 h. Mixture was stirred at −70° C. for 1 h, then triethylamine (2.5 ml; excess) was added dropwise and resultant stirred at −70° C. for 2 h then at 20° C. for 18 h. Resulting mixture was evaporated in vacuo and residue partitioned between ether (80 ml) and water (80 ml). Organic phase was washed with water (3×50 ml), dried (Na$_2$O$_4$) and evaporated in vacuo to give the title compound (0.80 g, 93%) as an oil.

$^1$H NMR (CDCl$_3$) δ: 1.14 (2H, m), 1.43 (1H, m), 1.45 (9H, s), 1.50 (2H, m), 1.68 (2H, m), 1.83 (2H, m), 2.34 (2H, dd, J=7,2 Hz), 2.72 (3H, s), 3.95 (1H, m), 9.77 (1H, t, J=2 Hz).

DESCRIPTION 18

(E)-3-(3-Acetyl)phenylpropenoic Acid

A mixture of 3-bromoacetophenone (1.99 g, 10 mmol), acrylic acid (0.8 g, 11 mmol), palladium (II) acetate (1.1 mg, 0.005 mmol), triphenylphosphine (0.026 g, 0.1 mmol) and tri-n-butylamine (5 ml, 21 mmol) were heated at 150° C. under argon for 2.5 h. After cooling, water (20 ml) was added, followed NaHCO$_3$ (2 g). The aqueous layer was separated, washed with dichloromethane and acidified with 5N Hcl. The precipitate was filtered, washed with water and dried to afford the title compound as a pale yellow solid (0.64 g, 34%).

Mass spectrum (API$^+$): Found 189 (M−H$^+$). $C_{11}H_{10}O$ requires 190. $^1$H NMR (DMSO-d$_6$) δ: 2.68 (3H, s), 6.73 (1H, d, J=16 Hz), 7.62 (1H, m), 7.73 (1H, d, J=16 Hz), 8.01 (2H, m), 8.30 (1H, s), 12.55 (1H, br s).

DESCRIPTION 19

(E)-3-(Acetamido)phenylpropenoic Acid

Prepared from 3-bromoacetanilide in a similar manner to that of Description 18, to afford the title compound as a colourless solid (1.29 g, 63%).

Mass spectrum (API$^{30}$): Found 204 (M−H$^{30}$). $C_{11}H_{11}NO_3$ requires 205. $^1$H-NMR (DMSO-d$_6$) δ: 2.21 (3H, s), 6.56 (1H, d, J=16 Hz), 7.50 (2H, m), 7.67 (1H, d, J=16 Hz), 7.73 (1H, m), 10.20 (1H, s), 12.60 (1H, br s).

DESCRIPTION 20

(3-Trifluoromethoxy)phenylethylamine Hydrochloride

To a stirred solution of zirconium (IV) chloride (11.8 g, 49.5 mmol) in dry tetrahydrofuran (200 ml) at 20° C. under argon was added, portionwise, sodium borohydride (7.5 g, 0.197 mol). Mixture was stirred for 1 h, then 3-trifluoromethoxyphenylacetonitrile (4.2 g, 20.9 mmol) was added. Stirring was continued for 24 h, then water (110 ml) was added dropwise, keeping the internal temperature below 10° C. The mixture was partitioned between dilute aqueous ammonia (500 ml) and ethyl acetate (4×100 ml). Organic extracts were dried ($Na_2SO_4$) and evaporated in vacuo to give an oil which was treated with ethereal HCl to give the title compound (2.1 g, 50%).

Mass spectrum ($API^+$): Found 206 ($MH^+$). $C_9H_{10}F_3NO$ requires 205.

The following compounds were prepared in a similar manner to description 20.

(a) (3-Triflouromethyl)phenethylamine hydrochloride
Mass spectrum ($API^+$): Found 190 ($MH^+$). $C_9H_{10}F_3N$ requires 189.

(b) (3-Bromo)phenethylamine hydrochloride
Mass spectrum ($API^+$): Found 200 ($MH^+$). $C_8H_{10}^{79}BrN$ requires 199.

(c) (4-Bromo-2-methyl)phenethylamine hydrochloride
NMR (DMSO-$d_6$) δ: 2.27 (3H, s), 2.88 (4H, m), 7.14 (1H, d, J=8 Hz), 7.34 (1H, dd, J=8, 2 Hz), 7.40 (1H, d, J=2 Hz), 8.20 (3H, br s).

(d) (4-bromo-3-methyl)phenethylamine hydrochloride
Mass spectrum ($API^+$): Found 216 ($MH^+$). $C_9H_{12}^{81}BrN$, requires 215.

(e) (2-Trifluoromethyl)phenethylamine hydrochloride
Mass spectrum ($API^+$): Found 190 ($MH^+$). $C_9H_{10}F_3N$ requires 189.

(f) (2,3-Difluoro)phenyethylamine hydrochloride
Mass spectrum ($API^+$): Found 158 ($MH^+$). $C_8H_9F_2N$ requires 157.

DESCRIPTION 21

N-(2-(3-Trifluoromethoxyphenyl)ethyl) trifluoroacetamide

To a stirred mixture of (3-triuoromethoxy) phenethylamine hydrochloride (5.85 g, 24.2 mmol) and 2,6-lutidine (5.65 ml; 5.19 g, 48.6 mmol) in dichloromethane (100 ml) at 0° C. under argon was added, dropwise, trifluoroacetic anhydride (3.42 ml, 5.08 g, 24.2 mmol). Resultant was stirred at 20° C. for 18 h then partitioned between water (100 ml) and dichloromethane (2×100 ml). Organic phase was washed with 1M hydrochloric acid (100 ml), saturated aqueous $NaHCO_3$ (100 ml), dried ($Na_2SO_4$) then evaporated in vacuo to give the title compound (6.14 g, 84%) as an oil.

Mass spectrum ($API^+$): Found 302 ($MH^+$). $C_{11}H_9F_6NO_2$ requires 301.

(a) N-(2,3-Trifluoromethyl)phenyl)ethyl)trifluoroacetamide
Mass spectrum ($API^-$): Found 284 ($M-H$)$^-$. $C_{11}H_9F_6NO$ requires 285.

(b) N-(2-(3-Bromophenyl)ethyl)trifluoroacetamide
Mass spectrum ($API^-$): Found 294 ($M-H$)$^-$. $C_{10}H_9^{79}BrF_3NO$ requires 295.

(c) N-(2-(4-Bromo-2-methylphenyl)ethyl) trifluoroacetamide
$^1$H NMR ($CDCl_3$) δ: 2.33 (3H, s), 2.85 (2H, t, J=7 Hz), 3.55 (2H, q, J=7 Hz), 6.45 (1H, br s), 6.94 (1H, d, J=8 Hz), 7.29 (1H, dd, J=8, 2 Hz), 7.35 (1H, d, J=2 Hz).

(d) N-(2-(4Bromo-3-methylphenyl)ethyl)trifluoroacetamide
$^1$H NMR ($CDCl_3$) δ: 2.41 (3H, s), 2.83 (2H, t, J=7 Hz), 3.60 (2H, q, J=7 Hz), 6.30 (1H, br s), 6.89 (1H, dd, J=8,2 Hz), 7.09 (1H, d, J=2 Hz), 7.49 (1H, d, J=8 Hz).

(e) N-(2-(2-trifluoromethylphenyl)ethyl)trifluoroacetamide
Mass spectrum ($API^+$): Found 284 ($M-H$)$^-$. $C_{11}H_9F_6NO$ requires 285.

(f) N-(2-(2,3-Difluorophenyl)ethyl)trifluoroacetamide
Mass spectrum ($API^+$): Found 252 ($M-H$)$^-$. $C_{10}H_8F_5NO$ requires 253.

DESCRIPTION 22

6-Trifluoromethoxy-1,2,3,4-tetrahydroisoquinoline Hydrochloride

N-(2-(3-Trifluoromethoxyphenyl)ethyl) trifluoroacetamide (6.14 g, 19.6 mmol) was treated in a manner similar to that described in G. E Stokker, Tetrahedron letters 37 5453 1996. The resulting product (6.13 g) was treated with anhydrous potassium carbonate (15.0 g, 0.108 mol) in methanol (140 ml) containing water (22 ml) at reflux for 2 h. The mixture was cooled, evaporated in vacuo, then partitioned between water (200 ml) and dichloromethane (4×50 ml). Combined organic extracts were dried ($Ha_2SO_4$) and evaporated in vacuo to give an oil (4.14 g), which was treated with ethereal HCl. Recrystallisation of the resulting solid from ethanol gave the title compound (2.33 g, 45%) as a colourless solid.

$^1$H NMR (DMSO-$d_6$) δ: 3.07 (2H, t, J=7 Hz), 3.39 (2H, t, J=7 Hz), 4.29 (2H, s), 7.27 (1H, d, J=9 Hz), 7.32 (1H, s), 7.40 (1H, d, J=9 Hz), 9.81 (2H, br s).

Mass spectrum ($API^+$): Found 218 ($MH^+$). $C_{10}H_{10}F_3NO$ requires 217.

The following compounds were prepared in a similar manner to description 22.

(a) 6-Trifluoromethyl-1,2,3,4-tetrahydroisiquinoline hydrochloride
Mass spectrum ($API^+$): Found 202 ($MH^+$). $C_{10}H_{10}F_3N$ requires 201.

(b) 6-Bromo-1,2,3,4-tetrahydroisoquinoline Hydrochloride
$^1$H NMR (DMSO-$d_6$) δ: 3.08 (2H, t, J=7 Hz), 3.35 (2H, t, J=7 Hz), 4.23 (2H, s), 7.15 (1H, d, J=9 Hz), 7.36 (1H, d, J=9 Hz), 7.39 (1H, s).

(c) 7-bromo-6-methyl-1,2,3,4-tetrahydroisoquinoline hydrochloride
$^1$H NMR (DMSO-$d_6$) δ: 2.32 (3H, s), 2.94 (2H, t, J=6 Hz), 3.33 (2H, t, J=6 Hz), 4.20 (2H, t, J=7.21 Hz, s), 7.21 (1H, s), 7.50 (1H, s), 9.64 (2H, br, s).

DESCRIPTION 23

6-Cyano-1,2,3,4-tetrahydroisoquinoline Hydrochloride

As an alternative procedure to that contained within Description 7, a solution of 6-bromo-1,2,3,4- tetrahydroisoquinoline hydrochloride (6.0 g, 24 mmol) and triethylamine (7.4 ml, 5.36 g, 53 mmol) in dichloromethane (100 ml) was treated with trifluoroacetic anhydride (3.7 ml, 5.54 g, 26.4 mmol) with ice cooling. Mixture was stirred at 20° C. for 1.5 h. then partitioned between saturated aqueous NaHCO$_3$ (250 ml) and dichloromethane (3×50 ml). Combined organic extracts were dried (Na$_2$SO$_4$) and evaporated in vacuo to give a solid (8.3 g). A mixture of the latter with copper (I) cyanide (5.1 g, 56.6 mmol) in 1-methyl-2-pyrrolidinone (100 ml) was heated at reflux under argon for 4 h, then cooled and partitioned between water (300 ml), 0.880 aqueous ammonia (100 ml) and dichloromethane (5×200 ml). Combined organic extracts were dried (Na$_2$SO$_4$) and evaporated in vacuo to give an oil. The latter was dissolved in ether and treated with ethereal HCl to give the title compound (4.47 g, 85%) as a colourless solid.

Mass spectrum (API$^+$): Found 159 (MH$^+$). C$_{10}$H$_{10}$N$_2$ requires 158.

The following compound was prepared in a similar manner to description 23

(a) 7-Cyano-6-methyl-1,2,3,4-tetrahydroisoquinoline Hydrochloride

Mass spectrum (API$^+$): Found 173 (MH$^+$). C$_{11}$H$_{12}$N requires 172.

DESCRIPTION 24

8-Cyano-1,2,3,4-tetrahydroisoquinoline

A mixture of 2-t-butyloxycarbonyl-8-cyano-1,2,3,4-tetrahydroisoquinoline (1.4 g, 5.4 mmol) and trifluoroacetic acid (2 ml) in dichloromethane (20m1) was stirred at 40° C. for 16 h. Mixture was evaporated in vacuo and the resulting residue partitioned between dichloromethane and saturated potassium carbonate solution. The aqueous layer was extracted with more dichloromethane (2×100 ml). The combined organic extracts were dried (Na$_2$SO$_4$) and evaporated in vacuo to afford the desired product as an amber oil (0.9 g, 100%).

Mass spectrum (API$^+$): Found 159 (MH$^+$). C$_{10}$H$_{10}$N$_2$ requires 158.

DESCRIPTION 25

2-t-Butoxycarbonyl-8trifuoromethylsulfonyloxy1,2,3,4-tetrahydroisoquinoline

A solution of 8-hydroxy-1,2,3,4-tetrahydroisoquinoline (2.55 g, 17 mmol) and di-tert-butyl dicarbonate (3.9 g, 17.9 mmol) in THF (250 ml) was allowed to stir at room temperature. The THF was removed in vacuo and the resulting residue purified by flash silica gel chromatography, eluted with dichloromethane to give an oil. An aliquot of this (3.2 g, 13 mmol) was dissolved in dry dichloromethane (50 ml). To this solution at −20° C. under argon, was added triethylamine (2.1 ml), followed by trifluoromethylsulfonic anhydride (2.4 ml, 14 mmol) in dichloromethane (2 ml) dropwise. The mixture was stirred from −20° C. to 0° C. over 3 hrs. It was poured into cold water and extracted with dichloromethane (3×50 ml). The combined organics extracts were washed with water, then brine and dried (Na$_2$O$_4$). Evaporation in vacuo gave an oil. Flash silica gel chromatography eluting with ethyl acetate and hexane afforded the desired product as an amber oil (4.3 g, 91%).

$^1$H NMR (CDCl$_3$) δ: 1.49 (9H, s), 2.88 (2H, m), 3.67 (2H, m), 4.64 (2H, br s), 7.15–7.27 (3H, m).

DESCRIPTION 26

5-Pentafluoroethyl-2-trifluoroacetyl-1,2,3,4-tetrahydroisoquinoline

A mixture of 5-bromo-2-trifluoroacetyl-1,2,3,4-tetrahydroisoquinoline (4.0 g, 13 mmol), sodium pentafluoropropionate (4.85 g, 26 mmol), copper (I) iodide (5.22 g, 27.2 mmol), toluene (70 ml) and dimethylformamide (70 ml) was heated under argon with Dean-Stark distillation (70 ml distillate collected), then heated at reflux for 18 h. The mixture was cooled, then poured into a mixture of water (150 ml) and 0.880 ammonia (150 ml). Resulting solution was extracted with dichloromethane (4×100 ml) and the combined extracts dried (Na$_2$SO$_4$) and evaporated in vacuo to give a solid. Chromatography on silica with 10–50% ether-hexane gradient elution gave the title compound (2.97 g, 66%) as a colourless solid.

Mass spectrum (API$^+$): Found 348 (MH$^+$). C$_{13}$H$_9$F$_8$NO requires 347. $^1$H NMR (CDCl$_3$) δ: 3.16 (2H, m), 3.83 (2H, m), 4.75 and 4.84 (2H, 2×s), 7.39 (2H, m), 7.55 (1H, m).

DESCRIPTION 27

6-Pentafluoroethyl-2trifluoroacetyl-1,2,3,4-tetrahydroisoquinoline

To a mixture of 6-bromo-1,2,3,4-tetrahydrisoquinoline hydrochloride (5.90 g, 23.7 mmol), triethylamine (8.3 ml; 6 g, 59 mmol) and dichloromethane (50 ml) at 0° C. was added trifluoroacetic anhydride (4.18 ml, 6.22 g, 29.6 mmol). Mixture was stirred at 20° C. for 18 h, then partitioned between saturated aqueous NaHCO, (200 ml) and dichloromethane (4×20 ml). Combined extracts were dried (Na$_2$SO$_4$) and evaporated in vacuo to give an oil (7.9 g). Treatment of an aliquot of the water (2.3 g, 7.5 mmol) with sodium pentafluoropropionate (2.79 g, 15 mmol), copper (I) iodide (3.0 g, 15.8 mmol), dimethylformamide (40 ml) and toluene (40 ml) in a similar manner to Description 26 gave the title compound (1.85 g, 71%) as a colourless solid.

Mass spectrum (API$^-$): Found 346 (M–H)$^-$. C$_{13}$H$_9$F$_8$NO requires 347. $^1$H NMR (CDCl$_3$) δ: 3.04 (2H, m), 3.89 (2H, m), 4.80 and 4.86 (2H, 2×s), 7.30 (1H, m), 7.45 (2H, m).

DESCRIPTION 28

(4-Bromo-2-methyl)phenylacetonitrile

A mixture of 4-bromo-2-methylbenzyl alcohol (36.6 g, 0.18 mol) and triethylamine (33 ml; 24 g, 0.237 mol) in dichloromethane (300 ml) was treated dropwise under argon with methylsulfonyl chloride (16 ml; 23.7 g, 0.207 mol) with ice cooling. Mixture was stirred at 20° C. for 64 h then partitioned between saturated aqueous NaHCO, (1 L) and dichloromethane (3×100 ml). Combined extracts were dried (Na$_2$SO$_4$) and evaporated in vacuo to give an oil (34.3 g). The latter was dissolved in dimethylformamide (150 ml) and treated with sodium cyanide (8.13 g, 0.166 mol). Mixture was stirred vigorously at 20° C. for 18 h then partitioned between ether (600 ml) and water (4×400 ml). Organic phase was dried (Na$_2$SO$_4$) and evaporated in vacuo to give the title compound (30.48 g, 78%) as an oil.

$^1$H NMR (CDCl$_3$) δ: 2.35 (3H, s), 3.51 (2H, s), 7.23 (1H, d, J=8 Hz), 7.38 (2H, m).

The following compound was prepared in a similar manner to Description 28.

(a) (4-Bromo-3-methyl)phenylacetonitrile $^1$H NMR (CDCl$_3$) δ: 2.42 (3H, s), 3.68 (2H, s), 7.00 (1H, dd, J=8, 2 Hz), 7.21 (1H, d, J=2 Hz), 7.55 (1H, d, J=8 Hz).

EXAMPLE 2

(E)-trans-7-Cyano-2-(2-(1-(4(3-(6-indolyl) propenoyl)amino)cyclohexyl)ethyl)-1,2,3,4-tetrahydroisoquinoline Prepared from (E)-3-(6-indolyl)propenoic acid in a similar manner to Example 1. Crystallisation from ethyl acetate gave the title compound (0.19 g, 34%) as a yellow solid.

Mass spectrum (API$^+$): Found 453 (MH$^+$). C$_{29}$H$_{32}$N$_4$O requires 452. $^1$H NMR (DMSO-d$_6$) δ: 1.06 (2H, m), 1.21 (2H, m), 1.30 (1H, m), 1.45 (2H, m), 1.86 (4H, m), 2.51 (2H, m), 2.67 (2H, m), 2.89 (2H, m), 3.58 (2H, s), 3.62 (1H, m), 6.46 (1H, d, J=3 Hz), 6.56 (1H, d, J=15 Hz), 7.24 (1H, d, J=8 Hz), 7.32 (1H, d, J=8 Hz), 7.44 (1H, d, J=3 Hz), 7.50 (1H, d, J=15 Hz), 7.56 (4H, m), 7.88 (1H, d, J=8 Hz), 11.34 (1H, m).

EXAMPLE 3 trans-(E)-6-Cyano-2-(2-(1-(4-(3-(3-methylsulfonyl) phenylpropenoyl)amino)cyclohexyl)ethyl-1,2,3,4-tetrahydroisoquinoline

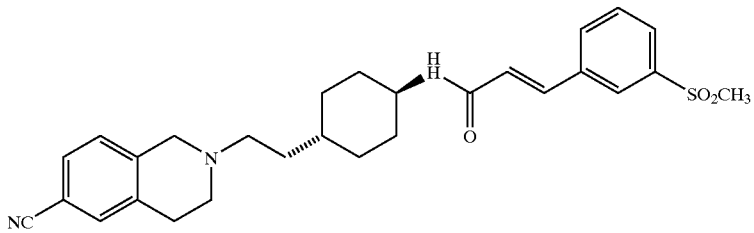

EXAMPLE 1 trans-7-Cyano2-(2-(1-(4-(2-indolyl)carboxamido) cyclohexyl)ethyl)-1,2,3,4-tetrahydroisoquinoline

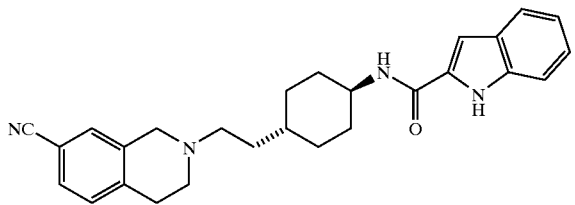

Alternative name: trans-N-[4-[2-(7-Cyano-1,2,3,4-tetrahydroisoquinolin-2-yl)ethyl]cyclohexyl]-1H-indole-2-carboxamide A mixture of cis and trans-2-(2-(1-(4-amino)cyclohexyl) ethyl-7-cyano-1,2,3,4-tetrahydroisoquinoline (350 mg, 1.24 mmol), indole-2-carboxylic acid (200 mg, 1.24 mmol), 1-ethyl-3-(3-dimethylaminopropyl)carbodiimide (238 mg, 1.24 mmol), 1-hydroxybenzotriazole (catalytic amount) and dichloromethane (8 ml) was shaken for 16 h. Saturated sodium bicarbonate (4 ml) was then added and the mixture shaken for 0.25 h. Chromatography of the organic layer on silica with 50–100% ethyl acetate in hexane and 0–10% methanol in ethyl acetate gradient elution gave the tide compound as a yellow solid (90 mg, 17%).

Mass spectrum (API$^+$): Found 427 (MH$^+$). C$_{27}$H$_{30}$N$_4$O requires 426. $^1$H NMR (CDCl$_3$) δ: 1.08–1.36 (4H, m), 1.50–1.70 (4H, m), 1.86 (1H, m), 2.12 (2H, m), 2.73 (2H, t, J=7 Hz), 2.94 (2H, m), 3.60 (2H, s), 3.95 (1H, m), 5.97 (1H, d, J=8 Hz), 6.81 (1H, m), 7.34 (2H, m), 7.42 (2H, t, J=8 Hz), 7.64 (1H, d, J=8 Hz), 9.22 (1H, br s).

Alternative name: trans-(E)-N-[4-[2-(6-Cyano-1,2,3,4-tetrahydroisoquinolin-2-yl)ethyl]cyclohexyl]-3-[3-(methylsulfonyl)phenyl]-2-propenamide A mixture of trans-2-(2-(1-(4-amino)cyclohexyl)ethyl)-6-cyano-1,2,3,4-tetrahydroisoquinoline (0.10 g, 0.35 mmol), (E)-3-(3-methylsulfonyl)phenylpropenoic acid (0.079 g, 0.35 mmol), 1-ethyl-3-(3-dimethylaminopropyl) carbodiimide hydrochloride (0.067 g, 0.35 mmol), 1-hydroxybenzotriazole (catalytic amount) and dichloromethane (5 ml) was treated in a manner to similar to Example 1 to give the title compound (0.065 g, 38%) as a off-white solid.

Mass spectrum (API$^+$): Found 492 (MH$^+$). C$_{28}$H$_{33}$N$_3$O$_3$S requires 491. $^1$H NMR (DMSO-d$_6$) δ: 0.97–1.38 (5H, m), 1.48 (2H, m), 1.84 (4H, m), 2.52 (2H, m), 2.68 (2H, m), 2.87 (2H, m), 3.29 (3H, s), 3.63 (3H, m), 6.81 (1H, d, J=16 Hz), 7.31 (1H, d, J=8 Hz), 7.52 (1H, d, J=16 Hz), 7.61 (2H, m), 7.72 (1, t, J=8 Hz), 7.93 (2H, m), 8.02 (2H, m).

EXAMPLE 4 trans-(E)-2-(2-(1-(4-(3-(3-Acetyl)phenylpropenoyl) amino)cyclohexyl)ethyl)-6-cyano-1,2,3,4-tetrahydroisoquinoline A mixture of trans-2-(2-(1-(4-amino)cyclohexyl)ethyl)-6-cyano-1,2,3,4-tetrahydroisoquinoline (0.10 g, 0.35 mmol), (E-3-(3-acetyl)phenylpropenoic acid (0.066 g, 0.35 mmol), 1-ethyl-3-(3-dimethylaminopropyl)carbodiimide hydrochloride (0.067 g, 0.35 mmol), 1-hydroxybenzotriazole (catalytic amount) and dichloromethane (5 ml) was treated in a manner similar to Example 1 to give the title compound (0.10 g, 63%) as a yellow solid.

Mass spectrum (API$^+$): Found 456 (MH$^+$). C$_{29}$H$_{33}$N$_3$O$_2$ requires 455. $^1$H NMR (DMSO-d$_6$) δ: 0.83–1.24 (5H, m), 1.33 (2H, m), 1.6–1.8 (4H, m), 2.36 (2H, m), 2.49 (3H, s), 2.52 (2H, m), 2.69 (2H, m), 3.48 (3H, m), 6.60 (1H, d, J=16 Hz), 7.14 (1H, d, J=8 Hz), 7.35 (1H, d, J=16 Hz), 7.44 (3H, m), 7.68 (1H, d, J=8 Hz), 7.68 (1H, d, J=8 Hz), 7.90 (1H, d, J=8 Hz), 8.0 (1H, s).

EXAMPLE 5 trans-7-Cyano-2-(2-(1-(4-(3-(4,6-dimethyl)pyrazolo[1,5-a]pyrimidyl)carboxamido)cyclohexyl)ethyl)1,2,3,4-tetrahydroisoquinoline A mixture of trans-2-(2-(1-(4-amino)cyclohexyl)ethyl)-7-cyano-1,2,3,4-tetrahydroisoquinoline (0.1 g, 0.353 mmol), 4,6-dimethylpyrazolo[1,5-a]pyrimidine-3-carboxylic acid (0.068 g, 0.353 mmol), 1-ethyl-3-(3-dimethylaminopropyl)carbodiimide hydrochloride (0.067 g, 0.353 mmol), 1-hydroxybenzotriazole (catalytic amount) and dichloromethane (4 ml) was treated in a manner similar to Example 1 to give the title compound (0.096 g, 60%) as a pale yellow gum.

Mass spectrum (API$^+$): Found 457 (MH$^+$). $C_{27}H_{32}N_6O$ requires 456. $^1$H NMR (DMSO-d$_6$) δ: 0.8–1.40 (7H, m), 1.80 (4H, m), 2.37 (3H, s), 2.42 (2H, m), 2.57 (2H, t, J=5 Hz), 2.71 (3H, s), 2.79 (2H, m), 3.48 (2H, s), 3.61 (1H, m), 6.50 (1H, s), 7.22 (1H, d, J=5 Hz), 7.47 (2H, m), 8.35 (2H, m).

EXAMPLE 6 trans-7-Cyano-2-(2-(1-(4-(2-(5-fluoro)indolyl)carboxamido)cyclohexyl)ethyl)-1,2,3,4-tetrahydroisoquinoline A mixture of trans-2-(2-(1-(4-amino)cyclohexyl)ethyl)-7-cyano-1,2,3,4-tetrahydroisoquinoline (0.1 g, 0.35 mmol), 5-fluoroindole-2-carboxylic acid (0.07 g, 0.35 mmol), 1-ethyl-3-(3-dimethylaminopropyl)carbodiimide hydrochloride (0.067 g, 0.35 mmol), 1-hydroxybenzotriazole (catalytic amount) and dichloromethane (8 ml) was treated in a manner similar to Example 1 to give the title compound (0.07 g, 45%) as an amber oil.

Mass spectrum (API$^+$): Found 445 (MH$^+$). $C_{27}H_{29}FN_4O$ requires 444.

$^1$H NMR (CDCl$_3$) δ: 1.10–1.40 (5H, m), 1.45–1.55 (2H, m), 1.80–1.95 (2H, m), 2.05–2.20 (2H, m), 2.56 (2H, m), 2.74 (2H, m), 2.95 (2H, m), 3.62 (2H, s), 3.93 (1H, m), 5.94 (1H, d, J=8 Hz), 6.75 (1H, m), 7.05 (1H, m), 7.19 (1H, d, J=8 Hz), 7.22–7.42 (4H, m), 9.25 (1H, br s).

EXAMPLE 7 trans-7-Cyano-2-(2-(1-(4-(2-(6-cyano)indolyl)carboxamido)cyclohexyl)ethyl)-1,2,3,4-tetrahydroisoquinoline A mixture of trans-2-(2-(1-(4-amino)cyclohexyl)ethyl)-7-cyano-1,2,3,4-tetrahydroisoquinoline (0.1 g, 0.352 mmol), 6-cyanoindole-2-carboxylic acid (0.066 g, 0.355 mmol), 1-ethyl-3-(3-dimethylaminopropyl)carbodiimide hydrochloride (0.068 g, 0.355 mmol), 1-hydroxybenzotriazole (catalytic amount) and dichloromethane (~10 ml) was treated in a manner similar to Example 1 to give the title compound (0.096 g, 60%) as a colourless solid.

Mass spectrum (API$^+$): Found 452 (MH$^+$). $C_{28}H_{29}N_5O$ requires 451. $^1$H NMR (CDCl$_3$) δ: 1.1–1.35 (5H, m), 1.51 (2H, m), 1.85 (2H, m), 2.05 (2H, m), 2.55 (2H, m), 2.75 (2H, t, J=6 Hz), 2.95 (2H, t, J=6 Hz), 3.58 (2H, s), 3.90 (1H, m), 6.97 (1H, s), 7.19 (1H, d, J=8 Hz), 7.30 (4H, m), 7.4 (1H, dd, J=1, 8 Hz), 7.68 (1H, d, J=8 Hz), 7.78 (1H, s).

EXAMPLE 8 trans-7-Cyano-2-(2-(1-(4-(3,4-methylenedioxy)benzamido)cyclohexyl)ethyl)-1,2,3,4-tetrahydroisoquinoline Prepared in a similar manner to Example 7, in 43% yield.

Mass spectrum (API$^+$): Found 432 (MH$^+$). $C_{25}H_{29}N_3O_3$ requires 431. $^1$H NMR (CDCl$_3$) δ: 1.10–1.40 (5H, m), 1.45–1.60 (2H, m), 1.75–1.90 (2H, m), 2.05–2.16 (2H, m), 2.50–2.60 (2H, m), 2.70–2.80 (2H, m), 2.90–3.00 (2H, m), 3.65 (2H, s), 3.89 (1H, m), 5.77 (1H, d, J=8 Hz), 6.01 (2H, s), 6.81 (1H, d, J=10 Hz), 7.15–7.50 (5H, m).

The following compounds were prepared in a similar manner to Example 8.

a) trans-7-Cyano-2-(2-(1-(4-(2-indolyl)-N-methylcarboxamido)cyclohexyl)ethyl)-1,2,3,4-tetrahydroisoquinoline Mass spectrum (API$^+$): Found 441 (MH$^+$). $C_{28}H_{32}N_4O$ requires 440. $^1$H NMR (CDCl$_3$+CD$_3$OD) δ: 1.05–1.48 (5H, m), 1.55 (2H, m), 1.90 (4H, m), 2.55 (2H, t, J=7 Hz), 2.72 (2H, t, J=7 Hz), 2.94 (2H, t, J=7 Hz), 3.20 (3H, br s), 3.60 (2H, s), 4.53 (1H, m), 6.78 (1H, br s), 7.05–7.48 (6H, m), 7.65 (1H, d, J=9 Hz), 9.44 (1H, br s).

b) trans-7-Cyano-2-(2-(1-(4-(2-(1-methyl)indolyl)carboxamido)cyclohexyl)ethyl-1,2,3,4-tetrahydroisoquinoline Mass spectrum (API$^+$): Found 441 (MH$^+$). $C_{28}H_{32}N_4O$ requires 440. $^1$H NMR (DMSO-d$_6$) δ: 0.96 (2H, m), 1.12–1.42 (5H, m), 1.75 (4H, m), 2.41 (2H, m), 2.58 (2H, m), 2.80 (2H, m), 3.49 (2H, m), 3.65 (1H, m), 3.88 (3H, s), 7.00 (2H, m), 7.20 (2H, m), 7.47 (4H, m), 8.17 (1H, d, J=8 Hz).

c) trans-7-Cyano-2-(2-(1-(4-(2-(5-nitro)indolyl)carboxamido)cyclohexyl)ethyl)-1,2,3,4-tetrahydroisoquinoline Mass spectrum (API$^+$): Found 472 (MH$^+$). $C_{27}H_{29}N_5O_3$ requires 471. $^1$H NMR (DMSO-d$_6$) δ: 0.98 (2H, m), 1.13–1.48 (5H, m), 1.76 (4H, m), 2.40 (2H, m), 2.57 (2H, m), 2.79 (2H, m), 3.48 (2H, m), 3.68 (1H, m), 7.21 (1H, d, J=8 Hz), 7.34 (1H, s), 7.46 (3H, m), 7.96 (1H, dd, J=9, 2 Hz), 8.41 (1H, d, J=8 Hz), 8.60 (1H, d, J=2 Hz), 12.22 (1H, br s).

d) trans-7-Cyano-2-(2-(1-(4-(2-(5-methylsulfonyl)indolyl)carboxamido)cyclohexyl)-ethyl-1,2,3,4-tetrahydroisoquinoline Mass spectrum (API$^+$): Found 505 (MH$^+$). $C_{28}H_{32}N_4O_3S$ requires 504. $^1$H NMR (DMSO-d$_6$) δ: 0.93 (2H, m), 1.09–1.38 (5H m), 1.71 (4H, m), 2.34 (2H, m), 2.52 (2H, m), 2.74 (2H, m), 3.04 (3H, s), 3.44 (2H, s), 3.64 (1H, m), 7.20 (2H, m), 7.48 (3H, m), 8.11 (2H, d, J=2 Hz), 8.32 (1H, d, J=8 Hz), 12.02 (1H, br s).

e) trans-7-Cyano-2-(2-(1-(4-(3-isoquinolyl)carboxamido)cyclohexyl)ethyl)-1,2,3,4-tetrahydroisoquinoline Mass spectrum (API$^+$): Found 439 (MH$^+$). $C_{28}H_{30}N_4O$ requires 438. $^1$H NMR (CDCl$_3$) δ: 1.11–1.44 (4H, m), 1.56 (2H, m), 1.88 (2H, m), 2.01 (1H, m), 2.14 (2H, m), 2.58 (2H, m), 2.76 (2H, t, J=7 Hz), 2.97 (2H, m), 3.64 (2H, s), 3.99 (1H, m), 7.19 (1H, d, J=8 Hz), 7.32 (1H, s), 7.39 (1H, d, J=8 Hz), 7.73 (2H, m), 8.04 (3H, m), 8.62 (1H, s), 9.15 (1H, s).

f) trans-7-Cyano-2-(2-(1-(4-(2-(5-methoxy)indolyl)carboxamido)cyclohexyl)ethyl)-1,2,4-tetrahydroisoquinoline Mass spectrum (API$^+$): Found 457 (MH$^+$). $C_{28}H_{32}N_4O_2$ requires 456. $^1$H NMR (CDCl$_3$) δ: 1.15–1.40 (5H, m), 1.50–1.58 (2H, m), 1.80–1.90 (2H, m), 2.10–2.20 (2H, m), 2.50–2.60 (2H, m), 2.70–2.80 (2H, m), 2.90–3.00 (2H, m), 3.49 (2H, s), 3.85 (3H, s), 3.95 (1H, m), 5.90 (1H, d, J=8 Hz), 6.70 (1H, d, J=2 Hz), 6.96 (1H, dd, J=2, 8 Hz), 7.05 (1H, d, J=2 Hz), 7.20 (1H, d, J=7.5 Hz), 7.30–7.37 (2H, m), 7.40–7.46 (1H, m), 9.08 (1H, br s).

g) trans-2-(2-(1-(4-(4-(4-Acetyl)phenyl)benzoyl)aminocyclohexyl)ethyl)-6-cyano-1,2,3,4-tetrahydroisoquinoline Mass spectrum (API$^+$): Found 506 (MH$^+$). $C_{33}H_{35}N_3O_2$ requires 505. $^1$H NMR (DMSO-d$_6$) δ: 1.10 (2H, m), 1.24–1.54 (5H, m), 1.87 (4H, m), 2.52 (2H, m), 2.65 (3H, s), 2.68 (2H, m), 2.87 (2H, m), 3.64 (2H, s), 3.79 (1H, m), 7.31 (1H, d, J=8 Hz), 7.59 (2H, m), 7.91 (4H, m), 8.00 (2H, d, J=8 Hz) 8.08 (2H, d, J=8 Hz), 8.32 (1H, d, J=8 Hz).

h) trans-7-Cyano-2-(2-(1-(4-(2-(7-nitro)indolyl)carboxamido)cyclohexyl)ethyl-1,2,3,4-tetrahydroisoquinoline Mass spectrum (API$^+$): Found 472 (MH$^+$). $C_{27}H_{29}N_5O_3$ requires 471. $^1$H NMR (DMSO-d$_6$) δ: 1.07 (2H, m), 1.32 (3H, m), 1.60 (2H, m), 1.79 (2H, m), 1.90 (2H, m), 2.80–3.25 (6H, m), 3.30 (2H, s), 3.23 (1H, m), 7.28 (1H, t, J=9 Hz), 7.35 (2H, m), 7.65 (2H, m), 8.15 (2H, m), 8.29 (1H, d, J=9 Hz), 11.34 (1H, br s).

i) trans-7-Cyano-2-(2-(1-(4-(2-(5-methyl)indolyl)carboxamido)cyclohexyl)ethyl)-1,2,3,4-tetrahydroisoquinoline Mass spectrum (API$^+$): Found 441 (MH$^+$). $C_{28}H_{32}N_4O$ requires 440. $^1$H NMR (CDCl$_3$+CD$_3$OD) δ: 1.06–1.48 (5H, m), 1.57 (2H, m), 1.89 (2H, m), 2.07 (2H, m), 2.43 (3H, s), 2.61 (2H, m), 2.84 (2H, t, J=7 Hz), 3.00 (2H, m), 3.66 (2H, s), 3.90 (1H, m), 6.94 (1H, s), 7.11 (1H, d, J=9 Hz), 7.15–7.50 (6H, m).

j) trans-7-Cyano-2-(2-(1-(4-(2-(1H)-pyrrolo[3,2-b]pyridyl)carboxamido)cyclohexyl)ethyl)-1,2,3,4-tetrahydroisoquinoline Mass spectrum (API$^+$): Found 428 (MH$^+$). $C_{26}H_{29}N_5O$ requires 427. $^1$H NMR (CDCl$_3$+CD$_3$OD) δ: 1.06–1.65 (7H, m), 1.90 (2H, m), 2.07 (2H, m), 2.60 (2H, m), 2.75 (2H, m), 2.98 (2H, m), 3.65 (2H, s), 3.94 (1H, m), 7.10 (1H, s), 7.24 (2H, m), 7.30 (1H, s), 7.36 (1H, m), 7.44 (1H, d, J=9 Hz), 7.83 (1H, d, J=9 Hz), 8.44 (1H, d, J=5 Hz).

k) trans-7-Cyano-2-(2-(1-(4-(3-pyrazolyl)carboxamido)cyclohexyl)ethyl)-1,2,3,4-tetrahydroisoquinoline Mass spectrum (API$^+$): Found 378 (MH$^+$). $C_{22}H_{27}N_5O$ requires 377. $^1$H NMR (CDCl$_3$+CD$_3$OD) δ: 1.04–1.45 (5H, m), 1.54 (2H, m), 1.85 (2H, m), 2.05 (2H, m), 2.55 (2H, m), 2.75 (2H, m), 2.98 (2H, m), 3.63 (2H, s), 3.85 (1H, m), 6.49 (1H, m), 7.22 (1H, d, J=9 Hz), 7.34 (1H, s), 7.43 (1H, d, J=9 Hz), 7.93 (2H, br s).

l) trans-7-Cyano-2-(2-(1-(4-(6-(1-methyl)benzimidazolyl)carboxamido)cyclohexyl)eyhyl)-1,2,3,4-tetrahydroisoquinoline Mass spectrum (API$^+$): Found 442 (MH$^+$). $C_{27}H_{31}N_5O$ requires 441. $^1$H NMR (CDCl$_3$) δ: 1.03–1.47 (5H, m), 1.55 (2H, m), 1.87 (2H, m), 2.16 (2H, m), 2.56 (2H, m), 2.75 (2H, t, J=7 Hz), 2.96 (2H, m), 3.64 (2H, s), 3.91 (3H, s) 4.00 (1H, m), 6.04 (1H, d, J=10 Hz), 7.18 (1H, d, J=8 Hz), 7.34 (1H, s), 7.41 (1H, d, J=8 Hz), 7.56 (1H, dd, J=9, 2 Hz), 7.79 (1H, d, J=9 Hz), 7.96 (1H, s), 8.03 (1H, d, J=2 Hz).

m) trans-7-Cyano-2-(2-(1-(4-(5-(1,2-dihydro)benzofuranyl)carboxamido)cyclohexyl)ethyl)-1,2,3,4-tetrahydroisoquinoline Mass spectrum (API$^+$): Found 430 (MH$^+$). $C_{27}H_{31}N_3O_2$ requires 429. $^1$H NMR (CDCl$_3$) δ: 1.05–1.45 (5H, m), 1.53 (2H, m), 1.85 (2H, m), 2.09 (2H, m), 2.54 (2H, m), 2.72 (2H, t, J=7 Hz), 2.95 (2H, m), 3.22 (2H, t, J=10 Hz), 3.62 (2H, s), 3.90 (1H, m), 4.63 (2H, t, J=10 Hz), 5.83 (1H, d, J=10 Hz), 6.26 (1H, d, J=9 Hz), 7.20 (1H, d, J=9 Hz), 7.33 (1H, s), 7.39 (1H, d, J=9 Hz), 7.52 (1H, dd, J=9, 2 Hz), 7.66 (1H, d, J=2 Hz).

n) trans-7-Cyano-2-(2-(1-(4-(2-thieno[3,2-b]thiophenyl)carboxamido)cyclohexyl)ethyl-1,2,3,4-tetrahydroisoquinoline Mass spectrum (API$^+$): Found 450 (MH$^+$). $C_{25}H_{27}N_3OS_2$ requires 449. $^1$H NMR (CDCl$_3$) δ: 1.03–1.47 (5H, m), 1.55 (2H, m), 1.85 (2H, m), 2.13 (2H, m), 2.53 (2H, m), 2.75 (2H, m), 2.95 (2H, m), 3.63 (2H, s), 3.94 (1H, m), 5.85 (1H, m), 7.12–7.48 (4H, m), 7.51 (1H, d, J=5 Hz), 7.70 (1H, s).

o) trans-7-Cyano-2-(2-(1-(4-(4-indolyl)carboxamido)cyclohexyl)ethyl)-1,2,3,4-tetrahydroisoquinoline Mass spectrum (API$^+$): Found 427 (MH$^+$). $C_{27}H_{30}N_4O$ requires 426. $^1$H NMR (CDCl$_3$) δ: 1.15–1.21 (5H, m), 1.55 (2H, m), 1.85 (2H, m), 2.2 (2H, m), 2.55 (2H, t, J=6 Hz), 2.75 (2H, t, J=6 Hz), 2.95 (2H, m), 3.62 (2H, s), 4.05 (1H, m), 6.05 (1H, d, J=8 Hz), 6.9 (1H, m), 7.15–7.22 (1H, m), 7.25 (1H, s), 7.32 (2H, m), 7.40 (1H, m), 7.50 (2H, m), 8.40 (1H, br s).

p) trans-7-Cyano-2-(2-(1-(4-(2-(6-methoxy)indolyl)carboxamido)cyclohexyl)ethyl-1,2,3,4-tetrahydroisoquinoline Mass spectrum (API$^+$): Found 457 (MH$^+$). $C_{28}H_{32}N_4O_2$ requires 456. $^1$H NMR (CDCl$_3$) δ: 1.15–1.30 (5H, m), 1.55 (2H, m), 1.85 (2H, m), 2.10 (2H, m), 2.55 (2H, m), 2.75 (2H, t, J=6 Hz), 2.94 (2H, t, J=6 Hz), 3.62 (2H, s), 3.85 (3H, s), 3.92 (1H, m), 5.85 (1H, d, J=8 Hz), 6.70 (1H, d, J=1 Hz), 6.80 (1H, dd, J=8, 1 Hz), 6.85 (1H, br s), 7.2 (1H, d, J=8 Hz), 7.30 (1H, s), 7.40 (1H, d, J=8 Hz), 7.50 (1H, d, J=8 Hz), 8.90 (1H, s).

q) trans-7-Cyano-2-(2-(1-(4-(2-(6-chloro)indolyl)carboxamido)cyclohexyl)ethyl)-1,2,3,4-tetrahydroisoquinoline Mass spectrum (API$^+$): Found 461 (MH$^+$). $C_{27}H_{29}{}^{35}ClN_4O$ requires 460. $^1$H NMR (CDCl$_3$) δ: 1.10–1.32 (5H, m), 1.48–1.60 (2H, m), 1.85 (2H, m), 2.08 (2H, m), 2.60 (2H, m), 2.74 (2H, m), 2.95 (2H, m), 3.62 (2H, s), 3.88 (1H, s), 6.62 (1H, m), 6.85 (1H, s), 7.05 (1H, dd, J=8, 1 Hz), 7.20 (1H, d, J=8 Hz), 7.30 (1H, m), 7.40 (2H, m), 7.52 (1H, d, J=8 Hz), 10.22 (1H, s).

r) trans-7-Cyano-2-(2-(1-(4-(2-(6-fluoro)indolyl)carboxamido)cyclohexyl)ethyl)-1,2,3,4-tetrahydroisoquinoline Mass spectrum (API$^+$): Found 445 (MH$^+$). $C_{27}H_{29}FN_4O$ requires 444. $^1$H NMR (CDCl$_3$) δ: 1.09–1.35 (5H, m), 1.50–1.60 (2H, m), 1.88 (2H, m), 2.09 (2H, m), 2.54–2.62 (2H, m), 2.76 (2H, t, J=6 Hz), 2.96 (2H, t, J=6 Hz), 3.63 (2H, s), 3.88 (1H, m), 6.66 (1H, d, J=8 Hz), 6.90 (2H, m), 7.10 (1H, dd, J=8, 2 Hz), 7.22 (1H, d, J=8 Hz), 7.32 (2H, m), 7.42 (1H, dd, J=8, 2 Hz), 7.5 (1H, m).

s) trans-7-Cyano-2-(2-(1-(4-(2-(6-methyl)indolyl)carboxamido)cyclohexyl)ethyl)-1,2,3,4-tetrahydroisoquinoline Mass spectrum (API$^+$): Found 441 (MH$^+$). $C_{28}H_{32}N_4O$ requires 440. $^1$H NMR (CDCl$_3$) δ: 1.10–1.35 (5H, m), 1.53 (2H, m), 1.87 (2H, m), 2.09 (2H, m), 2.46 (3H, s), 2.59 (2H, m), 2.78 (2H, m), 3.0 (2H, m), 3.66 (2H, s), 3.95 (1H, s), 6.95 (2H, m), 7.24 (2H, m), 7.34 (1H, m), 7.45 (2H, m), 7.51 (1H, m), 7.98 (1H, m).

t) trans-2-(2-(1-(4-(2-(5-Chloro)benzofuranyl)carboxamido)cyclohexyl)ethyl)-7-cyano-1,2,3,4-tetrahydroisoquinoline Mass spectrum (API$^+$): Found 462 (MH$^+$). $C_{27}H_{28}{}^{35}ClN_3O_2$ requires 461. $^1$H NMR (DMSO-d$_6$) δ: 0.91–1.36 (7H, m), 1.72 4H, m), 2.37 (2H, m), 2.56 (2H, t, J=6 Hz), 2.76 (2H, t, J=6 Hz), 3.47 (2H, s), 3.63 (1H, m), 7.21 (1H, d, J=8 Hz), 7.36 (1H, dd, J=8, 2 Hz), 7.42 (1H, s), 7.44 (2H, m), 7.60 (1H, d, J=8 Hz), 7.77 (1H, d, J=2 Hz), 8.48 (1H, d, J=8 Hz).

u) trans-2-(2-(1-(4-(2-(3-Amino)naphthyl)carboxamido) cyclohexyl)ethyl)-7-cyano-1,2,3,4-tetrahydroisoquinoline Mass spectrum (API$^+$): Found 453 (MH$^+$). $C_{29}H_{32}N_4O$ requires 452. $^1$H NMR (DMSO-d$_6$) δ: 0.8–1.40 (7H, m), 1.65 (4H, m), 2.28 (2H, m), 2.45 (2H, t, J=6 Hz), 2.67 (2H, t, J=6 Hz), 3.36 (2H, s), 3.55 (1H, m), 5.83 (2H, br s), 6.73 (1H,s), 6.92 (1H, m), 7.10 (2H, m), 7.29 (1H, d, J=8 Hz), 7.32 (2H, m), 7.48 (1H, d, J=8 Hz), 7.75 (1H, s), 8.14 (1H, d, J=8 Hz).

v) trans-7-Cyano-2-(2-(1-(4-(2-thienyl)carboxamido) cyclohexyl)ethyl)-1,2,3,4-tetrahydroisoquinoline Mass spectrum (API$^+$): Found 394 (MH$^+$). $C_{23}H_{27}N_3OS$ requires 393. $^1$H NMR (DMSO-d$_6$) δ: 1.00–1.60 (7H, m), 1.87 (4H, m), 2.52 (2H, m), 2.71 (2H, t, J=6 Hz), 2.91 (2H, t, J=6 Hz), 3.62 (2H, s), 3.73 (1H, m), 7.17 (1H, m), 7.35 (1H, d, J=8 Hz), 7.62 (2H, m), 7.77 (1H, m), 7.83 (1H, m), 8.26 (1H, d, J=7 Hz).

w) trans-7-Cyano-2-(2-(1-(4-(2-naphthyl)carboxamido) cyclohexyl)ethyl)-1,2,3,4-tetrahydroisoquinoline Mass spectrum (API$^+$): Found 438 (MH$^+$). $C_{29}H_{31}N_3O$ requires 437. $^1$H NMR (DMSO-d$_6$) δ: 1.10–1.70 (7H, m), 2.07 (4H, m), 2.63 (2H, m), 2.82 (2H, t, J=6 Hz), 3.30 (2H, t, J=6 Hz), 3.73 (2H, s), 3.97 (1H, m), 7.64 (1H, d, J=8 Hz), 7.75 (4H, m), 8.10 (4H, m), 8.53 (1H, d, J=8 Hz), 8.58 (1H, s).

x) trans-7-Cyano-2-(2-(1-(4-(3-indolyl)carboxamido) cyclohexyl)ethyl)-1,2,3,4-tetrahydroisoquinoline Mass spectrum (API$^+$): Found 427 (MH$^+$). $C_{27}H_{30}N_4O$ requires 426. $^1$H NMR (DMSO-d$_6$) δ: 0.9–1.55 (7H, m), 1.82 (4H, m), 2.46 (2H, m), 2.64 (2H, t, J=6 Hz), 2.84 (2H, t, J=6 Hz), 3.55 (2H, s), 3.71 (1H, m), 7.08 (2H, m), 7.28 (1H, d, J=8 Hz), 7.37 (1H, m), 7.56 (3H, m), 8.00 (1H, d, J=2 Hz), 8.11 (1H, m), 11.5 (1H, br s).

y) trans-(E)-7-Cyano-2-(2-(1-(4-(3-phenylpropenoyl) amino)cyclohexyl)ethyl)-1,2,3,4-tetrahydroisoquinoline Mass spectrum (API$^+$): Found 414 (MH$^+$). $C_{27}H_{31}N_3O$ requires 413. $^1$H NMR (DMSO-d$_6$) δ: 1.00–1.60 (7H, m), 1.90 (4H, m), 2.54 (2H, m), 2.74 (2H, t, J=6 Hz), 2.95 (2H, t, J=6 Hz), 3.65 (2H, s), 3.67 (1H, m), 6.69 (1H, d, J=16 Hz), 7.38 (1H, d, J=8 Hz), 7.46 (4H, m), 7.65 (4H, m), 8.07 (1H, d, J=8 Hz).

z) trans-6-Cyano-2-(2-(1-(4-(1-naphthyl)carboxamido) cyclohexyl)ethyl-1,2,3,4-tetrahydroisoquinoline Mass spectrum (API$^+$): Found 438 (MH$^+$). $C_{29}H_{31}N_3O$ requires 437. $^1$H NMR (DMSO-d$_6$) δ: 1.08 (2H, m), 1.30 (3H, m), 1.47 (2H, m), 1.83 (2H, m), 1.97 (2H, m), 2.52 (2H, m), 2.67 (2H, m), 2.86 (2H, m), 3.63 (2H, s), 3.81 (1H, m), 7.30 (1H, d, J=8 Hz), 7.54 (6H, m), 7.99 (2H, m), 8.17 (1H, m), 8.42 (1H, d, J=8 Hz).

a1) trans-2-(2-(1-(4-(2-Benzo[b]thienyl)carboxamido) cyclohexyl)ethyl)-6-cyano-1,2,3,4-tetrahydroisoquinoline Mass spectrum (API$^+$): Found 444 (MH$^+$). $C_{27}H_{29}N_3OS$ requires 443. $^1$H NMR (DMSO-d$_6$) δ: 0.85 (2H, m), 0.99–1.33 (5H, m), 1.66 (4H, m), 2.28 (2H, m), 2.47 (2H, m), 2.66 (2H, m), 3.43 (2H, s), 3.64 (1H, m), 7.09 (1H, d, J=8 Hz), 7.26 (2H, m), 7.39 (2H, m), 7,74 (1H, m), 7.84 (1H, m), 7.94 (1H, s), 8.35 (1H, d, J=8 Hz).

b1) trans-6-Cyano-2-(2-(1-(4-(5-indolyl)carboxamido) cyclohexyl)ethyl)-1,2,3,4-tetrahydroisoquinoline Mass spectrum (API$^+$): Found 427 (MH$^+$). $C_{27}H_{30}N_4O$ requires 426. $^1$H NMR (DMSO-d$_6$) δ: 0.85 (2H, m), 1.01–1.29 (5H, m), 1.58 (4H, m), 2.27 (2H, m), 2.44 (2H, m), 2.63 (2H, m), 3.40 (2H, s), 3.54 (1H, m), 6.30 (1H, d, J=3 Hz), 7.08 (1H, d, J=8 Hz), 7.18 (2H, m), 7.38 (3H, m), 7.82 (1H, d, J=8 Hz), 7.90 (1H, s), 11.11 (1H, br s).

c1) trans-6-Cyano-2-(2-(1-(4-(6-indolyl)carboxamido) cyclohexyl)ethyl)-1,2,3,4-tetrahydroisoquinoline Mass spectrum (API$^+$): Found 427 (MH$^+$). $C_{27}H_{30}N_4O$ requires 426. $^1$H NMR (DMSO-d$_6$) δ: 0.87 (2H, m), 1.02–1.31 (5H, m), 1.63 (4H, m), 2.27 (2H, m), 2.45 (2H, m), 2.64 (2H, m), 3.41 (2H, s), 3.57 (1H, m), 6.26 (1H, d, J=3 Hz), 7.08 (1H, d, J=8 Hz), 7.33 (5H, m), 7.73 (1H, s), 7.88 (1H, d, J=8 Hz), 11.16 (1H, br s).

d1) trans-6-Cyano-2-(2-(1-(4-(2-thieno[3,2-b]thiophenyl) carboxamido)cyclohexyl)-ethyl-1,2,3,4-tetrahydroisoquinoline Mass spectrum (API$^+$): Found 450 (MH$^+$). $C_{25}H_{27}N_3OS_2$ requires 449. $^1$H NMR (DMSO-d$_6$) δ: 0.88 (2H, m), 1.06–1.34 (5H, m), 1.67 (4H, m), 2.34 (2H, m), 2.49 (2H, m), 2.68 (2H, m), 3.45 (2H, s), 2.56 (1H, m), 7.12 (1H, d, J=8 Hz), 7.32 (1H, d, J=5 Hz), 7.41 (2H, m), 7.67 (1H, d, J=5 Hz), 7.95 (1H, s), 8.20 (1H, d, J=8 Hz).

e1) trans-6-Cyano-2-(2-(1-(4-(3,4-methylenedioxy) benzamido)cyclohexyl)ethyl)-1,2,3,4-tetrahydroisoquinoline Mass spectrum (API$^+$): Found 432 (MH$^+$). $C_{26}H^{29}N_3O_3$ requires 431. $^1$H NMR (DMSO-d$_6$) δ: 1.00 (1H, m), 1.08–1.47 (5H, m), 1.78 (4H, m), 2.47 (2H, m), 2.62 (2H, m), 2.81 (2H, m), 3.57 (2H, s), 3.68 (1H, m), 6.05 (2H, s), 6.94 (1H, d, J=8 Hz), 7.25 (1H, d, J=8 Hz), 7.38 (2H, m), 7.56 (2H, m), 7.99 (1H, d, J=8 Hz).

f1) trans-2-(2-(1-(4-(2-Benzofuranyl)carboxamido) cyclohexyl)ethyl)-6-cyano-1,2,3,4-tetrahydroisoquinoline Mass spectrum (API$^+$): Found 428 (MH$^+$). $C_{27}H_{29}N_3O_2$ requires 427. $^1$H NMR (DMSO-d$_6$) δ: 0.84 (2H, m), 1.02–1.32 (5H, m), 1.61 (4H, m), 2.30 (2H, m), 2.46 (2H, m), 2.63 (2H, m), 3.42 (2H, s), 3.55 (1H, m), 7.11 (2H, m), 7.26 (1H, m), 7.39 (4H, m), 7.56 (1H, d, J=8 Hz), 8.30 (1H, d, J=8 Hz).

g1) trans-(E)-6-Cyano-2-(2-(1-(4-(3-(5-(1,2-dihydro-2-oxo)-(3H)-indolyl)propenoyl)amino)cyclohexyl)ethyl-1,2,3,4-tetrahydroisoquinoline Mass spectrum (API$^+$): Found 469 (MH$^+$). $C_{29}H_{32}N_4O_2$ requires 468. $^1$H NMR (DMSO-d$_6$) δ: 0.83–1.18 (5H, m), 1.33 (2H, m), 1.68 (4H, m), 2.38 (2H, m), 2.53 (2H, m), 2.73 (2H, m), 3.40 (2H, s), 3.49 (3H, m), 6.33 (1H, d, J=16 Hz), 6.66 (2H, m), 7.21 (4H, m), 7.48 (2H, m), 7.75 (1H, m).

h1) trans-(E)-6-Cyano-2-(2-(1-(4-(3-phenylpropenoyl) amino)cyclohexyl)ethyl)-1,2,3,4-tetrahydroisoquinoline Mass spectrum (API$^+$): Found 414 (MH$^+$). $C_{27}H_{31}N_3O$ requires 413. $^1$H NMR (DMSO-d$_6$) δ: 0.83–1.22 (5H, m), 1.34 (2H, m), 1.70 (4H, m), 2.38 (2H, m), 2.54 (2H, m), 2.73 (2H, m), 3.50 (3H, m), 6.49 (1H, d, J=16 Hz), 7.17 (1H, d, J=8 Hz), 7.29 (4H, m), 7.45 (4H, m), 7.88 (1H, d, J=8 Hz).

i1) trans-(E)-6-Cyano-2-(2-(1-(4-(3-(4-ethylsulfonyl) phenylpropenoyl)amino)cyclohexyl)ethyl)-1,2,3,4-tetrahydroisoquinoline Mass spectrum (API$^+$): Found 492 (MH$^+$). $C_{28}H_{33}N_3O_3S$ requires 491. $^1$H NMR (DMSO-d$_6$) δ: 0.86–1.26 (5H, m), 1.37 (2H, m), 1.73 (4H, m), 2.40 (2H, m), 2.56 (2H, m), 2.76 (2H, m), 3.16 (3H, s), 3.52 (3H, m), 6.68 (1H, d, J=16 Hz), 7.20 (1H, d, J=8 Hz), 7.40 (1H, d, J=16 Hz), 7.49 (2H, m), 7.72 (2H, d, J=8 Hz), 7.87 (2H, d, J=8 Hz), 8.04 (1H, d, J=8 Hz).

j1) trans-(E)-2-(2-(1-(4-(3-(4-Acetyl)phenylpropenoyl) amino)cyclohexyl)ethyl)-6-cyano-1,2,3,4-tetrahydroisoquinoline Mass spectrum (API$^+$): Found 456 (MH$^+$). $C_{29}H_{33}N_3O_2$ requires 455. $^1$H NMR (DMSO-d$_6$) δ: 0.90–1.28 (5H, m), 1.39 (2H, m), 1.76 (4H, m), 2.42 (2H, m), 2.53 (3H, s), 2.59 (2H, m), 2.78 (2H, m), 3.54 (3H, m), 6.67 (1H, d, J=16 Hz), 7.22 (1H, d, J=8 Hz), 7.40 (1H, d, J=16 Hz), 7.52 (2H, m), 7.62 (2H, d, J=8 Hz), 7.92 (2H, d, J=8 Hz), 8.01 (1H, d, J=8 Hz).

k1) trans-(E)-6-Cyano-2-(2-(1-(4-(3-(3,4-methylenedioxy)phenylpropenoyl)amino)cyclohexyl)ethyl)-1,2,3,4-tetrahydroisoquinoline Mass spectrum (API$^+$): Found 458 (MH$^+$). $C_{28}H_{31}N_3O_3$ requires 457. $^1$H NMR (DMSO-d$_6$) δ: 0.94–1.26 (5H, m), 1.44 (2H, m), 1.81 (4H, m), 2.49 (2H, m), 2.65 (2H, m), 2.85 (2H, m), 3.61 (3H, m), 6.07 (2H, s), 6.44 (1H, d, J=16 Hz), 6.95 (1H, d, J=8 Hz), 7.09 (2H, m), 7.31 (2H, m), 7.58 (2H, m), 7.87 (1H, d, J=8 Hz).

l1) trans-(E)-6-Cyano-2-(2-(1-(4-(3-(3-thienyl)propenoyl)amino)cyclohexyl)ethyl-1,2,3,4-tetrahydroisoquinoline Mass spectrum (API$^+$): Found 420 (MH$^+$). $C_{25}H_{29}N_3OS$ requires 419. $^1$H NMR (DMSO-d$_6$) δ: 0.92–1.25 (5H, m), 1.42 (2H, m), 1.80 (4H, m), 2.48 (2H, m), 2.64 (2H, m), 2.83 (2H, m), 3.59 (3H, m), 6.40 (1H, d, J=16 Hz), 7.29 (2H, m), 7.39 (1H, d, J=16 Hz), 7.50 (3H, m), 7.77 (1H, d, J=3 Hz), 7.91 (1H, d, J=8 Hz).

m1) trans-(E)-6-Cyano-2-(2-(1-(4-(3-(2-thienyl)propenoyl)amino)cyclohexyl)ethyl)-1,2,3,4-tetrahydroisoquinoline Mass spectrum (API$^+$): Found 420 (MH$^+$). $C_{25}H_{29}N_3OS$ requires 419. $^1$H NMR (DMSO-d$_6$) δ: 0.83–1.16 (5H, m), 1.31 (2H, m), 1.69 (4H, m), 2.37 (2H, m), 2.53 (2H, m), 2.73 (2H, m), 3.49 (3H, m), 6.24 (1H, d, J=16 Hz), 6.99 (1H, m), 7.17 (1H, d, J=8 Hz), 7.25 (1H, d, J=3 Hz), 7.44 (4H, m), 7.87 (1H, d, J=8 Hz).

n1) trans-(E)-2-(2-(1-(4-(3-(2-Acetyl)phenylpropenoyl)amino)cyclohexyl)ethyl)-6-cyano-1,2,3,4-tetrahydroisoquinoline Mass spectrum (API$^+$): Found 471 (MH$^+$). $C_{29}H_{34}N_4O_2$ requires 470. $^1$H NMR (DMSO-d$_6$) δ: 0.79–1.14 (5H, m), 1.30 (2H, m), 1.64 (4H, m), 1.92 (3H, s), 2.31 (2H, m ), 2.50 (2H, m), 2.69 (2H, m), 3.45 (3H, m) 6.39 (1H, d, J=16 Hz), 7.03–7.30 (4H, m), 7.42 (4H, m), 7.87 (1H, d, J=8 Hz), 9.61 (1H, s).

o1) trans-(E)-2-(2-(1-(4-(3-(4-Acetyl)phenylpropenoyl)amino)cyclohexyl)ethyl)-6-cyano-1,2,3,4-tetrahydroisoquinoline Mass spectrum (API$^+$): Found 471 (MH$^+$). $C_{29}H_{34}N_4O_2$ requires 470. $^1$H NMR (DMSO-d$_6$) δ: 0.82 (5H, m), 1.33 (2H, m), 1.69 (4H, m), 1.95 (3H, s), 2.37 (2H, m), 2.54 (2H, m), 2.73 (2H, m), 3.49 (3H, m), 6.37 (1H, d, J=16 Hz), 7.20 (2H, m), 7.36 (2H, m), 7.48 (4H, m), 7.83 (1H, d, J=8 Hz), 10.02 (1H, s).

p1) trans-(E)-6-Cyano-2-(2-(1-(4-(3-(4-methoxy)phenylpropenoyl)amino)cyclohexyl)ethyl)-1,2,3,4-tetrahydroisoquinoline Mass spectrum (API$^+$): Found 444 (MH$^+$). $C_{28}H_{33}N_3O_2$ requires 443. $^1$H NMR (DMSO-d$_6$) δ: 1.12–1.43 (5H, m), 1.61 (2H, m), 1.98 (4H, m), 2.67 (2H, m), 2.71 (2H, m), 3.02 (2H, m), 3.78 (3H, m), 3.96 (3H, s), 6.62 (1H, d, J=16 Hz), 7.14 (2H, d, J=8 Hz), 7.50 (2H, m), 7.67 (2H, d, J=8 Hz), 7.75 (2H, m), 8.07 (1H, d, J=8 Hz).

q1) trans-(E)-2-(2-(1-(4-(3-(4-Chloro)phenylpropenoyl)amino)cyclohexyl)ethyl)-6-cyano-1,2,3,4-tetrahydroisoquinoline Mass spectrum (API$^+$): Found 448 (MH$^+$). $C_{27}H_{30}{}^{35}ClN_3O$ requires 447. $^1$H NMR (DMSO-d$_6$) δ: 0.76–1.09 (5H, m), 1.26 (2H, m), 1.63 (4H, m), 2.30 (2H, m), 2.46 (2H, m), 2.66 (2H, m), 3.42 (3H, m), 6.43 (1H, d, J=16 Hz), 7.09 (1H, d, J=8 Hz), 7.2 (1H, d, J=16 Hz), 7.29 (2H, m), 7.37 (4H, m), 7.82 (1H, d, J=8 Hz).

r1) trans-(E)-6-Cyano-2-(2-(1-(4-(3-(3-methylaminocarbonyl)phenylpropenoyl)amino)cyclohexyl)ethyl)-1,3,4-tetrahydroisoquinoline Mass spectrum (API$^+$): Found 471 (MH$^+$). $C_{29}H_{34}N_4O_2$ requires 470. $^1$H NMR (DMSO-d$_6$) δ: 1.09–1.38 (5H, m), 1.58 (2H, m), 1.96 (4H, m), 2.64 (2H, m), 2.79 (2H, m), 2.97 (5H, m), 3.75 (3H, m), 6.85 (1H, d, J=16 Hz), 7.43 (1H, d, J=8 Hz), 7.58 (1H, d, J=16 Hz), 7.69 (3H, m), 7.82 (1H, m), 7.95 (1H, m), 8.20 (2H, m), 8.71 (1H, m).

s1) trans-(E)-6-Cyano-2-(2-(1-(4-(3-(4-methylaminocarbonyl)phenylpropenoyl)amino)cyclohexyl)ethyl)-1,2,3,4-tetrahydroisoquinoline Mass spectrum (API$^+$): Found 471 (MH$^+$). $C_{29}H_{34}N_4O_2$ requires 470. $^1$H NMR (DMSO-d$_6$) δ: 0.79–1.10 (5H, m), 1.25 (2H, m), 1.62 (4H, m), 2.28 (2H, m), 2.45 (2H, m), 2.61 (5H, m), 3.40 (3H, m), 6.49 (1H, d, J=16 Hz), 7.08 (1H, d, J=8 Hz), 7.23 (1H, d, J=16 Hz), 7.40 (4H, m), 7.67 (2H, d, J=8 Hz), 7.85 (1H, m), 8.29 (1H, m).

t1) trans-7-Cyano-2-(2-(1-(4-(6-indolyl)carboxamido)cyclohexyl)ethyl)-1,2,3,4-tetrahydroisoquinoline Mass spectrum (API$^+$): Found 427.2 (MH$^+$). $C_{27}H_{30}N_4O$ requires 426. $^1$H NMR (CDCl$_3$+DMSO-d$_6$) δ: 1.00–1.40 (5H, m), 1.40–1.60 (2H, m), 1.85 (2H, m), 2.06 (2H, m), 2.58 (2H, m), 2.74 (2H, t, J=6 Hz), 2.95 (2H, m), 3.62 (2H, s), 3.91 (1H, m), 6.49 (1H, s), 6.95 (1H, d, J=5.5 Hz), 7.22 (1H, d, J=8 Hz), 7.31 (2H, m), 7.40 (1H, d, J=8 Hz), 7.47 (1H, d, J=8 Hz), 7.58 (1H, d, J=8 Hz), 7.99 (1H, s), 10.64 (1H, s).

u1) trans-2-(2-(1-(4-(2-(5-Chloro)indolyl)carboxamido)cyclohexyl)ethyl)-7-cyano-1,2,3,4-tetrahydroisoquinoline Mass spectrum (API$^+$): Found 461.2 (MH$^+$). $C_{27}H_{29}N_4{}^{35}ClO$ requires 460. $^1$H NMR (CDCl$_3$+DMSO-d$_6$) δ: 1.12 (2H, m), 1.37 (3H, m), 1.51 (2H, m), 1.88 (2H, m), 2.01 (2H, m), 2.58 (2H, m, partially obscured by DMSO), 2.75 (2H, t, J=6 Hz), 2.96 (2H, t, J=6 Hz), 3.63 (2H, s), 3.91 (1H, m), 7.06 (1H, d, J=2 Hz), 7.11 (1H, dd, J=9 and 2 Hz), 7.24 (1H, d, J=8 Hz), 7.40 (2H, m), 7.55 (1H, d, J=2 Hz), 7.76 (2H, m).

v1) trans-7-Cyano-2-(2-(1-(4-(3-thienyl)carboxamido)cyclohexyl)ethyl)-1,2,3,4-tetrahydroisoquinoline Mass spectrum (API$^+$): Found 394 (MH$^+$). $C_{23}H_{27}N_3OS$ requires 393. $^1$H NMR (CDCl$_3$) δ: 1.10–1.40 (5H, m), 1.53 (2H, m), 1.86 (2H, m), 2.08 (2H, m), 2.25 (2H, t, J=8 Hz), 2.73 (2H, J=6 Hz), 2.95 (2H, t, J=6 Hz), 3.62 (2H, s), 3.92 (1H, m), 5.73 (1H, d, J=8 Hz), 7.19 (1H, d, J=8 Hz), 7.34 (3H, m), 7.40 (1H, dd, J=8, 1.5 Hz), 7.82 (1H, dd, J=3, 1.5 Hz).

w1) trans-2-(2-(1-(4-(2-(3-Chloro)benzo[b]thienyl)carboxamido)cyclohexyl)ethyl)-7-cyano-1,2,3,4-tetrahydroisoquinoline Mass spectrum (API$^+$): Found 478 (MH$^+$). $C_{27}H_{28}N_3{}^{35}ClOS$ requires 477. $^1$H NMR (CDCl$_3$) δ: 1.10–1.40 (5H, m), 1.5–1.7 (2H, m), 1.87 (2H, m), 2.18 (2H, m), 2.56 (2H, m), 2.74 (2H, t, J=6 Hz), 2.94 (2H, t, J=6 Hz), 3.62 (2H, s), 3.96 (1H, m), 6.97 (1H, d, J=8 Hz), 7.19 (1H, d, J=8 Hz), 7.33 (1H, s), 7.40 (1H, d, J=8 Hz), 7.50 (2H, m), 7.85 (2H, m).

x1) trans-7-Cyano-2-(2-(1-(4-(6-quinolinyl)carboxamido)cyclohexyl)ethyl)-1,2,3,4-tetrahydroisoquinoline Mass spectrum (API$^+$): Found 439 (MH$^+$). $C_{28}H_{30}N_4O$ requires 438. $^1$H NMR (DMSO-d$_6$) δ: 1.10–1.30 (2H, m), 1.30–1.60 (5H, m), 1.80–2.00 (4H, m), 2.60 (2H, m), 2.75 (2H, m), 2.96 (2H, m), 3.66 (2H, s), 3.89 (1H, m), 7.39 (1H, d, J=8 Hz), 7.6 (3H, m), 8.15 (1H, d, J=8 Hz), 8.26 (1H, dd, J=8, 2 Hz), 8.6 (3H, m), 9.1 (1H, m).

y1) trans-(E)-7-Cyano-2-(2-(1-(4-(3-(2-(3,4-dimethyl)thieno[2,3-b]thiophenyl)propenoyl)amino)cyclohexyl)ethyl)-1,2,3,4-tetrahydroisoquinoline Mass spectrum (API$^+$): Found 504 (MH$^+$). $C_{29}H_{33}N_3OS_2$ requires 503. $^1$H NMR (CDCl$_3$) δ: 1.10–1.40 (5H, m), 1.45–1.55 (2H, m), 1.84 (2H, m), 2.04 (2H, m), 2.48 (3H, s), 2.54 (3H, s), 2.40–2.60 (2H, m), 2.73 (2H, t, J=6 Hz), 2.93 (2H, t, J=6 Hz), 3.61 (2H, s), 3.86 (1H, m), 5.36 (1H, d, J=8 Hz), 6.04 (1H, d, J=15 Hz), 6.87 (1H, s), 7.19 (1H, d, J=8 Hz), 7.33 (1H, s), 7.39 (1H, d, J=8 Hz), 7.88 (1H, d, J=15 Hz).

z1) trans-(E)-7-Cyano-2-(2-(1-(4-(3-(3-methylaminocarbonyl)phenylpropenoyl)amino)cyclohexyl)ethyl-1,2,3,4-tetrahydroisoquinoline Mass spectrum (API$^+$): Found 471 (MH$^+$). $C_{29}H_{34}N_4O_2$ requires 470. $^1$H NMR (CDCl$_3$) δ: 1.20 (5H, m), 1.50 (2H, m), 1.70 (2H, m), 2.04 (2H, m), 2.51 (2H, m), 2.73 (2H, t, J=6 Hz), 2.95 (2H, t, J=6 Hz), 3.02 (3H, d, J=5 Hz), 3.61 (2H, s), 3.86 (1H, m), 5.75 (1H, d, J=8 Hz), 6.41 (1H, d, J=16 Hz), 6.44 (1H, m), 7.18 (1H, d, J=8 Hz), 7.40 (3H, m), 7.55 (2H, m), 7.67 (1H, d, J=8 Hz), 7.91 (1H, s).

a2) trans-(E)-7-Cyano-2-(2-(1-(4-(3-(3-methoxy)phenylpropenoyl)amino)cyclohexyl)ethyl)-1,2,3,4-tetrahydroisoquinoline Mass spectrum (API$^+$): Found 444 (MH$^+$). $C_{28}H_{33}N_3O_2$ requires 443. $^1$H NMR (CDCl$_3$) δ: 1.00–1.40 (5H, m), 1.50 (2H, m), 1.84 (2H, m), 2.05 (2H, m), 2.54 (2H, m), 2.73 (2H, t, J=6 Hz), 2.95 (2H, t, J=6 Hz), 3.61 (2H, s), 3.82 (3H, s), 3.85 (1H, m), 5.49 (H, d, J=8 Hz), 6.34 (1H, d, J=16 Hz), 6.89 (1H, dd, J=8, 2 Hz), 7.01 (1H, m), 7.08 (1H, d, J=8 Hz), 7.19 (1H, d, J=8 Hz), 7.28 (2H, m), 7.40 (1H, m), 7.57 (1H, d, J=15 Hz).

b2) trans-(E)-2-(2-(1-(4-(3-(3-Acetyl)phenypropenoyl)amino)cyclohexyl)ethyl-7-cyano-1,2,3,4-tetrahydroisoquinoline Mass spectrum (API$^+$): Found 456 (MH$^+$). $C_{29}H_{33}N_3O_2$ requires 455. $^1$H NMR (CDCl$_3$) δ: 1.20 (5H, m), 1.51 (2H, m), 1.86 (2H, m), 2.05 (2H, m), 2.54 (2H, m), 2.62 (3H, s), 2.73 (2H, t, J=6 Hz), 2.93 (2H, t, J=6 Hz), 3.61 (2H, s), 3.88 (1H, m), 5.51 (1H, d, J=8 Hz), 6.44 (1H, d, J=16 Hz), 7.18 (1H, d, J=8 Hz), 7.32 (1H, s), 7.43 (2H, m), 7.64 (2H, m), 7.91 (1H, d, J=8 Hz), 8.09 (1H, s).

c2) trans-(E)-2-(2-(1-(4-(3-(3-Chloro)phenylpropenoyl)amino)cyclohexyl)ethyl)-7-cyano-1,2,3,4-tetrahydroisoquinoline Mass spectrum (API$^+$): Found 448 (MH$^+$). $C_{27}H_{30}^{35}ClN_3O$ requires 447. $^1$H NMR (CDCl$_3$) δ: 1.15 (5H, m), 1.50 (2H, m), 1.85 (2H, m), 2.05 (2H, m), 2.53 (2H, m), 2.73 (2H, t, J=6 Hz), 2.95 (2H, t, J=6 Hz), 3.61 (2H, s), 4.10 (1H, m), 5.53 (1H, d, J=8 Hz), 6.36 (1H, d, J=16 Hz), 7.18 (1H, d, J=8 Hz), 7.35 (5H, m), 7.48 (1H, s), 7.54 (1H, d, J=16 Hz).

d2) trans-(E)-7-Cyano-2-(2-(1-(4-(3-(3-thienyl)propenoyl)amino)cyclohexyl)ethyl)-1,2,3,4-tetrahydroisoquinoline Mass spectrum (API$^+$): Found 420 (MH$^+$). $C_{25}H_{29}N_3OS$ requires 419. $^1$H NMR (CDCl$_3$) δ: 1.15 (5H, m), 1.50 (2H, m), 1.84 (2H, m), 2.05 (2H, m), 2.53 (2H, m), 2.72 (2H, t, J=6 Hz), 2.95 (2H, t, J=6 Hz), 3.61 (2H, s), 4.12 (1H, m), 5.47 (1H, d, J=8 Hz), 6.19 (1H, d, J=16 Hz), 7.19 (1H, d, J=6 Hz), 7.28 (3H, m), 7.36 (2H, m), 7.59(1H, d, J=16 Hz).

e2) trans-(E)-2-(2-(1-(4-(3-(2-Acetamido)phenylpropenoyl)amino)cyclohexyl)ethyl)-7-cyano-1,2,3,4-tetrahydroisoquinoline Mass spectrum (API$^+$): Found 471 (MH$^+$). $C_{29}H_{34}N_4O_2$ requires 470. $^1$H NMR (CDCl$_3$) δ: 1.00–1.40 (5H, m), 1.52 (2H, m), 1.85 (4H, m), 2.04 (2H, m), 2.23 (3H, s), 2.54 (2H, m), 2.74 (2H, m), 2.95 (2H, m), 3.61 (2H, s), 3.82 (3H, s), 5.65 (1H, d, J=6 Hz), 6.28 (1H, d, J=16 Hz), 7.21 (1H, m), 7.35 (3H, m), 7.77 (2H, m).

f2) trans-2-(2-(1-(4-Benzamido)cyclohexyl)ethyl)-7-cyano-1,2,3,4-tetrahydroisoquinoline Mass spectrum (API$^+$): Found 388 (MH$^+$). $C_{25}H_{29}N_3O$ requires 387. $^1$H NMR (CDCl$_3$) δ: 1.00–1.45 (5H, m), 1.55 (2H, m), 1.85 (2H, m), 2.10 (2H, m), 2.55 (2H, m), 2.74 (2H, t, J=6 Hz), 2.95 (2H, t, J=6 Hz), 3.61 (2H, s), 4.11 (1H, m), 5.93 (1H, d, J=8 Hz), 7.19 (1H, d, J=8 Hz), 7.33 (1H, s), 7.40 (4H, m), 7.75 (2H, m).

g2) trans-(E)-7-Cyano-2-(2-(1-(4-(3-(2-naphthyl)propenoyl)amino)cyclohexyl)eyhyl)-1,2,3,4-tetrahydroisoquinoline Mass spectrum (API$^+$): Found 464 (MH$^+$). $C_{31}H_{33}N_3O$ requires 463. $^1$H NMR (CDCl$_3$) δ: 1.10–1.40 (5H, m), 1.50 (2H, m), 1.86 (2H, m), 2.08 (2H, m), 2.54 (2H, m), 2.74 (2H, t, J=6 Hz), 2.94 (2H, t, J=6 Hz), 3.62 (2H, s), 3.91 (1H, m), 5.51 (1H, d, J=8 Hz), 6.47 (1H, d, J=16 Hz), 7.18 (1H, d, J=8 Hz), 7.32 (1H, s), 7.40 (1H, d, J=8 Hz), 7.50 (2H, m), 7.36 (1H, d, J=8 Hz), 7.80 (5H, m).

h2) trans-6-Cyano-2-(2-(1-(4-(2-indolyl)carboxamido)cyclohexyl)ethyl)-1,2,3,4-tetrahydroisoquinoline Mass spectrum (API$^+$): Found 427 (MH$^+$). $C_{27}H_{30}N_4O$ requires 426. $^1$H NMR (DMSO-d$_6$) δ: 0.88 (2H, m), 1.03–1.32 (5H, m), 1.60 (4H, m), 2.29 (2H, m), 2.46 (2H, m), 2.65 (2H, m), 3.42 (2H, m), 3.56 (1H, m), 6.82 (1H, m), 6.95 (2H, m), 7.09 (1H, d, J=8 Hz), 7.23 (1H, d, J=8 Hz), 7.38 (3H, m), 8.01 (1H, d, J=8 Hz), 11.34 (1H, s).

i2) trans-(E)-7-Cyano-2-(2-(1-(4-(3-(2-thienyl)propenoyl)amino)cyclohexyl)ethyl)-1,2,3,4-tetrahydroisoquinoline Mass spectrum (API$^+$): Found 420 (MH$^+$). $C_{25}H_{29}N_3OS$ requires 419. $^1$H NMR (CDCl$_3$) δ: 1.04–1.44 (5H, m), 1.54 (2H, m), 1.84 (2H, m), 2.06 (2H, m), 2.54 (2H, m), 2.74 (2H, m), 2.94 (2H, m), 3.63 (3H, s), 3.86 (1H, m), 5.38 (1H, d, J=10 Hz), 6.15 (1H, d, J=16 Hz), 7.04 (1H, m), 7.20 (2H, m), 7.30 (2H, m), 7.41 (1H, dd, J=9, 1 Hz), 7.75 (1H, d, J=16 Hz).

j2) trans-2-(2-(1-(4-(2-Benzo[b]thienyl)carboxamido)cyclohexyl)ethyl)-7-cyano-1,2,3,4-tetrahydroisoquinoline Mass spectrum (API$^+$): Found 444 (MH$^+$). $C_{27}H_{29}N_3OS$ requires 443. $^1$H NMR (CDCl$_3$) δ: 1.05–1.50 (5H, m), 1.53 (2H, m), 1.85 (2H, m), 2.04 (2H, m), 2.55 (2H, m), 2.75 (2H, m), 2.96 (2H, m), 3.64 (2H, s), 3.95 (1H, m), 5.94 (1H, d, J=10 Hz), 7.13–7.52 (6H, m), 7.84 (2H, m).

k2) trans-7-Cyano-2-(2-(1-(4-(6-(pyrrolo[3,2-c]pyridyl)carboxamido)cyclohexyl)eyhyl)-1,2,3,4-tetrahydroisoquinoline Mass spectrum (API$^+$): Found 428 (MH$^+$). $C_{25}H_{29}N_5O$ requires 427. $^1$H NMR (CDCl$_3$+CD$_3$OD) δ: 1.04–1.55 (5H, m), 1.56 (2H, m), 1.89 (2H, m), 2.11 (2H, m), 2.59 (2H, m), 2.78 (2H, t, J=7 Hz), 2.97 (2H, m), 3.65 (2H, s), 3.90 (1H, m), 7.09 (1H, s), 7.25 (1H, d, J=9 Hz), 7.40 (3H, m), 8.25 (1H, d, J=6 Hz), 8.86 (1H, s).

l2) trans-(E)-2-(2-(1-(4-(3-(4-Chloro)phenylpropenoyl)amino)cyclohexyl)ethyl)-7-cyano-1,2,3,4-tetrahydroisoquinoline Mass spectrum (API$^+$): Found 448 (MH$^+$). $C_{27}H_{30}^{35}ClN_3O$ requires 447. $^1$H NMR (CDCl$_3$+CD$_3$OD) δ: 1.05–1.43 (5H, m), 1.53 (2H, m), 1.83 (2H, m), 2.05 (2H, m), 2.55 (2H, m), 2.75 (2H, t, J=7 Hz), 2.98 (2H, m), 3.64 (2H, s), 3.84 (1H, m), 6.13 (1H, m), 6.38 (1H, d, J=16 Hz), 7.24 (1H, d, J=9 Hz), 7.34 (4H, m), 7.42 (3H, m), 7.55 (1H, d, J=16 Hz).

m2) trans-(E)-7-Cyano-2-(2-(1-(4-(3-(3,4-methylenedioxy)phenylpropenoyl)amino)cyclohexyl)ethyl)-1,2,3,4-tetrahydroisoquinoline Mass spectrum (API$^+$): Found 458 (MH$^+$). $C_{28}H_{31}N_3O_3$ requires 457. $^1$H NMR (CDCl$_3$) δ: 1.04–1.42 (5H, m), 1.51 (2H, m), 1.85 (2H, m), 2.09 (2H, m), 2.55 (2H, m), 2.75 (2H, m), 2.96 (2H, m), 3.62 (2H, s), 3.85 (1H, m), 5.50 (1H, d, J=10 Hz), 5.99 (2H, s), 6.19 (1H, d, J=16 Hz), 6.79 (1H, d, J=9 Hz), 6.98 (2H, m), 7.20 (1H, d, J=9 Hz), 7.34 (1H, s), 7.41 (1H, d, J=9 Hz), 7.54 (1H, d, J=16 Hz).

n2) trans-(E)-7-Cyano-2-(2-(1-(4-(3-(5-(1,2-dihydro-2-oxo)-(3H)-indolyl)propenoyl)amino)cyclohexyl)ethyl)-1,2,3,4-tetrahydroisoquinoline Mass spectrum (API+): Found 469 (MH+). $C_{29}H_{32}N_4O_2$ requires 468. $^1$H NMR (DMSO-$d_6$) δ: 0.90–1.38 (5H, m), 1.42 (2H, m), 1.82 (4H, m), 2.47 (2H, m), 2.65 (2H, m), 2.86 (2H, m), 3.45–3.71 (5H, m), 6.46 (1H, d, J=16 Hz), 6.85 (1H, d, J=10 Hz), 7.25–7.47 (3H, m), 7.59 (2H, m), 7.87 (2H, d, J=9 Hz), 10.61 (1H, s).

o2) trams-(E)-2-(2-(1-(4-(3-(3-Acetamido)phenylpropenoyl)amino)cyclohexyl)ethyl)-7-cyano-1,2,3,4-tetrahydroisoquinoline Mass spectrum (API+): Found 471 (MH+). $C_{29}H_{34}N_4O_2$ requires 470. $^1$H NMR (CDCl$_3$+CD$_3$OD) δ: 1.04–1.45 (5H, m), 1.56 (2H, m), 1.85 (2H, m), 2.06 (2H, m), 2.18 (3H, s), 2.59 (2H, m), 2.81 (2H, m), 2.99 (2H, m), 3.66 (2H, s), 3.80 (1H, m), 6.47 (1H, d, J=16 Hz), 6.95 (1H, m), 7.15–7.60 (7H, m), 7.80 (1H, s), 9.24 (1H, br s).

p2) trans-2-(2-(1-(4-(2-Benzo[b]furanyl)carboxamido)cyclohexyl)ethyl)-7-cyano-1,2,3,4-tetrahydroisoquinoline Mass spectrum (API+): Found 428 (MH+). $C_{27}H_{29}N_3O_2$ requires 427. $^1$H NMR (CDCl$_3$) δ: 1.05–1.46 (5H, m), 1.55 (2H, m), 1.89 (2H, m), 2.14 (2H, m), 2.57 (2H, m), 2.75 (2H, t,=7 Hz), 2.95 (2H, m), 3.63 (2H, s), 2.95 (1H, m), 6.45 (1H, d, J=10 Hz), 7.20 (1H, d, J=9 Hz), 7.25–7.55 (6H, m), 7.67 (1H, d, J=9 Hz).

q2) trans-(E)-2-(2-(1-(4-(3-(4-Acetyl)phenylpropenoyl)amino)cyclohexyl)ethyl)-7-cyano-1,2,3,4-tetrahydroisoquinoline Mass spectrum (API+): Found 456 (MH+). $C_{29}H_{33}N_3O_2$ requires 455. $^1$H NMR (DMSO-$d_6$) δ: 1.00–1.40 (5H, m), 1.50–1.60 (2H, m), 1.92 (4H, m), 2.60 (2H, m), 2.69 (3H, s), 2.75 (2H, m), 2.97 (2H, m), 3.66 (2H, s), 3.72 (1H, m), 6.83 (1H, d, J=16 Hz), 7.40 (1H, d, J=8 Hz), 7.55 (1H, d, J=16 Hz), 7.66 (2H, m), 7.95 (2H, d, J=8 Hz), 8.07 (2H, d, J=8 Hz), 8.17 (1H, d, J=8 Hz).

r2) trans-(E)-7-Cyano-2-(2-(1-(4-(3-(4-methylsulfonyl)phenylpropenoyl)amino)cyclohexyl)ethyl)-1,2,3,4-tetrahydroisoquinoline Mass spectrum (API+): Found 492 (MH+). $C_{28}H_{33}N_3O_3S$ requires 491. $^1$H NMR (DMSO-$d_6$) δ: 1.00–1.40 (5H, m), 1.50–1.60 (2H, m), 1.90 (4H, m), 2.60 (2H, m), 2.73 (2H, m), 2.95 (2H, m), 3.32 (3H, s), 3.66 (2H, s), 3.72 (1H, m), 6.84 (1H, d, J=16 Hz), 7.39 (1H, d, J=8 Hz), 7.56 (1H, d, J=16 Hz), 7.66 (2H, m), 7.86 (2H, m), 8.03(2H, d, J=8 Hz), 8.19 (1H, d, J=8 Hz).

s2) trans-(E)-7-Cyano-2-(2-(1-(4-(3-(4-methoxy)phenylpropenoyl)amino)cyclohexyl)ethyl)-1,2,3,4-tetrahydroisoquinoline Mass spectrum (API+): Found 444 (MH+). $C_{28}H_{33}N_3O_2$ requires 443. $^1$H NMR (DMSO-$d_6$) δ: 1.00–1.30 (5H, m), 1.50 (2H, m), 1.80 (4H, m), 2.60 (2H, m), 2.73 (2H, m), 2.94 (2H, m), 3.62 (2H, s), 3.68 (1H, m), 3.85 (3H, s), 6.51 (1H, d, J=16 Hz), 7.04 (2H, d, J=9 Hz), 7.38 (2H, m), 7.56 (2H, d, J=9 Hz), 7.63 (2H, m) 7.95 (1H, d, J=8 Hz).

t2) trans-(E)-7-Cyano-2-(2-(1-(4-(3-(4-methylaminocarbonyl)phenylpropenoyl)amino)cyclohexyl)ethyl)-1,2,3,4-tetrahydroisoquinoline Mass spectrum (API+): Found 469 (MH+). $C_{29}H_{34}N_4O_2$ requires 470. $^1$H NMR (CDCl$_3$+DMSO-$d_6$) δ: 1.10–1.40 (5H, m), 1.60 (2H, m), 1.93 (4H, m), 2.63 (2H, m), 2.77 (2H, m), 2.90 (3H, s), 2.99 (2H, m), 3.68 (2H, s), 3.73 (1H, m), 6.79 (1H, d, J=16 Hz), 7.43 (1H, d, J=8 Hz), 7.48 (1H, d, J=16 Hz), 7.68 (2H, m), 7.74 (2H, d, J=8 Hz), 7.97 (2H, d, J=8 Hz), 8.14 (1H, d, J=8 Hz), 8.60 (1H, m).

u2) trans-7-Cyano-2-(2-(1-(4-(3-quinolinyl)carboxamido)cyclohexyl)ethyl)-1,2,3,4-tetrahydroisoquinoline Mass spectrum (API+): Found 439 (MH+). $C_{28}H_{30}N_4O$ requires 438. $^1$H NMR (DMSO-$d_6$) δ: 1.10–1.30 (3H, m), 1.30–1.60 (4H, m), 1.80–2.10 (4H, m), 2.60 (2H, m), 2.72 (2H, m), 2.94 (2H, m), 3.63 (2H, s), 3.85 (1H, m), 7.37 (1H, d, J=8 Hz), 7.62 (2H, m), 7.74 (1H, t, J=7 Hz), 7.92 (1H, t, J=7 Hz), 8.14 (2H, m), 8.65 (1H, m), 8.86 (1H, s), 9.31 (1H, d, J=2 Hz).

v2) trans-2-(2-(1-(4-(5-Benzimidazolyl)carboxamido)cyclohexyl)ethyl)-7-cyano-1,2,3,4-tetrahydroisoquinoline Mass spectrum (API+): Found 428 (MH+). $C_{26}H_{29}N_5O$ requires 427. $^1$H NMR (DMSO-$d_6$) δ: 1.00–1.20 (2H, m), 1.30–1.60 (5H, m), 1.80–2.00 (4H, m), 2.60 (2H, m), 2.73 (2H, m), 2.95 (2H, m), 3.64 (2H, s), 3.84 (1H, m), 7.38 (1H, d, J=8 Hz), 7.65 (3H, m), 7.79 (1H, dd, J=8, 1.5 Hz), 8.21 (1H, s), 8.23 (1H, d, J=9 Hz), 8.37 (1H, s).

w2) trans-7-Cyano-2-(2-(1-(4-(2-(3-methyl)indolyl)carboxamido)cyclohexyl)ethyl)-1,2,3,4-tetrahydroisoquinoline Mass spectrum (API+): Found 441 (MH+). $C_{28}H_{32}N_4O$ requires 440. $^1$H NMR (DMSO-$d_6$) δ: 1.15–1.35 (2H, m), 1.35–1.65 (5H, m), 1.96 (2H, m), 2.05 (2H, m), 2.60 (5H, m), 2.81 (2H, m), 3.11 (2H, m), 3.69 (2H, s), 3.88 (1H, m), 7.05 (1H, t, J=7 Hz), 7.31 (1H, dt, J=7, 1 Hz), 7.43 (1H, d, J=8 Hz), 7.54 (1H, d, J=8 Hz), 7.69 (3H, m), 7.82 (1H, d, J=8 Hz), 11.20 (1H, s).

x2) trans-7-Cyano-2-(2-(1-(4-(5-(2-methyl)benzimidazolyl)carboxamido)cyclohexyl)ethyl)-1,2,3,4-tetrahydroisoquinoline Mass spectrum (API+): Found 442 (MH+). $C_{27}H_{31}N_5O$ requires 441. $^1$H NMR (CDCl$_3$) δ: 1.13–1.30 (5H, m), 1.52 (2H, m), 1.88 (2H, m), 2.15 (2H, m), 2.56 (2H, m), 2.62 (3H, s), 2.74 (2H, m), 2.95 (2H, m), 3.61 (2H, s), 3.97 (1H, br s), 6.13 (1H, m), 7.19 (1H, d, J=8 Hz), 7.26 (1H, s), 7.33 (1H, s), 7.40 (1H, d, J=8 Hz), 7.68 (2H, br s), 8.06 (1H, s).

y2) trans-6-Cyano-2-(2-(1-(4-(5-(2-methyl)benzimidazolyl)carboxamido)cyclohexyl)ethyl)-1,2,3,4-tetrahydroisoquinoline Mass spectrum (API+): Found 442 (MH+). $C_{27}H_{31}N_5O$ requires 441.

z2) trans-2-(2-(1-(4-(2-(5-Acetyl)indolyl)carboxamido)cyclohexyl)ethyl)-7-cyano-1,2,3,4-tetrahydroisoquinoline Mass spectrum (API+): Found 469 (MH+). $C_{29}H_{32}N_4O_2$ requires 468. $^1$H NMR (DMSO-$d_6$) δ: 1.10–1.30 (2H, m), 1.30–1.70 (5H, m), 2.10 (4H, m), 2.55 (2H, m), 2.74 (3H, s), 2.81 (2H, m), 3.01 (2H, m), 3.71 (2H, s), 3.89 (1H, m), 7.43 (2H, m), 7.60 (1H, d, J=8 Hz), 7.69 (2H, m), 7.93 (1H, dd, J=2, 8 Hz), 8.49 (2H, m), 12.03 (1H, br s).

a3) trans-2-(2-(1-(4-(2-(6-Acetyl)indolyl)carboxamido)cyclohexyl)ethyl)-7-cyano-1,2,3,4-tetrahydroisoquinoline Mass spectrum (API+): Found 469 (MH+). $C_{29}H_{32}N_4O_2$ requires 468. $^1$H NMR (CDCl$_3$): δ: 1.10–1.40 (5H, m), 1.55 (2H, m), 1.90 (2H, m), 2.20 (2H, m), 2.55 (2H, m), 2.67 (3H, s). 2.75 (2H, t, J=6 Hz), 2.96 (2H, t, J=6 Hz), 3.62 (2H, s), 4.05 (1H, m), 6.13 (1H, d, J=8 Hz), 6.86 (1H, d, J=2 Hz), 7.19 (1H, d, J=8 Hz), 7.33 (1H, s), 7.40 (1H, dd, J=2, 8 Hz), 7.67 (1H, m), 7.74 (1H, m), 8.13 (1H, s), 10.20 (1H, br s).

b3) trans-2-(2-(1-(4-(2-(6-Acetyl)indolyl)carboxamido)cyclohexyl)ethyl)-6-cyano-1,2,3,4-tetrahydroisoquinoline Mass spectrum (API+): Found 469 (MH+). $C_{29}H_{32}N_4O_2$ requires 468. $^1$H NMR (DMSO-$d_6$) δ: 0.80–1.50 (7H, m), 1.78 (4H, m), 2.44 (2H, m), 2.53 (3H, s), 2.58 (2H, t, J=6 Hz), 2.76 (2H, m), 3.54 (2H, s), 3.69 (1H, m), 6.00–8.00 (1H, br s), 7.14 (1H, s), 7.21 (1H, d, J=8 Hz), 7.40–7.70 (4H, m), 7.99 (1H, s), 8.31 (1H, d, J=8 Hz).

c3) trans-7-Cyano-2-(2-(1-(4-(2-(6-methylsulfonyl)indolyl)carboxamido)cyclohexyl)ethyl-1,2,3,4-tetrahydroisoquinoline Mass spectrum (API+): Found 505 (MH+). $C_{28}H_{32}N_4O_3S$ requires 504. $^1$H NMR (DMSO-$d_6$) δ: 1.05–1.65 (7H, m), 1.90 (4H, m), 2.55 (2H, m), 2.75 (2H, t, J=6 Hz), 2.97 (2H, t, J=6 Hz), 3.29 (3H, s), 3.66 (2H, s), 3.86 (1H, m), 7.40 (2H, m), 7.65 (3H, m), 7.96 (1H, d, J=8 Hz), 8.08 (1H, s), 8.55 (1H, d, J=8 Hz), 12.32 (1H, br s).

d3) trans-7-Cyano-2-(2-(1-(4-(5-(1-dihydro-2-oxo)-(3H)-indolyl)carboxamido)cyclohexyl)ethyl)-1,2,3,4-tetrahydroisoquinoline Mass spectrum (API+): Found 443 (MH+). $C_{27}H_{30}N_4O_2$ requires 442. $^1$H NMR (CDCl$_3$) δ: 1.13–1.31 (5H, m), 1.52 (2H, m), 1.84 (2H, m), 2.19 (2H, m), 2.52 (2H, m), 2.72 (2H, m), 2.95 (2H, m), 3.56 (2H, s), 3.61 (2H, s), 3.90 (1H, m), 5.78 (1H, d, J=8 Hz), 6.87 (1H, m), 7.18 (1H, m), 7.23 (1H, m), 7.33 (1H, s), 7.40 (1H, m), 7.61 (2H, m).

e3) trans-6-Cyano-2-(2-(1-(4-(5-(1,2-dihydro-2-oxo)-(3H)-indolyl)carboxamido)cyclohexyl)ethyl)-1,2,3,4-tetrahydroisoquinoline Mass spectrum (API+): Found 443 (MH+). $C_{27}H_{30}N_4O_2$ requires 442. $^1$H NMR (CD$_3$OD) δ: 1.00–1.50 (5H, m), 1.59 (2H, m), 1.78–2.12 (4H, m), 2.63 (2H, m), 2.83 (2H, m), 2.98 (2H, m), 3.34 (2H, m), 3.74 (2H, m), 3.86 (1H, m), 4.80 (2H, m), 6.94 (1H, m), 7.28 (1H, m), 7.52 (2H, m), 7.74 (2H, m).

f3) trans-6-Cyano-2-(2-(1-(4-(2-(4-methylthio)indolyl)carboxamido)cyclohexyl)-eyhyl)-1,2,3,4-tetrahydroisoquinoline Mass spectrum (API+): Found 473 (MH+). $C_{28}H_{32}N_4OS$ requires 472. $^1$H NMR (CDCl$_3$) δ: 1.09–1.35 (5H, m), 1.5 (2H, m), 1.85 (2H, m), 2.09 (2H, m), 2.52 (2H, m), 2.56 (3H, s), 2.72 (2H, m), 2.91 (2H, m), 3.62 (2H, s), 3.94 (1H, m), 6.02 (1H, d, J=8 Hz), 6.91 (1H, m), 6.97 (1H, m), 7.12–7.26 (3H, m), 7.33 (1H, s), 7.36 (1H, m), 9.47 (1H, s).

g3) trans-6-Cyano-2-(2-(1-(4-(2-(5-methoxy)indolyl)carboxamido)cyclohexyl)ethyl)-1,2,3,4-tetrahydroisoquinoline Mass spectrum (API+): Found 457 (MH+). $C_{28}H_{32}N_4O_2$ requires 456. $^1$H NMR (DMSO-$d_6$) δ: 1.04 (2H, m), 1.22–1.55 (5H, m), 1.83 (4H, m), 2.49 (2H, m), 2.60 (2H, m), 2.89 (2H, m), 3.75 (6H, m), 6.82 (1H, dd, J=9, 2 Hz), 7.03 (2H, m), 7.30 (2H, d, J=8 Hz), 7.58 (2H, m), 8.16 (1H, d, J=8 Hz), 11.37 (1H, br s).

h3) trans-6-Cyano-2-(2-(1-(4-(2-(5-methylsulfonyl)indolyl)carboxamido)cyclohexyl)ethyl)-1,2,3,4-tetrahydroisoquinoline Mass spectrum (API+): Found 505 (MH+). $C_{28}H_{32}N_4O_3S$ requires 504. $^1$H NMR (DMSO-$d_6$) δ: 1.30 (2H, m), 1.47–1.76 (5H, m), 2.08 (4H, m), 2.74 (2H, m), 2.89 (2H, m), 3.06 (2H, m), 3.40 (3H, s), 3.84 (2H, s), 3.99 (1H, m), 7.52 (2H, m), 7.82 (4H, m), 8.45 (1H, s), 8.65 (1H, d, J=8 Hz), 12.34 (1H, br s).

i3) trans-(E)-6-Cyano-2-(2-(1-(4-(3-(2-indolyl)propenoyl)aminocyclohexyl)ethyl)-1,2,3,4-tetrahydroisoquinoline Mass spectrum (API+): Found 453 (MH+). $C_{29}H_{32}N_4O$ requires 452. $^1$H NMR (DMSO-$d_6$) δ: 0.80–1.13 (5H, m), 1.29 (2H, m), 1.68 (4H, m), 2.32 (2H, m), 2.48 (2H, m), 2.67 (2H, m), 3.43 (2H, s), 3.51 (1H, m), 5.71 (1H, d, J=13 Hz), 6.56 (1H, s), 6.68 (1H, d, J=13 Hz), 6.83 (1H, t, J=7 Hz), 7.00 (1H, t, J=7 Hz), 7.11 (1H, d, J=8 Hz), 7.38 (4H, m), 8.31 (1H, d, J=8 Hz), 12.91 (1H, br s).

j3) trans-(E)-7-Cyano-2-(2-(1-(4-(3-(2-indolyl)propenoyl)amino)cyclohexyl)ethyl)-1,2,3,4-tetrahydroisoquinoline Mass spectrum (API+): Found 453 (MH+). $C_{29}H_{32}N_4O$ requires 452. $^1$H NMR (CDCl$_3$) δ: 1.10–1.39 (5H, m), 1.52 (2H, m), 1.85 (2H, m), 2.10 (2H, m), 2.54 (2H, m), 2.73 (2H, t, J=6 Hz), 2.95 (2H, m), 3.61 (2H, s), 3.83 (1H, m), 5.56 (2H, m), 6.69 (1H, s), 6.77 (1H, d, J=13 Hz), 7.06 (1H, t, J=7 Hz), 7.20 (2H, m), 7.33 (1H, s), 7.43 (2H, m), 7.60 (1H, d, J=8 Hz), 12.51 (1H, br s).

k3) trans-(E)-7-Cyano-2-(2-(1-(4-(3-(3-indolyl)propenoyl)amino)cyclohexyl)ethyl)-1,2,3,4-tetrahydroisoquinoline Mass spectrum (API+): Found 453 (MH+). $C_{29}H_{32}N_4O$ requires 452. $^1$H NMR (DMSO-$d_6$) δ: 0.85–1.50 (7H, m), 1.80 (4H, m), 2.35 (2H, m), 2.61 (2H, m), 2.84 (2H, m), 3.52 (3H, m), 6.56 (1H, d, J=16 Hz), 7.13 (2H, m), 7.27 (1H, d, J=8 Hz), 7.41 (1H, d, J=8 Hz), 7.52 (3H, m), 7.69 (2H, m), 7.84 (1H, m), 11.50 (1H, br s).

l3) trans-2-(2-(1-(4-(2-(7-Acetyl)indolyl)carboxamido)cyclohexyl)ethyl)-7-cyano-1,2,3,4-tetrahydroisoquinoline Mass spectrum (API+): Found 469 (MH+). $C_{29}H_{32}N_4O_2$ requires 468. $^1$H NMR (DMSO-$d_6$) δ: 0.90–1.50 (7H, m), 1.85 (4H, m), 2.46 (2H, m), 2.65 (2H, m), 2.69 (3H, s), 2.87 (2H, m), 3.56 (2H, s), 3.74 (1H, m), 7.22 (1H, d, J=8 Hz), 7.29 (2H, m), 7.55 (2H, m), 8.00 (2H, m), 8.60 (1H, d, J=8 Hz), 10.90 (1H, s).

m3) trans-7-Cyano-2-(2-1-(4-(3-pyridyl)carboxamido)cyclohexyl)ethyl)-1,2,3,4-tetrahydroisoquinoline Mass spectrum (API+): Found 389 (MH+). $C_{24}H_{28}N_4O$ requires 388. $^1$H NMR (DMSO-$d_6$) δ: 0.93–1.68 (7H, m), 1.88 (4H, m), 253 (2H, m), 2.70 (2H, t, J=6 Hz), 2.92 (2H, t, J=6 Hz), 3.61 (2H, s), 4.08 (1H, m), 7.35 (1H, d, J=8 Hz), 7.55 (3H, m), 8.21 (1H, m), 8.45 (1H, d, J=8 Hz), 8.73 (1H, m), 9.03 (1H, d, J=2 Hz).

n3) trans-6-Cyano-2-(2-(1-(4-(2-(6-fluoro)indolyl)carboxamido)cyclohexyl)ethyl)-1,2,3,4-tetrahydroisoquinoline Mass spectrum (API+): Found 445 (MH+). $C_{27}H_{29}FN_4O$ requires 444. $^1$H NMR (DMSO-$d_6$) δ: 1.08 (2H, m), 1.42 (5H, m), 1.84 (4H, m), 2.50 (2H, m), 2.66 (2H, t, J=6 Hz), 2.84 (2H, m), 3.61 (2H, s), 3.73 (1H, m), 6.90 (1H, m), 7.15 (2H, m), 7.27 (1H, d, J=8 Hz), 7.61 (3H, m), 8.21 (1H, d, J=8 Hz), 11.6 (1H, s).

o3) trans-6-Cyano-2-(2-(1-(4-(2-(6-methoxy)indolyl)carboxamido)cyclohexyl)ethyl)-1,2,3,4-tetrahydroisoquinoline Mass spectrum (API+): Found 457 (MH+). $C_{28}H_{32}N_4O_2$ requires 456. $^1$H NMR (DMSO-$d_6$) δ: 1.11 (2H, m), 1.37 (5H, m), 1.85 (4H, m), 2.54 (2H, m), 2.69 (2H, t, J=6 Hz), 2.88 (2H, t, J=6 Hz), 3.65 (2H, s), 3.80 (3H, s), 3.75–3.90 (1H, m), 6.72 (1H, dd, J=2, 8 Hz), 6.94 (1H, d, J=2 Hz), 7.11 (1H, m), 7.32 (1H, d, J=8 Hz), 7.49 (1H, d, J=8 Hz), 7.62 (2H, m), 8.10 (1H, d, J=8 Hz), 11.35 (1H, s).

p3) trans-6-Cyano-2-(2-(1-(4-(2-(6-methyl)indolyl)carboxamido)cyclohexyl)ethyl)-1,2,3,4-tetrahydroisoquinoline Mass spectrum (API+): Found 441 (MH+). $C_{28}H_{32}N_4O$ requires 440. $^1$H NMR (DMSO-$d_6$) δ: 1.13 (2H, m), 1.42 (5H, m), 1.90 (4H, m), 2.43 (3H, m), 2.54 (2H, m), 2.70 (2H, t, J=6 Hz), 2.90 (2H, t, J=6 Hz), 3.65 (2H, s), 3.80 (1H, m), 6.90 (1H, m), 7.12 (1H, m), 7.25 (1H, s), 7.33 (1H, d, J=8 Hz), 7.52 (1H, d, J=8 Hz), 7.63 (2H, m), 8.20 (1H, d, J=8 Hz), 11.4 (1H, s).

q3) trans-2-(2-(1-(4-(2-(7-Acetyl)indolyl)carboxamido)cyclohexyl)ethyl)-6-cyano-1,2,3,4-tetrahydroisoquinoline Mass spectrum (API+): Found 469 (MH+). $C_{29}H_{32}N_4O_2$ requires 468. $^1$H NMR (DMSO-$d_6$) δ: 1.10 (2H, m), 1.39 (5H, m), 1.87 (4H, m), 2.50 (2H, m), 2.67 (2H, t, J=6 Hz), 2.71 (3H, s), 2.86 (2H, t, J=6 Hz), 3.63 (2H, s), 3.77 (1H, m), 7.29 (3H, m), 7.59 (2H, m), 8.00 (2H, m), 8.63 (1H, d, J=8 Hz), 10.93 (1H, s).

r3) trans-7-Cyano-2-(2-(1-(4-(2-(5-cyano)indolyl)carboxamido)cyclohexyl)ethyl)-1,2,3,4-tetrahydroisoquinoline Mass spectrum (API$^+$): Found 452 (MH$^+$). $C_{28}H_{29}N_5O$ requires 451. $^1$H NMR (DMSO-d$_6$) δ: 1.10 (2H, m), 1.39 (5H, m), 1.85 (4H, m), 2.51 (2H, m), 2.67 (2H, t, J=6 Hz), 2.85 (2H, m), 3.65 (2H, s), 3.77 (1H, m), 7.28 (2H, m), 7.53 (4H, m), 8.25 (1H, m), 8.45 (1H, d, J=8 Hz), 12.14 (1H, s).

s3) trans-6-Cyano-2-(2-(1-(4-(2-(5-cyano)indolyl)carboxamido)cyclohexyl)ethyl)-1,2,3,4-tetrahydroisoquinoline Mass spectrum (API$^+$): Found 452 (MH$^+$). $C_{28}H_{29}N_5O$ requires 451. $^1$H NMR (DMSO-d$_6$) δ: 1.12 (2H, m), 1.41 (5H, m), 1.89 (4H, m), 2.51 (2H, m), 2.70 (2H, t, J=6 Hz), 2.92 (2H, m), 3.61 (2H, s), 3.82 (1H, m), 7.35 (2H, m), 7.55 (4H, m), (8.28 (1H, m), 8.47 (1H, d, J=8 Hz), 12.17 (1H, s).

t3) trans-7-Cyano-2-(2-(1-(4-(2-(7-cyano)indolyl)carboxamido)cyclohexyl)ethyl)-1,2,3,4-tetrahydroisoquinoline Mass spectrum (API$^+$): Found 452 (MH$^+$). $C_{28}H_{29}N_5O$ requires 451. $^1$H NMR (DMSO-d$_6$) δ: 1.08 (2H, m), 1.36 (5H, m), 1.86 (4H, m), 2.47 (2H, m), 2.65 (2H, t, J=6 Hz), 2.84 (2H, m), 3.61 (2H, s), 3.74 (1H, m), 7.23 (3H, m), 7.57 (2H, m), 7.71 (1H, d, J=8 Hz), 8.00 (1H, d, J=8 Hz), 8.33 (1H, d, J=8 Hz), 12.28 (1H, s).

u3) trans-6-Cyano-2-(2-(1-(4-(2-(7-cyano)indolyl)carboxamido)cyclohexyl)ethyl)-1,2,3,4-tetrahydroisoquinoline Mass spectrum (API$^+$): Found 452 (MH$^+$). $C_{28}H_{29}N_5O$ requires 451. $^1$H NMR (DMSO-d$_6$) δ: 1.00–1.55 (7H, m), 1.70–2.05 (4H, m), 2.50 (2H, m), 2.68 (2H, t, J=6 Hz), 2.90 (2H, t, J=6 Hz), 3.59 (2H, s), 3.76 (1H, m), 7.28 (3H, m), 7.58 (2H, m), 7.73 (1H, d, J=8 Hz), 8.01 (1H, d, J=8 Hz), 8.35 (1H, d, J=8 Hz), 12.24 (1H, s).

v3) trans-5-Cyano-2-(2-(1-(4-(2-indolyl)carboxamido)cyclohexyl)ethyl)-1,2,3,4-tetrahydroisoquinoline Mass spectrum (API$^+$): Found 427 (MH$^+$). $C_{27}H_{30}N_4O$ requires 426. $^1$H NMR (DMSO-d$_6$+TFA) δ: 1.14 (2H, m), 1.39 (3H, m), 1.70 (2H, m), 1.89 (4H, m), 3.00–3.55 (5H, m), 3.80 (2H, m), 4.38 (1H, m), 4.70 (1H, m), 7.03 (1H, t, J=9 Hz), 7.17 (2H, m), 7.37–7.64 (4H, m), 7.85 (1H, dd, J=9, 1 Hz), 8.24 (1H, d, J=9 Hz), 10.30 (1H, br s), 11.53 (1H, br s).

w3) trans-(E)-5-Cyano-2-(2-(1-(4-(3-phenylpropenoyl)amino)cyclohexyl)ethyl)-1,2,3,4-tetrahydroisoquinoline Mass spectrum (API$^+$): Found 414 (MH$^+$). $C_{27}H_{31}N_3O$ requires 413. $^1$H NMR (CDCl$_3$) δ: 1.03–1.42 (5H, m), 1.52 (2H, m), 1.82 (2H, m), 2.07 (2H, m), 2.54 (2H, m), 2.75 (2H, t, J=7 Hz), 3.05 (2H, m), 3.60 (2H, s), 3.87 (1H, m), 5.55 (1H, d, J=10 Hz), 6.35 (1H, d, J=16 Hz), 7.21 (2H, m), 7.33 (3H, m), 7.47 (3H, m), 7.61 (1H, d, J=16 Hz).

x3) trans-7-Cyano-2-(2-(1-(4-(2-(4-methylsulfonyl)indolyl)carboxamido)cyclohexyl)ethyl)-1,2,3,4-tetrahydroisoquinoline Mass spectrum (API$^+$): Found 505 (MH$^+$). $C_{28}H_{32}N_4O_3S$ requires 504. $^1$H NMR (CDCl$_3$) δ: 1.06–1.35 (5H, m), 1.48 (2H, m), 1.80 (2H, m), 1.98 (2H, m), 2.50 (2H, m), 2.71 (2H, m), 2.91 (2H, m), 3.10 (3H, m), 3.58 (2H, s), 3.84 (1H, br s), 6.10 (1H, d, J=8 Hz), 7.18 (1H, d, J=9 Hz), 7.26–7.40 (5H, m), 7.70 (2H, d, J=8 Hz).

y3) (±)-trans-7-Cyano-2-(2-(1-(4-(2-(4-methylsulfinyl)indolyl)carboxamido)cyclohexyl)ethyl)-1,2,3,4-tetrahydroisoquinoline Mass spectrum (API$^+$): Found 489 (MH$^+$). $C_{28}H_{32}N_4O_2S$ requires 488. $^1$H NMR (CDCl$_3$) δ: 1.09–1.38 (5H, m), 1.49–1.59 (2H, m), 1.69–1.96 (4H, m), 2.1 (2H, m), 2.57 (2H, m), 2.75 (2H, m), 2.90 (3H, m), 2.98 (2H, m), 3.60 (2H, m), 3.95 (1H, m), 6.36 (1H, d, J=8 Hz), 7.20 (1H, d, J=8 Hz), 7.25–7.50 (4H, m), 7.42 (1H, s), 7.59 (1H, d, J=8 Hz), 10.14 (1H, s).

z3) trans-7-Cyano-2-(2-(1-(4-(4-pyridyl)carboxamido)cyclohexyl)ethyl)-1,2,3,4-tetrahydroisoquinoline Mass spectrum (API$^+$): Found 389 (MH$_+$). $C_{24}H_{28}N_4O$ requires 388. $^1$H NMR (CDCl$_3$) δ: 1.13–1.34 (5H, m), 1.52 (2H, m), 1.85 (2H, m), 2.09 (2H, m), 2.55 (2H, m), 2.74 (2H, t, J=6 Hz), 2.95 (2H, t, J=6 Hz), 3.62 (2H, s), 3.87 (1H, m), 6.06 (1H, m), 7.19 (1H, d, J=8 Hz), 7.34 (1H, d, J=1Hz), 7.39 (1H, dd, J=1, 8 Hz), 7.6 (2H, d, J=6 Hz), 8.72 (2H, d, J=6 Hz).

a4) trans-7-Cyano-2-(2-(1-(4-(4-quinolinyl)carboxamido)cyclohexyl)ethyl)-1,2,3,4-tetrahydroisoquinoline Mass spectrum (API$^+$): Found 439 (MH$^+$). $C_{28}H_{30}N_4O$ requires 438. $^1$H NMR (CDCl$_3$) δ: 1.18–1.32 (5H, m), 1.55 (2H, m), 1.90 (2H, m), 2.20 (2H, m), 2.56 (2H, m), 2.74 (2H, t, J=6 Hz), 2.96 (2H, t, J=6 Hz), 3.62 (2H, s), 4.10 (1H, m), 5.88 (1H, d, J=8 Hz), 7.20 (1H, d, J=8 Hz), 7.33 (1H, s), 7.40 (2H, m), 7.61 (1H, m), 7.77 (1H, m), 8.15 (2H, m), 8.93 (1H, d, J=4 Hz).

b4) trans-6-Cyano-2-(2-(1-(4-(4-quinolinyl)carboxamido)cyclohexyl)ethyl)-1,2,3,4-tetrahydroisoquinoline Mass spectrum (API$^+$): Found 439 (MH$^+$). $C_{28}H_{30}N_4O$ requires 438. $^1$H NMR (CDCl$_3$) δ: 1.17–1.32 (5H, m), 1.55 (2H, m), 1.89 (2H, m), 2.19 (2H, m), 2.56 (2H, m), 2.74 (2H, t, J=6 Hz), 2.93 (2H, t, J=6 Hz), 3.66 (2H, s), 4.10 (1H, m), 5.95 (1H, m), 7.13 (1H, d, J=8 Hz), 7.39 (3H, m), 7.61 (1H, m), 7.76 (1H, m), 8.12–8.21 (2H, m), 8.92 (1H, m).

c4) trans-(E)-6-Cyano-2-(2-(1-(4-(3-(2-fluoro)phenylpropenoyl)amino)cyclohexyl)ethyl)-1,2,3,4-tetrahydroisoquinoline Mass spectrum (API$^+$): Found 432 (MH$^+$). $C_{27}H_{30}FN_3O$ requires 431. $^1$H NMR (CDCl$_3$) δ: 1.00–1.45 (5H, m), 1.50 (2H, m), 1.80 (2H, m), 2.05 (2H, m), 2.55 (2H, m), 2.72 (2H, t, J=6 Hz), 2.92 (2H, t, J=6 Hz), 3.61 (2H, s), 3.69 (1H, m), 5.53 (1H, d, J=8 Hz), 6.50 (1H, d, J=16 Hz), 7.00–7.20 (3H, m), 7.25–7.55 (4H, m), 7.66 (1H, d, J=16 Hz).

d4) trans-(E)-6-Cyano-2-(2-(1-(4-(3-(2-methoxy)phenylpropenoyl)amino)cyclohexyl)ethyl)-1,2,3,4-tetrahydroisoquinoline Mass spectrum (API$^+$): Found 444 (MH$^+$). $C_{28}H_{33}N_3O_2$ requires 443. $^1$H NMR (CDCl$_3$) δ: 1.05–1.40 (5H, m), 1.50 (2H, m), 1.80 (2H, m), 2.05 (2H, m), 2.54 (2H, m), 2.72 (2H, t, J=6 Hz), 2.92 (2H, t, J=6 Hz), 3.64 (2H, s), 3.75–4.0 (1H, m), 3.87 (3H, s), 5.46 (1H, d, J=8 Hz), 6.48 (1H, d, J=16 Hz), 6.91 (2H, m), 7.11 (1H, d, J=8 Hz), 7.25–7.40 (3H, m), 7.45 (1H, dd, J=8, 2 Hz), 7.83 (1H, d, J=16 Hz).

e4) trans-(E)-2-(2-(1-(4-(3-(2-Chloro)phenylpropenoyl)amino)cyclohexyl)ethyl)-6-cyano-1,2,3,4-tetrahydroisoquinoline Mass spectrum (API$^+$): Found 448 (MH$^+$). $C_{27}H_{30}{}^{35}ClN_3O$ requires 447. $^1$H NMR (CDCl$_3$) δ: 1.05–1.45 (5H, m), 1.50 (2H, m), 1.80 (2H, m), 2.05 (2H, m), 2.54 (2H, m), 2.72 (2H, t, J=6 Hz), 2.90 (2H, t, J=6 Hz), 3.64 (2H, s), 3.89 (1H, m), 5.53 (1H, d, J=8 Hz), 6.36 (1H, d, J=16 Hz), 7.11 (1H, d, J=8 Hz), 7.25 (2H, m), 7.40 (3H, m), 7.55 (1H, m), 7.95 (1H, d, J=16 Hz).

f4) trans-(E)-6-Cyano-2-(2-(1-(4-(3-(2-methyl)phenylpropenoyl)amino)cyclohexyl)ethyl)-1,2,3,4-tetrahydroisoquinoline Mass spectrum (API$^+$): Found 428 (MH$^+$). $C_{28}H_{33}N_3O$ requires 427. $^1$H NMR (CDCl$_3$) δ: 1.05–1.45 (5H, m), 1.53 (2H, m), 1.85 (2H, m), 2.10 (2H, m), 2.43 (3H, s), 2.53 (2H, m), 2.73 (2H, t, J=6 Hz), 2.92 (2H, t, J=6 Hz), 3.61 (2H, s), 3.89 (1H, m), 5.48 (1H, d, J=8 Hz), 6.25 (1H, d, J=16 Hz), 7.05–7.30 (4H, m), 7.38 (2H, m), 7.48 (1H, m), 7.89(1H, d, J=16 Hz).

g4) trans-(E)-6-Cyano-2-(2-(1-(4-(3-(3-fluoro)phenylpropenoyl)amino)cyclohexyl)ethyl)-1,2,3,4-tetrahydroisoquinoline Mass spectrum (API$^+$): Found 432 (MH$^+$). $C_{27}H_{30}FN_3O$ requires 431. $^1$H NMR (CDCl$_3$) δ: 1.05 –1.45 (5H, m), 1.50 (2H, m), 1.81 (2H, m), 2.05 (2H, m), 2.54 (2H, m), 2.73 (2H, t, J=6 Hz), 2.92 (2H, t, J=6 Hz), 3.64 (2H, s), 3.87 (1H, m), 5.56 (1H, d, J=8 Hz), 6.35 (1H, d, J=16 Hz), 6.95–7.45 (7H, m), 7.56 (1H, d, J=16 Hz).

h4) trans-(E)-6-Cyano-2-(2-(1-(4-(3-(2,6-difluoro)phenylpropenoyl)amino)cyclohexyl)ethyl)-1,2,3,4-tetrahydroisoquinoline Mass spectrum (API$^+$): Found 450 (MH$^+$). $C_{27}H_{29}F_2N_3O$ requires 449. $^1$H NMR (CDCl$_3$+CD$_3$OD) δ: 1.03–1.42 (5H, m), 1.53 (2H, m), 1.82 (2H, m), 2.05 (2H, m), 2.55 (2H, m), 2.75 (2H, t, J=6 Hz), 2.94 (2H, t, J=6 Hz), 3.66 (2H, s), 3.84 (1H, m), 6.19 (1H, br s), 6.70 (1H, d, J=16 Hz), 6.93 (2H, t, J=8 Hz), 7.14 (1H, d, J=8 Hz), 7.28 (1H, m), 7.40 (2H, m), 7.69 (1H, d, J=16 Hz).

i4) trans-(E)-6-Cyano-2-(2-(1-(4-(3-(2,3-methylenedioxy)phenylpropenoyl)amino)cyclohexyl)ethyl)-1,2,3,4-tetrahydroisoquinoline Mass spectrum (API$^+$): Found 458 (MH$^+$). $C_{28}H_{31}N_3O_3$ requires 457. $^1$H NMR (CDCl$_3$+CD$_3$OD) δ: 1.02–1.42 (5H, m), 1.52 (2H, m), 1.83 (2H, m), 2.02 (2H, m), 2.56 (2H, m), 2.77 (2H, t, J=6 Hz), 2.94 (2H, t, J=6 Hz), 3.69 (2H, s), 3.91 (1H, m), 6.14 (2H, s), 6.68 (1H, d, J=16 Hz), 6.83 (2H, m), 6.93 (1H, m), 7.16 (1H, d, J=8 Hz), 7.40 (1H, d, J=8 Hz), 7.44 (1H, s), 7.49 (1H, d, J=16 Hz).

j4) trans-(E)-6-Cyano-2-(2-(1-(4-(3-(2,3-difluoro)phenylpropenoyl)amino)cyclohexyl)ethyl)-1,2,3,4-tetrahydroisoquinoline Mass spectrum (API$^+$): Found 450 (MH$^+$). $C_{27}H_{29}F_2N_3O$ requires 449. $^1$H NMR (CDCl$_3$) δ: 1.05–1.45 (1H, m), 1.52 (2H, m), 1.80 (2H, m), 2.05 (2H, m), 2.54 (2H, m), 2.73 (2H, t, J=6 Hz), 2.92 (2H t, J=6 Hz), 3.64 (2H, s), 3.87 (1H, m), 5.56 (1H, d, J=8 Hz), 6.52 (1H, d, J=16 Hz), 6.95–7.30 (4H, m), 7.39 (2H, m), 7.63 (1H, d, J=16 Hz).

k4) trans-2-(2-(1-(4-(4-Quinolinyl)carboxamide)cyclohexyl)ethyl)-6-trifluoromethyl-1,2,3,4-tetrahydroisoquinoline Mass spectrum (API$^+$): Found 482 (MH$^+$). $C_{28}H_{30}F_3N_3O$ requires 481. $^1$H NMR (CDCl$_3$) δ: 1.10–1.43 (5H, m), 1.54 (2H, m), 1.89 (2H, m), 2.20 (2H, m), 2.56 (2H, m), 2.75 (2H, t, J=6 Hz), 2.95 (2H, m), 3.66 (2H, s), 4.06 (1H, m), 5.88 (1H, d, J=8 Hz), 7.13 (1H, d, J=8 Hz), 7.36 (2H, m), 7.41 (1H, m), 7.61 (1H, m), 7.77 (1H, m), 8.17 (2H, m), 8.92 (1H, d, J=4 Hz).

l4) trans-2-(2-(1-(4-(4-Quinolinyl)carboxamido)cyclohexyl)ethyl)-6-trifluoromethoxy)-1,2,3,4-tetrahydroisoquinoline Mass spectrum (API$^+$): Found 498 (MH$^+$). $C_{28}H_{30}F_3N_3O_2$ requires 497. $^1$H NMR (CDCl$_3$) δ: 1.09–1.37 (5H, m), 1.54 (2H, m), 1.89 (2H, m), 2.20 (2H, m), 2.55 (2H, m), 2.72 (2H, t, J=6 Hz), 2.92 (2H, m), 3.60 (2H, s), 4.04 (1H, m), 5.87 (1H, d, J=8 Hz), 7.01 (3H, m), 7.41 (1H, d, J=4 Hz), 7.61 (1H, m), 7.76 (1H, m), 8.15 (2H, m), 8.93 (1H, d, J=4 Hz).

m4) trans-(E)-6-Cyano-2-(2-(1-(4-(3-(3-methylsulfonyloxy)phenylpropenoyl)amino)cyclohexyl)ethyl)-1,2,3,4-tetrahydroisoquinoline Mass spectrum (API$^+$): Found 508 (MH$^+$). $C_{28}H^{33}N_3O_4S$ requires 507. $^1$H NMR (CDCl$_3$) δ: 1.00–1.40 (5H, m), 1.52 (2H, m), 1.53 (2H, m), 2.05 (2H, m), 2.55 (2H, m), 2.73 (2H, t, J=6 Hz), 2.92 (2H, t, J=6 Hz), 3.17 (3H, s), 3.64 (2H, m), 3.85 (1H, m), 5.75 (1H, d, J=16 Hz), 6.39 (1H, d, J=16 Hz), 7.12 (1H, d, J=8 Hz), 7.25 (1H, m), 7.4 (5H, m), 7.56 (1H, d, J=16 Hz).

n4) trans-(E)-2-(2-(1-(4-(3-(7-Benzo[b]furanyl)propenoyl)amino)cyclohexyl)ethyl)-6-cyano-1,2,3,4-tetrahydroisoquinoline Mass spectrum (API$^+$): Found 454 (MH$^+$). $C_{29}H_{31}N_3O_2$ requires 453. $^1$H NMR (CDCl$_3$) δ: 1.09–1.30 (5H, m), 1.51 (2H, m), 1.85 (2H, m), 2.09 (2H, m), 2.55 (2H, m), 2.73 (2H, t, J=6 Hz), 2.92 (2H, m), 3.65 (2H, s), 3.90 (1H, m), 5.52 (1H, d, J=8 Hz), 6.82 (1H, d, J=2 Hz), 7.00 (1H, d, J=16 Hz), 7.11 (1H, d, J=8 Hz), 7.26 (1H, m), 7.39 (3H, m), 7.59 (1H, dd, J=8, 2 Hz), 7.69 (1H, d, J=2 Hz), 7.76 (1H, d, J=16 Hz).

o4) trans-6-Cyano-2-(2-(1-(4-(4-(6-methoxy)quinolinyl)carboxamido)cyclohexyl)ethyl)-1,2,3,4-tetrahydroisoquinoline Mass spectrum (API$^+$): Found 469 (MH$^+$). $C_{29}H_{32}N_4O_2$ requires 468. $^1$H NMR (CDCl$_3$) δ: 1.10–1.40 (5H, m), 1.50–1.60 (2H, m), 1.80–1.90 (2H, m), 2.10–2.20 (2H, m), 2.56 (2H, t, J=8 Hz), 2.74 (2H, t, J=6 Hz), 2.93 (2H, t, J=6 Hz), 3.65 (2H, s), 3.93 (3H, s), 4.00–4.10 (1H, m), 5.95 (1H, d, J=8 Hz), 7.10 (1H, d, J=8 Hz), 7.30–7.40 (4H, m), 7.50 (1H, d, J=2.5 Hz), 8.00 (1H, d, J=5 Hz), 8.75 (1H, d, J=5 Hz).

p4) trans-(E)-6-Cyano-2-(2-(1-(4-(3-(1-naphthyl)propenoyl)amino)cyclohexyl)ethyl)-1,2,3,4-tetrahydroisoqinoline Mass spectrum (API$^+$): Found 464 (MH$^+$). $C_{31}H_{33}N_3O$ requires 463. $^1$H NMR (CDCl$_3$) δ: 1.10–1.45 (5H, m), 1.53 (2H, m), 1.85 (2H, m), 2.07 (2H, m), 2.55 (2H, m), 2.75 (2H, t, J=6 Hz), 2.93 (2H, t, J=6 Hz), 3.65 (2H, s), 3.90 (1H, m), 5.49 (1H, d, J=8 Hz), 6.42 (1H, d, J=15 Hz), 7.11 (1H, d, J=8 Hz), 7.35–7.65 (5H, m), 7.67 (1H, d, J=7 Hz), 7.86 (2H, m), 8.21 (1H, m), 8.43 (1H, d, J=15 Hz).

q4) trans-2-(2-(1-(4-(4-Quinolinyl)carboxamido)cyclohexyl)ethyl)-5-trifluoromethyl-1,2,3,4-tetrahydroisoquinoline Mass spectrum (API$^+$): Found 482 (MH$^+$). $C_{28}H_{30}F_3N_3O$ requires 481. $^1$H NMR (DMSO-d$_6$) δ: 1.10–1.42 (5H, m), 1.50 (2H, m), 1.85 (2H, m), 1.99 (2H, m), 2.52 (2H, m), 2.71 (2H, m), 2.95 (2H, m), 3.65 (2H, s), 3.83 (1H, m), 7.38 (2H, m), 7.54 (2H, m), 7.69 (1H, m), 7.83 (1H, m), 8.11 (2H, m), 8.68 (1H, d, J=8 Hz), 8.98 (1H, d, J=4 Hz).

r4) trans-(E)-2-(2-(1-(4-(3-(3-Cyano)phenylpropenoyl)amino)cyclohexyl)ethyl)-5-trifluoromethyl-1,2,3,4-tetrahydroisoquinoline Mass spectrum (API$^+$): Found 482 (MH$^+$). $C_{28}H_{30}F_3N^3O$ requires 481. $^1$H NMR (DMSO-d$_6$) δ: 0.99–1.37 (5H, m), 1.51 (2H, m), 1.88 (4H, m), 2.56 (2H, m), 2.72 (2H, m), 2.99 (2H, m), 3.68 (3H, m), 6.78 (1H, d, J=16 Hz), 7.41 (2H, m), 7.51 (1H, d, J=15 Hz), 7.59 (1H, m), 7.69 (1H, t, J=8 Hz), 7.90 (2H, m), 8.09 (2H, m), s4) trans-(E)-2-(2-(1-(4-(3-Phenylpropenoyl)amino)cyclohexyl)ethyl)-5-trifluoromethyl-1,2,3,4-tetrahydroisoquinoline Mass spectrum (API$^+$): Found 457 (MH$^+$). $C_{27}H_{31}F_3N_2O$ requires 456. $^1$H NMR (DMSO-d$_6$) δ: 1.00–1.34 (5H, m), 1.49 (2H, m), 1.88 (4H, m), 2.52 (2H, m), 2.73 (2H, m), 2.98 (2H, m), 3.67 (3H, m), 6.68 (1H, d, J=16 Hz), 7.44 (6H, m), 7.60 (3H, m), 8.06 (1H, d, J=8 Hz).

t4) trans-(E)-2-(2-(1-(4-(3-(3-Acetamido)phenylpropenoyl)amino)cyclohexyl-3-ethyl)-5-trifluoromethyl-1,2,3,4-tetrahydrosioquinoline Mass spectrum (API$^+$): Found 514 (MH$^+$). $C_{29}H_{34}F_3N_3O_2$ requires 513. $^1$H NMR (DMSO-d$_6$) δ: 1.00–1.30 (5H, m), 1.47 (2H, m), 1.83 (4H, m), 2.08 (3H, s), 2.51 (2H, m), 2.69 (2H, m), 2.94 (2H, m), 3.63 (3H, m), 6.58 (1H, d, J=16 Hz), 7.22 (1H, m), 7.37 (4H, m), 7.50 (2H, m), 7.95 (1H, m), 8.11 (1H, d, J=8 Hz), 10.11 (1H, br s).

u4) trans-(E)-6-Cyano-2-(2-(1-(4-(3-(4-quinolinyl)propenoyl)amino)cyclohexyl)ethyl)-1,2,3,4-tetrahydroisoquinoline Mass spectrum (API$^+$): Found 465 (MH$^+$). C$_{30}$H$_{32}$N$_4$O requires 464. $^1$H NMR (DMSO-d$_6$) δ: 1.00–1.35 (5H, m), 1.45 (2H, m), 1.85 (4H, m), 2.54 (2H, m), 2.65 (2H, m), 2.85 (2H, m), 3.60 (2H, s), 3.65 (1H, m), 6.85 (1H, d, J=16 Hz), 7.30 (1H, d, J=8 Hz), 7.60 (2H, m), 7.70 (2H, m), 7.85 (1H, m), 8.08 (1H, m), 8.15 (1H, d, J=16 Hz), 8.25 (2H, m), 8.95 (1H, d, J=4 Hz).

v4) trans-5,6-Difluoro-2-(2-(1-(4-(4-quinolinyl)carboxamido)cyclohexyl)ethyl-1,2,3,4-tetrahydroisoquinoline Mass spectrum (API$^+$): Found 450 (MH$^+$). C$_{27}$H$_{29}$F$_2$N$_3$O requires 449. $^1$H NMR (CDCl$_3$) δ: 1.12–1.36 (5H, m), 1.54 (2H, m), 1.89 (2H, m), 2.18 (2H, m), 2.52 (2H, m), 2.69 (2H, t, J=8 Hz), 2.86 (2H, m), 3.56 (2H, s), 4.05 (1H, m), 5.92 (1H, d, J=8 Hz), 6.75 (1H, m), 6.93 (1H, m), 7.40 (1H, d, J=4 Hz), 7.59 (1H, m), 7.75 (1H, m), 8.15 (2H, m), 8.91 (1H, d, J=4 Hz).

w4) trans-(E)-5,6-Difluoro-2-(2-(1-(4-(3-phenylpropenoyl)amino)cyclohexyl)ethyl)-1,2,3,4-tetrahydroisoquinoline Mass spectrum (API$^+$): Found 425 (MH$^+$). C$_{26}$H$_{30}$F$_2$N$_2$O requires 424. $^1$H NMR (CDCl$_3$) δ: 1.08–1.42 (5H, m), 1.51 (2H, m), 1.81 (2H, m), 2.06 (2H m), 2.53 (2H, m), 2.71 (2H, m), 2.86 (2H, m), 3.55 (2H, s), 3.89 (1H, m), 5.44 (1H, m), 6.35 (1H, d, J=16 Hz), 6.75 (1H, m), 6.92 (1H, m), 7.45 (3H, m), 7.49 (2H, m), 7.62 (1H, d, J=16 Hz).

x4) trans-(E)-5,6-Difluoro-2-(2-(1-(4-(3-(3-methylsulfonamido)phenylpropenoyl)amino)cyclohexyl)ethyl)-1,2,3,4-tetrahydroisoquinoline Mass spectrum (API$^+$): Found 518 (MH$^+$). C$_{27}$H$_{33}$F$_2$N$_3$O$_3$S requires 517. $^1$H NMR (CDCl$_3$) δ: 1.05–1.38 (5H, m), 1.51 (2H, m), 1.82 (2H, m), 2.05 (2H, m), 2.53 (2H, m), 2.71 (2H, m), 2.88 (2H, m), 3.01 (3H, s), 3.55 (2H, s), 3.93 (1H, m), 5.63 (1H, d, J=8 Hz), 6.40 (1H, d, J=16 Hz), 6.74 (1H, m), 6.93 (1H, m), 7.30 (4H, m), 7.48 (1H, s), 7.60 (1H, d, J=16 Hz).

y4) trans-(E)-6-Cyano-2-(2-(1-(4-(3-(1-(4-fluoro)naphthyl)propenoyl)amino)cyclohexyl)ethyl)-1,2,3,4-tetrahydroisoquinoline Mass spectrum (API$^+$): Found 482 (MH$^+$). C$_{31}$H$_{32}$FN$_3$O requires 481. $^1$H NMR (DMSO-d$_6$) δ: 1.05–1.45 (5H, m), 1.50 (2H, m), 1.90 (4H, m), 2.55 (2H, m), 2.70 (2H, m), 2.90 (2H, m), 3.66 (2H, s), 3.70 (1H, m), 6.72 (1H, d, J=16 Hz), 7.35 (1H, d, J=8 Hz), 7.45 (1H, m), 7.64 (2H, m), 7.81 (3H, m), 8.16 (3H, m), 8.29 (1H, m).

z4) trans-(E)-2-(2-(1-(4-(3-(4-Benzo[b]furanyl)propenoyl)amino)cyclohexyl)ethyl)-6-cyano-1,2,3,4-tetrahydroisoquinoline Mass spectrum (API$^+$): Found 454 (MH$^+$). C$_{29}$H$_{31}$N$_3$O$_2$ requires 453. $^1$H NMR (DMSO-d$_6$) δ: 1.00–1.32 (5H, m), 1.47 (2H, m), 1.85 (4H, m), 2.52 (2H, m), 2.68 (2H, m), 2.86 (2H, m), 3.62 (3H, s), 6.84 (1H, d, J=16 Hz), 7.34 (3H, m), 7.48 (1H, m), 7.63 (4H, m), 8.07 (1H, m), 8.17 (1H, m).

a5) trans-(E)-2-(2-(1-(4-(3-(2-Cyano)phenylpropenoyl)amino)cyclohexyl)ethyl)-5-trifluoromethyl-1,2,3,4-tetrahydroisoquinoline Mass spectrum (API$^+$): Found 482 (MH$^+$). C$_{28}$H$_{30}$F$_3$N$_3$O requires 481. $^1$H NMR (CDCl$_3$) δ: 1.06–1.30 (5H, m), 1.52 (2H, m), 1.84 (2H, m), 2.06 (2H, m), 2.53 (2H, m), 2.73 (2H, t, J=6 Hz), 3.07 (2H, m), 3.66 (2H, s), 3.87 (1H, m), 5.54 (1H, d, J=8 Hz), 6.66 (1H, d, J=16 Hz), 7.21 (2H, m), 7.45 (2H, m), 7.61 (2H, m), 7.70 (1H, d, J=8 Hz), 7.78 (1H, d, J=16 Hz).

b5) trans-(E)-2-(2-(1(4-(3(4-Cyano)phenylpropenoyl)amino)cyclohexyl)ethyl)-5-trifluoromethyl-1,2,3,4-tetrahydroisoquinoline Mass spectrum (API$^+$): Found 482 (MH$^+$). C$_{28}$H$_{30}$F$_3$N$_3$O requires 481. $^1$H NMR (CDCl$_3$) δ: 1.08–1.30 (5H, m), 1.54 (2H, m), 1.85 (2H, m), 2.06 (2H, m), 2.53 (2H, m), 2.73 (2H, t, J=6 Hz), 3.07 (2H, m), 3.66 (2H, s), 3.88 (1H, m), 5.54 (1H, d, J=8 Hz), 6.42 (1H, d, J=16 Hz), 7.20 (1H, m), 7.47 (1H, m), 7.62 (5H, m).

c5) trans-6-Pentafluoroethyl-2-(2-(1-(4-(4-quinolinyl)carboxamido)cyclohexyl)ethyl)-1,2,3,4-tetrahydroisoquinoline Mass spectrum (API$^+$): Found 532 (MH$^+$). C$_{29}$H$_{30}$F$_5$N$_3$O requires 531. $^1$H NMR (CDCl$_3$) δ: 1.10–1.49 (5H, m), 1.57 (2H, m), 1.91 (2H, m), 2.20 (2H, m), 2.56 (2H, t, J=7 Hz), 2.75 (2H, t, J=6 Hz), 2.96 (2H, t, J=6 Hz), 3.65 (2H, s), 4.05 (1H, m), 5.95 (H, d, J=8 Hz), 7.15 (1H, d, J=8 Hz), 7.33 (2H, m), 7.40 (1H, d, J=4 Hz), 7.60 (1H, dt, J=8, 2 Hz), 7.75 (1H, dt, J=8, 2 Hz), 8.15 (1H, d, J=8 Hz), 8.21 (1H, d, J=8 Hz), 8.91 (1H, d, J=4 Hz).

d5) trans-6-Cyano-2-(2-(1-(4-(4-(6-fluoro)quinolinyl)carboxamido)cyclohexyl)ethyl)-1,2,3,4-tetrahydroisoquinoline Mass spectrum (API$^+$): Found 457 (MH$^+$). C$_{28}$H$_{29}$FN$_4$O requires 456. $^1$H NMR (CDCl$_3$) δ: 1.05–1.45 (5H, m), 1.55 (2H, m), 1.90 (2H, m), 2.19 (2H, m), 2.56 (2H, m), 2.74 (2H, t, J=6 Hz), 2.93 (2H, t, J=6 Hz), 3.66 (2H, s), 4.04 (1H, m), 5.97 (1H, d, J=8 Hz), 7.11 (1H, d, J=8 Hz), 7.41 (3H, m), 7.52(1H, m), 7.87 (1H, m), 8.12 (1H, m), 8.87 (1H, d, J=4 Hz).

e5) trans-6-Cyano-2-(2-(1-(4-(1-isoquinolinyl)carboxamido)cyclohexyl)ethyl)-1,2,3,4-tetrahydroisoquinoline Mass spectrum (API$^+$): Found 439 (MH$^+$). C$_{28}$H$_{30}$N$_4$O requires 438. $^1$H NMR (CDCl$_3$) δ: 1.10–1.45 (5H, m), 1.55 (2H, m), 1.88 (2H, m), 2.16 (2H, m), 2.57 (2H, m), 2.75 (2H, t, J=6 Hz), 2.93 (2H, t, J=6 Hz), 3.66 (2H, s), 3.97 (1H, m), 7.10 (1H, d, J=8 Hz), 7.40 (2H, m), 7.68 (2H, m), 7.83 (2H, m), 8.05 (1H, d, J=8 Hz), 8.45 (1H, d, J=6 Hz), 9.60 (1H, m).

f5) trans-(E)-2-(2-(1-(4-(3-(3-Acetamido)phenylpropenoyl)amino)cyclohexyl)eyhyl)-5-pentafluoroethyl-1,2,3,4-tetrahydroisoquinoline Mass spectrum (API$^+$): Found 564 (MH$^+$). C$_{30}$H$_{34}$F$_5$N$_3$O$_2$ requires 563. $^1$H NMR (CDCl$_3$) δ: 1.00–1.40 (5H, m), 1.54 (2H, m), 1.83 (2H, m), 2.05 (2H, m), 2.19 (3H, s), 2.54 (2H, m), 2.76 (2H, t, J=7 Hz), 1.97 (2H, m), 3.65 (2H, s), 3.82 (1H, m), 5.98 (1H, d, J=8 Hz), 6.39 (1H, d, J=16 Hz), 7.19 (2H, m), 7.20–7.48 (4H, m), 7.41 (1H, d, J=8 Hz), 7.53 (1H, d, J=16 Hz), 7.80 (1H, br s).

g5) trans-6-Cyano-2-(2-(1-(4-(4-(3-fluoro)quinolinyl)carboxamido)cyclohexyl)ethyl)-1,2,3,4-tetrahydroisoquinoline Mass spectrum (API$^+$): Found 457 (MH$^+$). C$_{28}$H$_{29}$FN$_4$O requires 456. $^1$H NMR (CDCl$_3$) δ: 1.11–1.38 (5H, m), 1.55 (2H, m), 1.89 (2H, m), 2.22 (2H, m), 2.56 (2H, m) 2.74 (2H, t, J=6 Hz), 2.92 (2H, m), 3.65 (2H, s) 4.10 (1H, m), 5.98 (1H, m), 7.11 (1H, d, J=8 Hz), 7.39 (2H, m) 7.67 (2H, m) 8.08 (2H, m), 8.82 (1H, s).

h5) trans-6-Cyano-2-(2-(1-(4-(5-isoquinolinyl)carboxamido)cyclohexyl)ethyl)-1,2,3,4-tetrahydroisoquinoline Mass spectrum (API$^+$): Found 439 (MH$^+$). C$_{28}$H$_{30}$N$_4$O requires 438. $^1$H NMR (CDCl$_3$) δ: 1.10–1.80 (7H, m), 1.80–2.00 (2H, m), 2.10–2.30 (2H, m), 2.50–2.65 (2H, m), 2.70–2.80 (2H, m), 2.85–2.95 (2H, m), 3.66 (2H, s), 3.95–4.12 (1H, m), 5.88 (1H, d, J=8 Hz), 7.12 (1H, d, J=8 Hz), 7.38–7.45 (2H, m), 7.55–7.65 (1H, m), 7.82 (1H, dd, J=6, 1Hz), 8.04 (1H, d, J=8 Hz), 8.17 (1H, d, J=7 Hz), 8.58 (1H, d, J=6 Hz), 9.27 (1H, s).

i5) trans-6-Cyano-2-(2-(1-(4-(4-(7-fluoro)quinolinyl)carboxamido)cyclohexyl)ethyl)-1,2,3,4-tetrahydroisoquinoline.

Mass spectrum (API⁺): Found 457 (MH⁺). $C_{28}H_{29}FN_4O$ requires 456. ¹H NMR (DMSO-$d_6$) δ: 1.06–1.44 (5H, m), 1.50 (2H, m), 1.88 (2H, m), 2.05 (2H, m), 2.54 (2H, m), 2.72 (2H, t, J=6 Hz), 2.91 (2H, m), 3.68 (2H, s), 3.88 (1H, m), 7.34 (1H, d, J=8 Hz), 7.57 (1H, d, J=4 Hz), 7.71 (3H, m), 7.90 (1H, dd, J=10, 2 Hz), 8.25 (1H, m) 8.76 (1H, d, J=8 Hz), 9.05 (1H, d, J=4 Hz).

j5) trans-6-Cyano-2-(2-(1-(4-(5-(1,2-dihydro-2-oxo) quinolinyl)carboxamido)cyclohexyl)ethyl)-1,2,3,4-tetrahydroisoquinoline Mass spectrum (API⁺): Found 455 (MH⁺). $C_{28}H_{30}N_4O_2$ requires 454. ¹H NMR (CDCl₃) δ: 1.10–1.40 (5H, m), 1.55 (2H, m), 1.88 (2H, m), 2.15 (2H, m), 2.55 (2H, m), 2.74 (2H, t, J=6 Hz), 2.92 (2H, t, J=6 Hz), 3.65 (2H, s), 3.98 (1H, m), 6.00 and 6.35 (1H, 2×d, J=8 Hz), 6.73 (1H, m), 7.11 (1H, d, J=8 Hz), 7.26 (1H, m), 7.40 (3H, m), 7.60 and 7.71 (1H, 2×s), 7.81 and 8.30 (1H, 2×d, J=8 Hz), 11.95 and 12.21 (1H, 2×br s).

k5) trans-6-Cyano-2-(2-(1-(4-(5-(2,3-dihydro-3-oxo)-4H-benzoxazinyl)-carboxamido)cyclohexyl)ethyl)-1,2,3,4-tetrahydroisoquinoline Mass spectrum (API⁺): Found 459 (MH⁺). $C_{27}H_{30}N_4O_3$ requires 458. ¹H NMR (CDCl₃) δ: 1.10–1.45 (5H, m), 1.55 (2H, m), 1.87 (2H, m), 2.09 (2H, m), 2.54 (2H, m), 2.73 (2H, t, J=6 Hz), 2.92 (2H t, J=6 Hz), 3.65 (2H, s), 3.90 (1H, m), 4.61 (2H, s), 6.00 (1H, d, J=8 Hz), 6.94 (1H, m), 7.10 (3H, m), 7.40 (2H, m), 10.74 (1H, br s).

l5) trans-(E)-8-Cyano-2-(2-(1-(4-(3-phenylopropenoyl) amino)cyclohexyl)ethyl)-1,2,3,4-tetrahydroisoquinoline Mass spectrum (API⁺): Found 414 (MH⁺). $C_{27}H_{31}N_3O$ requires 413. ¹H NMR (CDCl₃) δ: 1.10–1.65 (1H, m), 1.80–1.95 (2H, m), 2.08–2.15 (2H, m), 2.55–2.65 (2H, m), 2.70–2.77 (2H, m), 2.89–2.95 (2H, m), 3.79 (2H, s), 3.85–4.00 (1H, m), 5.39 (1H, d, J=8 Hz), 6.34 (1H, d, J=16 Hz), 7.20–7.25 (1H, m), 7.28–7.42 (4H, m), 7.43–7.54 (3H, m), 7.60 (1H, d, J=16 Hz).

m5) trans-8-Cyano-2-(2-(1-(4-(2-indolyl)carboxamido) cyclohexyl)ethyl)-1,2,3,4-tetrahydroisoquinoline Mass spectrum (API⁺): Found 427 (MH⁺). $C_{27}H_{30}N_4O$ requires 426. ¹H NMR (CDCl₃) δ: 1.45–1.64 (7H, m), 1.80–1.95 (2H, m), 2.10–2.18 (2H, m), 2.55–2.66 (2H, m), 2.70–2.80 (2H, m), 2.90–2.97 (2H, m), 3.80 (2H, s), 3.90–4.00 (1H, m), 5.93 (1H, d, J=8 Hz), 6.79 (1H, m), 7.10–7.45 (6H, m), 7.64 (1H, d J=8 Hz), 9.11 (1H, br s).

n5) trans-7-Cyano-2-(2-(1-(4-(2-indolyl)carboxamido) cyclohexyl)ethyl)-6-methyl-1,2,3,4-tetrahydroisoquinoline Mass spectrum (API⁺): Found 441 (MH⁺). $C_{28}H_{32}N_4O$ requires 440. ¹H NMR (DMSO-$d_6$+TFA) δ: 1.15 (2H, m), 1.40 (3H, m), 1.60–2.05 (6H, m), 2.55 (3H, s), 3.15 (2H, m), 3.26 (3H, m), 3.76 (2H, m), 4.32 (1H, m), 4.63 (1H, m), 7.05 (1H, t, J=8 Hz), 7.20 (2H, m), 7.42 (2H, m), 7.61 (1H, d, J=8 Hz), 7.71 (1H, s), 8.25 (1H, d, J=8 Hz), 10.26 (1H, br, s), 11.54 (1H, br s).

o5) trans-6-Cyano-2-(2-(1-(4-(2-naphthyl)carboxamido) cyclohexyl)ethyl)-1,2,3,4-tetrahydroisoquinoline Mass spectrum (API⁺): Found 438 (MH⁺). $C_{29}H_{31}N_3O$ requires 437. ¹H NMR (DMSO-$d_6$) δ: 1.10 (2H, m), 1.53 (5H, m), 1.88 (4H, m), 2.52 (2H, m), 2.67 (2H, m), 2.86 (2H, m), 3.63 (2H, m), 3.82 (1H, m), 7.30 (1H, d, J=8 Hz), 7.61 (4H, m), 8.00 (4H, m), 8,42 (2H, m).

p5) trans-2-(2-(1(4-(4-(4-Acetyl)phenyl)benzoyl) aminocyclohexyl)ethyl)-5-cyano-1,2,3,4-tetrahydroisoquinoline Mass spectrum (AP⁺): Found 506 (MH⁺). $C_{33}H_{35}N_3O_2$ requires 505. ¹H NMR (DMSO-$d_6$+TFA) δ: 0.85–1.10 (2H, m), 1.12–1.40 (3H, m), 1.58 (2H, m), 1.62–1.89 (4H, m), 2.50 (3H, m), 3.00–3.43 (5H, m), 3.69 (2H, m), 4.25 (1H, m), 4.57 (1H, m), 7.39 (1H, t, J=9 Hz), 7.48 (1H, d, J=9 Hz), 7.67–7.80 (5H, m), 7.86 (2H, d, J=9 Hz), 7.95 (2H, d, J=9 Hz), 8.23 (1H, d, J=9 Hz), 10.00 (1H, br s).

q5) trans-(E)-7-Cyano-6-methyl-2-(2-(1-(4-(3-phenylpropenoyl)amino)cyclohexyl)ethyl)-1,2,3,4-tetrahydroisoquinoline Mass spectrum (API⁺): Found 428 (MH⁺). $C_{28}H_{31}N_3O$ requires 427. ¹H NMR (CDCl₃) δ: 1.05–1.43 (5H, m), 1.51 (2H, m), 1.87 (2H, m), 2.08 (2H, m), 2.46 (3H, s), 2.54 (2H, m), 2.71 (2H, t, J=7 Hz), 2.90 (2H, t, J=7 Hz), 3.56 (2H, s), 3.87 (1H, m), 5.51 (1H, d, J=8 Hz), 6.36 (1H, d, J=16 Hz), 7.07 (1H, s), 7.29 (1H, s), 7.35 (3H, m), 7.50 (2H, m), 7.61 (1H, d, J=16 Hz).

EXAMPLE 9 trans-(E)-2-(2-(1-(4-(3-(3-Acetamido) phenylpropenoyl)amino)cyclohexyl)ethyl)-6-cyano-1,2,3,4-tetrahydroisoquinoline Prepared in a similar manner to Example 3, using (E)-3-(3-acetamido)phenylpropenoic acid instead of (E)-3-(3-methylsulfonyl)phenylpropenoic acid, in 86% yield.

Mass spectrum (API⁺): Found 471 (MH⁺). $C_{29}H_{34}N_4O_2$ requires 470. ¹H NMR (DMSO-$d_6$) δ: 0.88–1.17 (5H, m), 1.33 (2H, m), 1.70 (4H, m), 1.96 (3H, s), 2.39 (2H, m), 2.54 (2H, m), 2.74 (2H, m), 3.50 (3H, m), 6.46 (1H, d, J=16 Hz), 7.09 (1H, m), 7.22 (3H, m), 7.36 (1H, m), 7.48 (2H, m), 7.81 (1H, m), 7.97 (1H, d, J=8 Hz), 9.97 (1H, br s).

EXAMPLE 10 trans-(E)-6-Cyano-2-(2-(1-(4-(3-(3-methoxy) phenylpropenoyl)amino)cyclohexyl)eyhyl)-1,2,3,4-tetrahydroisoquinoline Prepared in a similar manner to Example 3, using (E)-3-(3-methoxy)phenylpropenoic acid instead of (E)-3-(3-methylsulfonyl)phenylpropenoic acid, in 24% yield.

Mass spectrum (API⁺): Found 444 (MH⁺). $C_{28}H_{33}N_3O_2$ requires 443. ¹H NMR (DMSO-$d_6$) δ: 0.92–1.25 (5H, m), 1.42 (2H, m), 1.79 (4H, m), 2.46 (2H, m), 2.63 (2H, m), 2.83 (2H, m), 3.59 (3H, m), 3.77 (3H, s), 6.59 (1H, d, J=16 Hz), (1H, m), 7.10 (2H, m), 7.32 (3H, m), 7.58 (2H, m), 7.96 (1H, d, J=8 Hz).

EXAMPLE 11 trans-(E)-2-(2-(1-(4-(3-(3-Chloro)phenylpropenoyl) amino)cyclohexyl)ethyl)-6-cyano-1,2,3,4-tetrahydroisoquinoline Prepared in a similar manner to Example 3, using (E)-3-(3-chloro)phenylpropenoic acid instead of (E3-(3-methylsulfonyl)phenylpropenoic acid, in 72% yield.

Mass spectrum (API⁺): Found 448 (MH⁺). $C_{27}H_{30}{}^{35}ClN_3O$ requires 447. ¹H NMR (DMSO-$d_6$) δ: 0.88–1.22 (5H, m), 1.39 (2H, m), 1.76 (4H, m), 2.43 (2H, m), 2.59 (2H, m), 2.79 (2H, m), 3.55 (3H, m), 6.60 (1H, d, J=16 Hz), 7.22 (1H, d, J=8 Hz), 7.33 (3H, m), 7.50 (4H, m), 7.94 (1H, d, J=8 Hz).

EXAMPLE 12 trans-2-(2-(1-(4-(4-Cinnolinyl)carboxamido) cyclohexyl)ethyl)-7-cyano-1,2,3,4-tetrahydroisoquinoline Prepared in a similar manner to Example 7, using cinnoline-4-carboxylic acid instead of 6-cyanoindole-2-carboxylic acid.

Mass spectrum (API+): Found 440 (MH+). $C_{27}H_{29}N_5O$ requires 439. $^1$H NMR (CDCl$_3$) δ: 1.10–1.50 (5H, m), 1.50–1.70 (2H, m), 1.85 (2H, m), 2.25 (2H, m), 2.57 (2H, t, J=8 Hz), 2.74 (2H, t, J=6 Hz), 2.96 (2H, t, J=6 Hz), 3.62 (2H, s), 4.05 (1H, m), 6.08 (1H, br s), 7.20 (1H, d, J=8 Hz), 7.33 (1H, s), 7.40 (1H, d, J=8 Hz), 7.80–8.00 (2H, m), 8.31 (1H, d, J=8 Hz), 8.57 (1H, d, J=8 Hz), 9.28 (1H, s).

EXAMPLE 13 trans-(E)-6-Cyano-2-(2-(1-(4-(3-(4-fluoro) phenylpropenoyl)amino)cyclohexyl)ethyl)-1,2,3,4-tetrahydroisoquinoline

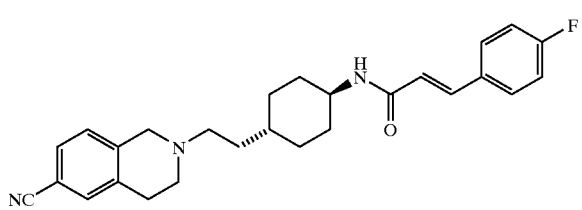

Alternative name: trans-(E)-N-[4-[2-(6-Cyano-1,2,3,4-tetrahydroisoquinolin-2-yl)ethyl]cyclohexyl]-3-(4-fluorophenyl)-2-propenamide Prepared in a similar manner to Example 3, using (E)-3-(fluoro)phenylpropenoic acid instead of (E)-3-(3-methanesulfonyl)phenylpropenoic acid, in 66% yield.

Mass spectrum (API+): Found 432 (MH+). $C_{27}H_{30}FN_3O$ requires 431. $^1$H NMR (CDCl$_3$+CD$_3$OD) δ: 1.03–1.40 (5H, m), 1.54 (2H, m), 1.84 (2H, m), 2.05 (2H, m), 2.55 (2H, m), 2.75 (2H, t, J=7 Hz), 2.94 (2H, m), 3.66 (2H, s), 3.82 (1H, m), 5.90–6.15 (1H, m), 6.30 (1H, d, J=16 Hz), 6.97–7.17 (3H, m), 7.35–7.61 (5H, m).

EXAMPLE 14 trans-(E)-6-Cyano-2-(2-(1-(4-(3-(2,5-difluoro) phenylpropenoyl)amino)cyclohexyl)ethyl)-1,2,3,4-tetrahydroisoquinoline Prepared in a similar manner to Example 3, using (E)-3-(2,5-difluoro)phenylpropenoic acid instead of (E)-3-(3-methanesulfonyl)phenylpropenoic acid, in 51% yield.

Mass spectrum (API−): Found 448 (MH−). $C_{27}H_{29}F_2N_3O$ requires 449. $^1$H NMR (CDCl$_3$) δ: 1.25 (5H, m), 1.53 (2H, m), 1.86 (2H, m), 2.06 (2H, m), 2.55 (2H, m), 2.73 (2H, t, J=6 Hz), 2.92 (2H, t, J=6 Hz), 3.65 (2H, s), 3.88 (1H, m), 5,45 (1H, d, J=* Hz), 6.45 (1H, d, J=16 Hz), 6.90–7.20 (4H, m), 7.39 (2H, m), 7.62 (1H, d, J=6 Hz).

EXAMPLE 15 trans-6-Cyano-2-(2-(1-(4-(5-quinolinyl) carboxamido)cyclohexyl)ethyl)-1,2,3,4-tetrahydroisoquinoline

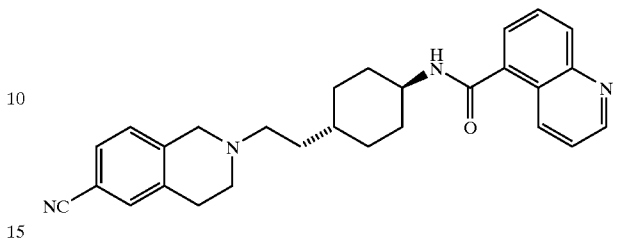

Alternative name: trans-N-[4-[2-(6-Cyano-1,2,3,4-tetrahydroisoquinolin-2-yl)ethyl]cyclohexyl]-5-quinolinecarboxamide Prepared in a similar manner to Example 7, using quinoline-5-carboxylic acid instead of 6-cyanoindole-2-carboxylic acid, in 89% yield.

Mass spectrum (API+): Found 439 (MH+). $C_{28}H_{30}N_4O$ requires 438. $^1$H NMR ((CD$_3$)$_2$SO) δ: 1.10–1.30 (2H, m), 1.30–1.50 (3H, m), 1.50–1.60 (2H, m), 1.93 (2H, m), 2.07 (2H, m), 2.60 (2H, m), 2.76 (2H, t, J=6 Hz), 2.95 (2H, t, J=6 Hz), 3.72 (2H, s), 3.90 (1H, m), 7.39 (1H, d, J=8 Hz), 7.60–7.70 (3H, m), 7.78 (1H, d, J=6 Hz), 7.89 (1H, t, J=7 Hz), 8.20 (1H, d, J=8 Hz), 8.61 (1H, d, J=8 Hz), 8.69 (1H, d, J=8 Hz), 9.05 (1H, m).

EXAMPLE 16 trans-(E)-6-Bromo-2-(2-(1-(4-(3-(3-methylsulfonyl) phenylpropenoyl)amino)cyclohexyl)ethyl)-1,2,3,4-tetrahydroisoquinoline Prepared in a similar manner to Example 3, using trans-2-(2-(1-(4-amino)cyclohexyl)ethyl)-6-bromo-1,2,3,4-tetrahydroisoquinoline instead of trans-2-(2-(1-(4-amino) cyclohexyl)ethyl)-6-cyano-1,2,3,4-tetrahydroisoquinoline, in 50% yield.

Mass spectrum (API+): Found 545 (MH+). $C_{27}H_{33}{}^{79}Br_2N_2O_3S$ requires 544. $^1$H NMR (CDCl$_3$) δ: 1.13 (5H, m), 1.51 (2H, m), 1.82 (2H, m), 2.05 (2H, m), 2.52 (2H, m), 2.69 (2H, t, J=6 Hz), 2.87 (2H, m), 3.07 (3H, s), 3.54 (2H, s), 3.86 (1H, m), 5.62 (1H, d, J=8 Hz), 6.49 (1H, d, J=15 Hz), 6.89 (1H, d, J=8 Hz), 7.24 (2H, m), 7.63 (3H, m), 7.90 (1H, m), 8.10 (1H, m).

EXAMPLE 17 trans-(E)-2-(2-(1-(4-(3-(3-Methylsulfonyl) phenylpropenoyl)amino)cyclohexyl)ethyl)-6-trinfluoromethyl-1,2,3,4-tetrahydroisoquinoline Prepared in a similar manner to Example 3, using trans-2-(2-(1-(4-amino)cyclohexyl)ethyl)-6-trifluoromethyl-1,2, 3,4-tetrahydroisoquinoline instead of trans-2-(2-(1-(4-amino)cyclohexyl)ethyl)-6-cyano-1,2,3,4-tetrahydroisoquinoline, in 50% yield.

Mass spectrum (API+): Found 535 (MH+). $C_{27}H_{33}F_3N_2O_3S$ requires 534. $^1$H NMR (CDCl$_3$) δ: 1.17 (5H, m), 1.52 (2H, m), 1.83 (2H, m), 2.06 (2H, m), 2.55 (2H, m), 2.74 (2H, t, J=6 Hz), 2.95 (2H, m), 3.07 (3H, s), 3.65 (2H, s), 3.86 (1H, m), 5.52 (1H, d, J=8 Hz), 6.48 (1H, d, J=15 Hz), 7.12 (1H, d, J=8 Hz), 7.36 (1H, m), 7.63 (3H, m), 7.90 (1H, m), 8.09 (1H, m).

EXAMPLE 18 trans-(E)-2-(2-(1-(4-(3-(3-Methylsulfonyl)phenylpropenoyl)amino)cyclohexyl)ethyl)-6-trifluoromethoxy-1,2,3,4-tetrahydroisoquinoline Prepared in a similar manner to Example 3, using trans-2-(2-(1-(4-amino)cyclohexyl)ethyl)-6-trifluoromethoxy-1,2,3,4-tetrahydroisoquinoline instead of trans-2-(2-(1-(4-amino)cyclohexyl)ethyl)-6-cyano-1,2,3,4-tetrahydroisoquinoline, in 50% yield.

Mass spectrum (API⁺): Found 551 (MH⁺). $C_{28}H_{33}F_3N_2O_4S$ requires 550. ¹H NMR (CDCl₃) δ: 1.15 (5H, m), 1.52 (2H, m), 1.84 (2H, m), 2.06 (2H, m), 2.53 (2H, m), 2.71 (2H, t, J=6 Hz), 2.91 (2H, m), 3.07 (3H, s), 3.59 (2H, s), 3.85 (1H, m), 5.76 (1H, d, J=8 Hz), 6.51 (1H, d,=15 Hz), 6.99 (3H, m), 7.62 (3H, m), 7.89 (1H, m), 8.10 (1H, m).

EXAMPLE 19 trans-6-Cyano-2-(2-(1-(4-(4-quinolinyl)carboxamido)cyclohexyl)ethyl)-1,2,3,4-tetrahydroisoquinoline

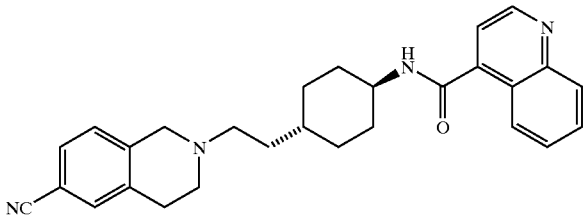

Alternative name: trans-N-[4-[2-(6-cyano-1,2,3,4-tetrahydroisoquinolin-2-yl)ethyl]cyclohexyl]-4-quinolinecarboxamide A mixture of trans-2-(2-(1-(4-amino)cyclohexyl)ethyl)-6-cyano-1,2,3,4-tetrahydroisoquinoline (4 g, 14.1 mmol), quinoline-4-carboxylic acid (2.45 g, 14.1 mmol) 1-ethyl-3-(3-dimethylaminopropyl)carbodiimide hydrochloride (2.71 g, 14.1 mmol), 1-hydroxybenzotriazole (0.251 g. 1.86 mmol) and dichloromethane (150 ml) was stirred at room temperature for 3 h. Further dichloromethane (50 ml) was added and stirring continued for 17 h. Dichloromethane (200ml) was added and the mixture washed with saturated aqueous sodium hydrogen carbonate (500 ml). The aqueous phase was extracted with dichloromethane (2×250 ml). Combined organic extracts were dried (Na₂SO₄) and evaporated in vacuo. The residue was purified by chromatography on silica gel (350 ml) using 10–100% ethyl acetate-hexane then 1–5% methanol-ethyl acetate gradient elution to give the title compound (3.06 g, 49.4%) as a colourless solid. A sample recrystallised from ethyl acetate-dichloromethane, m.p. 207–210° C.

Mass spectrum (API⁺): Found 439 (MH⁺). $C_{28}H_{30}N_4O$ requires 438. ¹H NMR (CDCl₃) δ: 1.17–1.45 (5H, m), 1.53 (2H, m), 1.89 (2H, m), 2.20 (2H, m), 2.55 (2H, m), 2.73 (2H, t, J=6 Hz), 2.91 (2H, t, J=6 Hz), 3.65 (2H, s), 4.07 (1H, m), 5.83 (1H, d, J=8 Hz), 7.10 (1H, d, J=8 Hz), 7.38 (3H, m), 7.60 (1H, m), 7.76 (1H, m), 8.12 (1H, m), 8.19 (1H, m), 8.90 (1H, d, J=4 Hz): this is a more detailed interpretation of the spectrum for this compound compared to that of Example 8b4.

Treatment of a solution of the free base (1.54 g, 3.52 mmol) in ethanol (10 ml) and dichloromethane (10 ml) with a solution of methanesulfonic acid (0.316 g, 3.3 mmol) in ethanol (2 ml), followed by evaporation in vacuo, gave a solid. An aliquot (0.60 g) was recrystallised from 1% aqueous isopropanol to give trans-6-cyano-2-(2-(1-(4-(4-quinolyl)carboxamido)cyclohexyl)ethyl)-1,2,3,4-tetrahydroisoquinoline monomesylate (0.16 ) as an off white solid, m.p. 255–259° C. dec.

¹H NMR (DMSO-d₆) δ: 1.05–1.23 (2H, m), 1.25–1.45 (3H, m), 1.69 (2H, m), 1.84 (2H, m), 2.02 (2H, m), 2.30 (3H, s), 3.15 (2H, m), 3.19–3.42 (3H, m), 3.65–3.95 (2H, m), 4.39 (1H, m), 4.70 (1H, m), 7.45 (1H, d, J=8 Hz), 7.51 (1H, d, J=4 Hz), 7.66 (1H, dt, J=8, 2 Hz), 7.71–7.86 (3H, m), 8.09 (2H, m), 8.70 (1H, d, J=8 Hz), 8.98 (1H, d, J=4 Hz), 9.84 (1H, br s).

Treatment of a solution of the free base (1.84 g, 4.3 mmol) in methanol (40 ml) and dichloromethane (20 ml) with hydrochloric acid (2M; 2.15 ml), followed by evaporation in vacuo gave a solid. Recrystallisation from ethanol (250 ml) gave trans-6-cyano-2-(2-(1-(4-(4-quinolyl)carboxamido)cyclohexyl)ethyl)-1,2,3,4-tetrahydroisoquinoline monohydrochloride (0.86 g) as an off-white solid, m.p. 216–219° C.

Found C, 69.59; H, 6.49; N, 11.61; Cl, 7.47. $C_{28}H_{30}N_4O·HCl·0.2H_2O$ requires C, 70.33; H, 6.73; N, 11.72; Cl, 7.41%. ¹H NMR (DMSO-d₆) δ: 1.03–1.25 (2H, m), 1.25–1.45 (3H, mn), 1.67–1.90 (4H, m), 2.01 (2H, m), 3.09 (1H, m), 3.26 (4H, m), 3.72 (1H, m), 3.82 (1H, m), 4.37 (1H, m), 4.65 (1H, m), 7.45 (1H, d, J=8 Hz), 7.51 (1H, d, J=4 Hz), 7.64–7.87 (4H, m), 8.10 (2H, m), 8.7 0 (1H, d, J=8 Hz), 8.97 (1H, d, J=4 Hz), 11.01 (1H, br s).

EXAMPLE 20 trans-(E)-6Cyano-2-(2-(1-(4-(3-(2,4-difluoro)phenylpropenoyl)amino)cyclohexyl)ethyl)-1,2,3,4-tetrahydroisoquinoline.

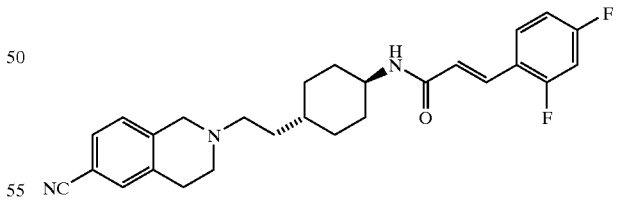

Alternative name: trans-(E)-N-[-4-[2-(6-Cyano-1,2,3,4-tetrahydroisoquinolin-2-yl)ethyl]cyclohexyl]-3-(2,4-difluorophenyl)-2-propenamide A mixture of trans-2-(2-(1-(4-amino)cyclohexyl)ethyl)-6-cyano-1,2,3,4-tetrahydroisoquinoline (0.1 g, 0.353 mmol), (E)-3-(2,4-difluoro)phenylpropenoic acid (0.065 g, 0.353 mmol), 1-ethyl-3-(3-dimethylaminopropyl)carbodiimide hydrochloride (0.069 g, 0.353 mmol), 1-hydroxybenzotriazole (catalytic amount) and dichloromethane (4 ml) was treated in a manner similar to Example 1 to give the title compound (0.131 g, 82%) as a colorless solid.

Mass spectrum (API+): Found 450 (MH+). $C_{27}H_{29}F_2N_3O$ requires 449. $^1$H NMR (CDCl$_3$) δ: 1.05–1.45 (5H, m), 1.51 (2H, m), 1.80 (2H, m), 2.04 (2H, m), 2.54 (2H, m), 2.73 (2H, t, J=6 Hz), 2.92 (2H, t, J=6 Hz,), 3.64 (2H, s), 3.88 (1H, m), 5.48 (1H, d, J=8 Hz), 6.43 (1H, d, J=16 Hz), 6.86 (2H, m), 7.11 (1H, d, J=8 Hz), 7.42 (3H, m), 7.61 (1H, d, J=16 Hz).

EXAMPLE 21 trans-2-(2-(1-(4-(3-Benzo[b]furanyl)carboxamido) cyclohexyl)ethyl)-6-cyano-1,2,3,4-tetrahydroisoquinoline

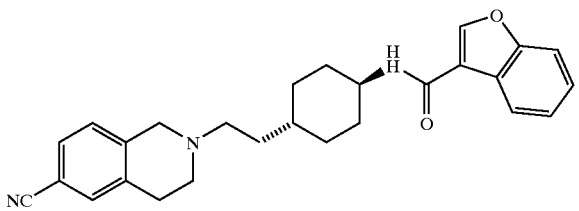

Alternative name: trans-N-[4-[2-(6-cyano-1,2,3,4-tetrahydroisoquinolin-2-yl)ethyl]cyclohexyl]-3-benzofurancarboxamide A mixture of trans-2-(2-(1-(4-amino)cyclohexyl)ethyl-6-cyano-1,2,3,4-tetrahydroisoquinoline (0.1 g, 0.353 mmol), benzo[b]furan-3-carboxylic acid (0.052 g, 0.353 mmol), 1-ethyl-3-(3-dimethylaminopropyl)carbodiimide hydrochloride (0.067 g, 0.353 mmol), 1-hydroxybenzotriazole (catalytic amount) and dichloromethane (4.5 ml ml) was treated in a manner similar to Example 1 to give the title compound (0.076 g 51%) as a colourless solid.

Mass spectrum (API+): Found 428 (MH+). $C_{27}H_{29}N_3O_2$ requires 427. $^1$H NMR (CDCl$_3$) δ: 1.10–1.80 (7H, m), 1.87 (2H, m), 2.15 (2H, m), 2.55 (2H, m), 2.75 (2H, t, J=5.5 Hz), 2.93 (2H, t, J=5.5 Hz), 3.65 (2H, s), 4.00 (1H, m), 5.83 (1H, d, J=8 Hz), 7.11 (1H, d, J=8 Hz), 7.39 (4H, m), 7.50 (1H, m), 7.87 (1H, m), 8.09 (1H, s).

EXAMPLE 22 trans-6-Cyano-2-(2-(1-(4-(7-indolyl)carboxamido) cyclohexyl)ethyl)-1,2,3,4-tetrahydroisoquinoline Prepared in a similar manner to Example 19, using indole-7-carboxylic acid.

Mass spectrum (API+): Found 427 (MH+). $C_{27}H_{30}N_4O$ requires 426. $^1$H NMR (DMSO-$_6$) δ: 1.00–1.20 (2H, m), 1.30–1.60 (5H, m), 1.80–2.00 (4H, m), 2.50 (2H, m), 2.70 (2H, t, J=5 Hz), 2.90 (2H, t, J=5 Hz), 3.66 (2H, s), 3.86 (1H, m), 6.53 (1H, t, J=2 Hz), 7.10 (1H, t, J=8 Hz), 7.33 (1H, d, J=8 Hz), 7.39 (1H, t, J=3 Hz), 7.62 (1H, d, J=8 Hz), 7.65 (1H, s), 7.69 (1H, d, J=8 Hz), 7.75 (1H, d, J=8 Hz), 8.31 (1H, d, J=8 Hz), 11.19 (1H, s).

EXAMPLE 23 trans-6-Cyano-2-(2-(1-(4-(4-(8-fluoro)quinolinyl) carboxamido)cyclohexyl)ethyl)-1,2,3,4-tetrahydroisoquinoline Prepared in a similar manner to Example 19, using 8-fluoro-quinoline-4-carboxylic acid (prepared according to the methods of McKittrik, et al., J. Het Chem., 1990, 27(7), 2151; and Senear, et al., J. Amer. Chem. Soc., 1946, 68, 2695).

Mass spectrum (API+): Found 457 (MH+). $CH_{28}H_{29}N_4OF$ requires 456. $^1$H NMR (CDCl$_3$) δ: 1.10–1.45 (5H, m), 1.65 (2H, m), 1.85 (2H, m), 2.19 (2H, m), 2.56 (2H, m), 2.71 (2H, t, J=6 Hz), 2.92 (2H, t, J=6 Hz), 3.65 (2H, s), 4.05 (1H, m), 6.10 (1H, d, J=8 Hz), 7.11 (1H, d, J=8 Hz), 7.30–7.65 (5H, m), 7.97 (1H, d, J=8 Hz), 8.95 (1H, d, J=4 Hz).

EXAMPLE 24 trans6-Cyano-2-(2-(1-(4-(4-(8-bromo)quinolinyl) carboxamido)cyclohexyl)ethyl)-1,2,3,4-tetrahydroisoquinoline Prepared in a similar manner to Example 19, using 8-bromo-quinoline-4-carboxylic acid (prepared according to the methods of Holt, et al., Proc. Roy. Soc., 1958, 148, 481; and Senear, et al., J. Amer. Chem. Soc., 1946, 68, 2695).

Mass spectrum (API+): Found 519 (MH+). $C_{28}H_{29}N_4O^{81}Br$ requires 518. $^1$H NMR (CDCl$_3$) δ: 1.10–1.45 (5H, m), 1.55 (2H, m), 1.85 (2H, m), 220 (2H, m), 2.55 (2H, m), 2.73 (2H, t, J=6 Hz), 2.91 (2H, t, J=6 Hz), 3.65 (2H, s), 4.03 (1H, m), 5.85 (1H, d, J=8 Hz), 7.10 (1H, d, J=8 Hz), 7.25–7.47 (4H, m), 8.10 (1H, dd, J=8, 2 Hz), 8.20 (1H, dd, J=8, 2 Hz), 9.05 (1H, d, J=4 Hz).

EXAMPLE 25 trans-6-Cyano-2-(2-(1-(4-(4-(8cyano)quinolinyl) carboxamido)cyclohexyl)ethyl-1,2,3,4-tetrahydroisoquinoline Prepared in a similar manner to Example 19, using 8-cyano-quinoline-4-carboxylic acid (prepared from 8-bromo-quinoline-4-carboxylic acid methyl ester by standard methods).

Mass spectrum (API+): Found 464 (MH+). $C_{29}H_{29}N_5O$ requires 463. $^1$H NMR (CDCl$_3$) δ: 1.10–1.45 (5H, m), 1.55 (2H, m), 1.90 (2H, m), 2.19 (2H, m), 2.56 (2H, m), 2.74 (2H, t, J=6 Hz), 2.92 (2H, t, J=6 Hz), 3.66 (2H, s), 4.05 (1H, m), 6.10 (1H, d, J=8 Hz), 7.11 (1H, d, J=8 Hz), 7.40 (2H, m), 7.55 (1H, h, J=4 Hz), 7.66 (1H, m), 8.11 (1H, dd, J=8, 1 Hz), 8.50 (1H, dd, J=8, 1 Hz), 9.06 (1H, d, J=4 Hz).

EXAMPLE 26 trans-6-Cyano-2-(2-(1-(4-(5-(8-fluoro)quinolinyl) carboxamido)cyclohexyl)ethyl)-1,2,3,4-tetrahydroisoquinoline Prepared in a similar manner to Example 19, using 8-fluoro-quinoline-5-carboxylic acid (prepared from 3-amino-4-fluorobenzoic acid according to the method of Bradford, et al., J. Chem. Soc., 1947, 437).

Mass spectrum (API+): Found 457 (MH+). $C_{29}H_{29}N_4OF$ requires 456. $^1$H NMR (CDCl$_3$) δ: 1.10–1.45 (5H, m), 1.56 (2H, m), 1.89 (2H, m), 2.18 (2H, m), 2.56 (2H, m), 2.73 (2H, t, J=6 Hz), 2.92 (2H, t, J=6 Hz), 3.65 (2H, s), 4.05 (1H, m), 5.85 (1H, d, J=8 Hz), 7.10 (1H, d, J=8 Hz), 7.35 (3H, m), 7.54 (1H, m), 7.60 (1H, m), 8.85 (1H, d, J=7 Hz), 9.05 (1H, m).

EXAMPLE 27 trans-6-Cyano-2-(2-(1-(4-(4-(7-cyano)quinolinyl) carboxamido)cyclohexyl)ethyl)-1,2,34-tetrahydroisoquinoline Prepared in a similar manner to Example 19, using 7-cyano-quinoline-4-carboxylic acid (prepared from 8-bromo-quinoline-4-carboxylic acid methyl ester by standard methods).

Mass spectrum (API$^+$): Found 464 (MH$^+$). $C_{29}H_{29}N_5O$ requires 463. $^1$H NMR (DMSO-$_6$) δ: 1.00–1.20 (2H, m), 1.20–1.40 (3H, m), 1.40–1.50 (2H, m), 1.80–1.90 (2H, m), 1.90–2.00 (2H, m), 2.50 (2H, m), 2.65 (2H, t, J=8 Hz), 2.84 (2H, m), 3.61 (2H, s), 3.80 (1H, m), 7.08 (1H, d, J=8 Hz), 7.56 (1H, d, J=8 Hz), 7.58 (1H, s), 7.69 (1H, d, J=4 Hz), 7.97 (1H, dd, J=9, 2 Hz), 8.27 (1H, d, J=9 Hz), 8.67 (1H, d, J=2 Hz), 8.77 (1H, d, J=8 Hz), 9.12 (1H, d, J=4 Hz).

EXAMPLE 28 trans-(2-(1-(4-(3-(7-Fluoro)benzo[b]furanyl)carboxamido)cyclohexyl)ethyl)-6-cyano-1,2,3,4-tetrahydroisoquinoline Prepared in a similar manner to Example 21, using 7-fluoro-benzo[b]furan-3-carboxylic acid (prepared from 3-bromo-7-fluoro-benzo[b]furan by standard methods).

Mass spectrum (API$^+$): Found 446 (MH$^+$). $C_{27}H_{28}N_3O_2$ requires 445. $^1$H NMR (CDCl$_3$) δ: 1.10–1.45 (5H, m), 1.55 (2H, m), 1.86 (2H, m), 2.14 (2H, m), 2.56 (2H, m), 2.73 (2H, t, J=6 Hz), 2.94 (2H, t, J=6 Hz), 3.65 (2H, s), 3.98 (1H, m), 5.90 (1H, d, J=8 Hz), 7.10 (2H, m), 7.30 (1H, m), 7.40 (2H, m), 7.67 (1H, d, J=8 Hz), 8.09 (1H, s).

EXAMPLE 29 trans-2-(2-(1-(4-(3-(5-Cyano)benzo[b]furanyl)carboxamido)cyclohexyl)ethyl)-6-cyano-1,2,3,4-tetrahydroisoquinoline A mixture of trans-2-(2-(1-(4-amino)cyclohexyl)ethyl-6-cyano-1,2,3,4-tetrahydroisoquinoline (0.283 g, 1.0 mmol), 3-bromo-5-cyano-benzo[b]furan (0.212 g, 1.0 mmol) [prepared from 5-bromo-benzo[b]furan using standard methods], tri-n-butylamine (0.26 ml) and trans-bis-triphenylphosphinepalladium(II)bromide (0.04 g) in dimethylacetamide (5 ml) were heated at 100° C. under a CO atmosphere at 30 psi for 18 h. After cooling, the mixture was partitioned between water and ethyl acetate and the organic phase dried and evaporated in vacuo. The residue was chromatographed (Si gel, eluting with 30–100% EtOAc in hexane) to afford the title compound as an off-white solid (0.085 g, 20%).

Mass spectrum (API$^+$): Found 453 (MH$^+$). $C_{28}H_{28}N_4O_2$ requires 452. $^1$H NMR (CDCl$_3$) δ: 1.10–1.40 (5H, m), 1.52 (2H, m), 1.85 (2H, m), 2.15 (2H, m), 2.55 (2H, m), 2.73 (2H, t, J=6 Hz), 2.92 (2H, t, J=6 Hz), 3.65 (2H, s), 3.95 (1H, m), 5.85 (1H, d, J=8 Hz), 7.11 (2H, m), 7.35–7.65 (4H, m), 8.40 (1H, s).

EXAMPLE 30 trans-6-Cyano2-(2-(1-(4-(4-(3-methoxy)quinolinyl)carboxamido)cyclohexyl)ethyl)-1,2,3,4-tetrahydroisoquinoline Prepared in a similar manner to Example 19, using 3-methoxy-quinoline-4-carboxylic acid.

Mass spectrum (API$^+$): Found 469 (MH$^+$). $C_{29}H_{32}N_4O_2$ requires 468. $^1$H NMR (CDCl$_3$) δ: 1.12–1.41 (5H, m), 1.55 (2H, m), 1.89 (2H, m), 2.22 (2H, m), 2.56 (2H, m), 2.74 (2H, t, J=6 Hz), 2.92 (2H, m), 3.65 (2H, s), 4.06 (3H, s), 4.10 (1H, m), 5.93 (1H, d, J=8 Hz), 7.12 (1H, d, J=8 Hz), 7.39 (2H, m), 7.57 (2H, m), 7.93 (1H, dd, J=8, 1 Hz), 8.04 (1H, dd, J=8, 1 Hz), 8.80 (1H, s).

EXAMPLE 31 trans-6-Cyano-2-(2-(1-(4-(5-(8-chloro)quinolinyl)carboxamido)cyclohexyl)ethyl)-1,2,3,4-tetrahydroisoquinoline Prepared in a similar manner to Example 19, using 8-chloro-quinoline-5-carboxylic acid (prepared from 3-amino-4-chlorobenzoic acid according to the method of Bradford, et al., J. Chem. Soc., 1947, 437).

Mass spectrum (API$^+$): Found 473 (MH$^+$). $C_{28}H_{29}N_4O^{35}Cl$ requires 472. $^1$H NMR (CDCl$_3$) δ: 1.10–1.45 (5H, m), 1.55 (2H, m), 1.90 (2H, m), 2.20 (2H, m), 258 (2H, m), 2.74 (2H, t, J=6 Hz), 2.93 (2H, t, J=6 Hz), 3.66 (2H, s), 4.00 (1H, m), 5.93 (1H, d, J=8 Hz), 7.11 (1H, d, J=8 Hz), 7.40 (2H, m), 7.55 (2H, m), 7.83 (1H, d, J=9 Hz), 8.75 (1H, dd, J=9, 2 Hz), 9.05 (1H, m).

EXAMPLE 32 trans-6-Cyano-2-(2-(1-(4-(3-pyrrolo[2,3b]pyridyl)carboxamido)cyclohexyl)ethyl)-1,2,3,4-tetrahydroisoquinoline Prepared in a similar manner to Example 19, using pyrrolo[2,3-b]pyridine-3-carboxylic acid [M. M. Robison, B. L. Robison, J. Am. Chem. Soc. 1956, 78, 1247], in 27% yield.

Mass spectrum (API$^+$): Found 426 (M–H)$^-$. $C_{26}H_{29}N_5O$ requires 427. $^1$H NMR (DMSO-d$_6$) δ: 0.89–1.12 (2H, m), 1.13–1.50 (5H, m), 1.60–1.90 (4H, m), 2.43 (2H, m), 2.60 (2H, m), 2.77 (2H, m), 3.54 (2H, s), 3.69 (1H, m), 7.09 (1H, dd, J=8, 5 Hz), 7.23 (1H, d, J=9 Hz), 7.51 (2H, m), 7.69 (1H, d, J=9 Hz), 8.09 (1H, d, J=3 Hz), 8.18 (1H, m), 8.37 (1H, dd, J=9, 2 Hz), 11.98 (1H, br s).

EXAMPLE 33 trans-2-(2-(4-(3-(7-Cyano)benzo[b]furanyl)carboxamido)cyclohexyl)ethyl)-6-cyano-1,2,3,4-tetrahydroisoquinoline Prepared from 3-bromo-7-cyanobenzo[b]furan (0.318 g, 1.5 mmol) [itself prepared from 7-bromobenzo[b]furan using standard methods] using a procedure similar to that of Example 29, in 18% yield.

Mass spectrum (API$^+$): Found 453 (MH$^+$). $C_{28}H_{28}N_4O_2$ requires 452. $^1$H NMR (CDCl$_3$) δ: 1.02–1.43 (5H, m), 1.54 (2H, m), 1.89 (2H, m), 2.15 (2H, m), 2.56 (2H, t, J=7 Hz), 2.74 (2H, m), 2.92 (2H, m), 3.65 (2H, s), 3.96 (1H, m), 5.90 (1H, d, J=9 Hz), 7.15 (1H, d, J=9 Hz), 7.34–7.52 (3H, m), 7.68 (1H, d, J9 Hz), 8.17 (1H, s), 8.34 (1H, d, J=9 Hz).

What is claimed is:

1. A compound of formula (I):

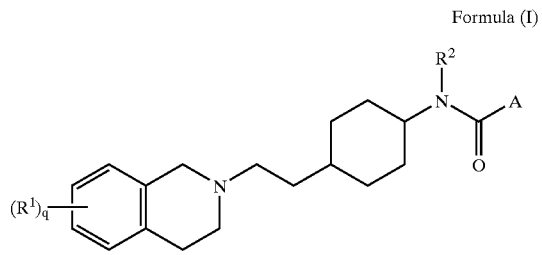

Formula (I)

wherein:

R$^1$ represents a substituent selected from: a hydrogen or halogen atom; a hydroxy, cyano, nitro, trifluoromethyl, trifluoromethoxy, trifluoromethanesulfonyloxy, pentafluoroethyl, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulfonyl, $C_{1-4}$alkylsulfonyloxy, $C_{1-4}$alkylsulfonyl$C_{1-4}$alkyl, arylsulfonyl, arylsulfonyloxy, arylsulfonyl$C_{1-4}$alkyl, $C_{1-4}$alkylsulfonamido, $C_{1-4}$alkylamido, $C_{1-4}$alkylsulfonamido$C_{1-4}$alkyl, $C_{1-4}$alkylamido$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^3$—Z, wherein $Ar^3$ represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

q is 1 or 2;

A represents a group of the formula (a), (b) or (c):

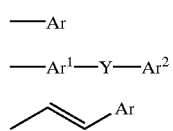

(a) —Ar
(b) —Ar¹—Y—Ar²
(c)

wherein
Ar represents an optionally substituted phenyl ring or an optionally substituted 5- or 6-membered aromatic heterocyclic ring; or an optionally substituted bicyclic ring system;

Ar¹ and Ar² each independently represent an optionally substituted phenyl ring or an optionally substituted 5- or 6-membered aromatic heterocyclic ring; and Y represents a bond, —NHCO—, —CONH—, —CH₂—, or —(CH₂)ₘY¹(CH₂)ₙ—, wherein Y¹ represents O, S, SO₂, or CO and m and n each represent zero or 1 such that the sum of m+n is zero or 1; providing that when A represents a group of formula (a), any substituent present in Ar ortho to the carboxamide moiety is necessarily a hydrogen or a methoxy group;

or a salt thereof.

2. A compound according to claim 1 wherein q represents 1.

3. A compound or salt according to claim 1 wherein A is a group of formula (a) and Ar represents an optionally substituted indolyl, pyrazolo[1,5-a]pyrimidyl, cinnolinyl, quinolinyl, benzo[b]furanyl, or pyrrolopyridyl group.

4. A compound or salt according to claim 1 wherein A is a group of formula (c) and Ar represents an optionally substituted phenyl group.

5. A compound or salt according to claim 1 wherein rings Ar, Ar¹, or Ar² are each independently optionally substituted by one or more substituents selected from: a hydrogen or halogen atom, cyano, methoxy, methylenedioxy, acetyl, acetylamino, methylsulfonyl, methylsulfonyloxy, methylaminosulfonyl, methylsulfonylamino, or methylaminocarbonyl group.

6. A compound of formula (I) which is:

trans-7-Cyano-2-(2-(1-(4-(2-indolyl)carboxamido)cyclohexyl)ethyl)-1,2,3,4-tetrahydroisoquinoline;
(E)-trans-7-Cyano-2-(2-(1-(4-(3-(6-indolyl)propenoyl)amino)cyclohexyl)ethyl)-1,2,3,4-tetrahydroisoquinoline;
trans-(E)-6-Cyano-2-(2-(1-(4-(3-(3-methylsulfonyl)phenylpropenoyl)amino)cyclohexyl)ethyl-1,2,3,4-tetrahydroisoquinoline;
trans-(E)-2-(2-(1-(4-(3-(3-Acetyl)phenylpropenoyl)amino)cyclohexyl)ethyl)-6-cyano-1,2,3,4-tetrahydroisoquinoline;
trans-7-Cyano-2-(2-(1-(4-(3-(4,6-dimethyl)pyrazolo[1,5-a]pyrimidyl)carboxamido)cyclohexyl)ethyl)-1,2,3,4-tetrahydroisoquinoline;
trans-7-Cyano-2-(2-(1-(4-(2-(5-fluoro)indolyl)carboxamido)cyclohexyl)ethyl)-1,2,3,4-tetrahydroisoquinoline;
trans-7-Cyano-2-(2-(1-(4-(2-(6-cyano)indolyl)carboxamido)cyclohexyl)ethyl)-1,2,3,4-tetrahydroisoquinoline;
trans-7-Cyano-2-(2-(1-(4-(3,4-methylenedioxy)benzamido)cyclohexyl)ethyl)-1,2,3,4-tetrahydroisoquinoline;
trans-7-Cyano-2-(2-(1-(4-(2-indolyl)-N-methylcarboxamido)cyclohexyl)ethyl)-1,2,3,4-tetrahydroisoquinoline;
trans-7-Cyano-2-(2-(1-(4-(2-(1-methyl)indolyl)carboxamido)cyclohexyl)ethyl-1,2,3,4-tetrahydroisoquinoline;
trans-7-Cyano-2-(2-(1-(4-(2-(5-nitro)indolyl)carboxamido)cyclohexyl)ethyl)-1,2,3,4-tetrahydroisoquinoline;
trans-7-Cyano-2-(2-(1-(4-(2-(5-methylsulfonyl)indolyl)carboxamido)cyclohexyl)-ethyl-1,2,3,4-tetrahydroisoquinoline;
trans-7-Cyano-2-(2-(1-(4-(3-isoquinolyl)carboxamido)cyclohexyl)ethyl)-1,2,3,4-tetrahydroisoquinoline;
trans-7-Cyano-2-(2-(1-(4-(2-(5-methoxy)indolyl)carboxamido)cyclohexyl)ethyl)-1,2,3,4-tetrahydroisoquinoline;
trans-7-Cyano-2-(2-(1-(4-(2-(7-nitro)indolyl)carboxamido)cyclohexyl)ethyl-1,2,3,4-tetrahydroisoquinoline;
trans-7-Cyano-2-(2-(1-(4-(2-(5-methyl)indolyl)carboxamido)cyclohexyl)ethyl)-1,2,3,4-tetrahydroisoquinoline;
trans-7-Cyano-2-(2-(1-(4-(2(1H)-pyrrolo[3,2-b]pyridyl)carboxamido)cyclohexyl)ethyl)-1,2,3,4-tetrahydroisoquinoline;
trans-7-Cyano-2-(2-(1-(4-(3-pyrazolyl)carboxamido)cyclohexyl)ethyl)-1,2,3,4-tetrahydroisoquinoline;
trans-7-Cyano-2-(2-(1-(4-(6-(1-methyl)benzimidazolyl)carboxamido)cyclohexyl)ethyl)-1,2,3,4-tetrahydroisoquinoline;
trans-7-Cyano-2-(2-(1-(4-(5-(1,2-dihydro)benzofuranyl)carboxamido)cyclohexyl)ethyl)-1,2,3,4-tetrahydroisoquinoline;
trans-7-Cyano-2-(2-(1-(4-(2-thieno[3,2-b]thiophenyl)carboxamido)cyclohexyl)ethyl-1,2,3,4-tetrahydroisoquinoline;
trans-7-Cyano-2-(2-(1-(4-(4-indolyl)carboxamido)cyclohexyl)ethyl)-1,2,3,4-tetrahydroisoquinoline;
trans-7-Cyano-2-(2-(1-(4-(2-(6-methoxy)indolyl)carboxamido)cyclohexyl)ethyl-1,2,3,4-tetrahydroisoquinoline;

trans-7-Cyano-2-(2-(1-(4-(2-(6-chloro)indolyl)carboxamido)cyclohexyl)ethyl)-1,2,3,4-tetrahydroisoquinoline;

trans-7-Cyano-2-(2-(1-(4-(2-(6-fluoro)indolyl)carboxamido)cyclohexyl)ethyl-1,2,3,4-tetrahydroisoquinoline;

trans-7-Cyano-2-(2-(1-(4-(2-(6-methyl)indolyl)carboxamido)cyclohexyl)ethyl)-1,2,3,4-tetrahydroisoquinoline;

trans-2-(2-(1-(4-(2-(5-Chloro)benzofuranyl)carboxamido)cyclohexyl)ethyl)-7-cyano-1,2,3,4-tetrahydroisoquinoline;

trans-2-(2-(1-(4-(2-(3-Amino)naphthyl)carboxamido)cyclohexyl)ethyl)-7-cyano-1,2,3,4-tetrahydroisoquinoline;

trans-7-Cyano-2-(2-(1-(4-(2-thienyl)carboxamido)cyclohexyl)ethyl)-1,2,3,4-tetrahydroisoquinoline;

trans-7-Cyano-2-(2-(1-(4-(2-naphthyl)carboxamido)cyclohexyl)ethyl)-1,2,3,4-tetrahydroisoquinoline;

trans-7-Cyano-2-(2-(1-(4-(3-indolyl)carboxamido)cyclohexyl)ethyl)-1,2,3,4-tetrahydroisoquinoline;

trans-(E)-7-Cyano-2-(2-(1-(4-(3-phenylpropenoyl)amino)cyclohexyl)ethyl)-1,2,3,4-tetrahydroisoquinoline;

trans-2-(2-(1-(4-(2-Benzo[b]thienyl)carboxamido)cyclohexyl)ethyl)-6-cyano-1,2,3,4-tetrahydroisoquinoline;

trans-6-Cyano-2-(2-(1-(4-(5-indolyl)carboxamido)cyclohexyl)ethyl)-1,2,3,4-tetrahydroisoquinoline;

trans-6-Cyano-2-(2-(1-(4-(6-indolyl)carboxamido)cyclohexyl)ethyl)-1,2,3,4-tetrahydroisoquinoline;

trans-6-Cyano-2-(2-(1-(4-(2-thieno[3,2-b]thiophenyl)carboxamido)cyclohexyl)-ethyl-1,2,3,4-tetrahydroisoquinoline;

trans-6-Cyano-2-(2-(1-(4-(3,4-methylenedioxy)benzamido)cyclohexyl)ethyl)-1,2,3,4-tetrahydroisoquinoline;

trans-2-(2-(1-(4-(2-Benzofuranyl)carboxamido)cyclohexyl)ethyl)-6-cyano-1,2,3,4-tetrahydroisoquinoline;

trans-(E)-6-Cyano-2-(2-(1-(4-(3-(5-(1,2-dihydro-2-oxo)-(3H)indolyl)propenoyl)amino)cyclohexyl)ethyl-1,2,3,4-tetrahydroisoquinoline;

trans-(E)-6-Cyano-2-(2-(1-(4-(3-phenylpropenoyl)amino)cyclohexyl)ethyl)-1,2,3,4-tetrahydroisoquinoline;

trans-(E)-6-Cyano-2-(2-(1-(4-(3-(4-ethylsulfonyl)phenylpropenoyl)amino)cyclohexyl)ethyl)-1,2,3,4-tetrahydroisoquinoline;

trans-(E)-2-(2-(1-(4-(3-(4-Acetyl)phenylpropenoyl)amino)cyclohexyl)ethyl)-6-cyano-1,2,3,4-tetrahydroisoquinoline;

trans-(E)-6-Cyano-2-(2-(1-(4-(3-(3,4-methylenedioxy)phenylpropenoyl)amino)cyclohexyl)ethyl)-1,2,3,4-tetrahydroisoquinoline;

trans-(E)-6-Cyano-2-(2-(1-(4-(3-(3-thienyl)propenoyl)amino)cyclohexyl)ethyl)-1,2,3,4-tetrahydroisoquinoline;

trans-(E)-6-Cyano-2-(2-(1-(4-(3-(2-thienyl)propenoyl)amino)cyclohexyl)ethyl)-1,2,3,4-tetrahydroisoquinoline;

trans-(E)-2-(2-(1-(4-(3-(2-Acetyl)phenylpropenoyl)amino)cyclohexyl)ethyl)-6-cyano-1,2,3,4-tetrahydroisoquinoline;

trans-(E)-2-(2-(1-(4-(3-(4-Acetyl)phenylpropenoyl)amino)cyclohexyl)ethyl)-6-cyano-1,2,3,4-tetrahydroisoquinoline;

trans-(E)-6-Cyano-2-(2-(1-(4-(3-(4-methoxy)phenylpropenoyl)amino)cyclohexyl)ethyl)-1,2,3,4-tetrahydroisoquinoline;

trans-(E)-2-(2-(1-(4-(3-(4-Chloro)phenylpropenoyl)amino)cyclohexyl)ethyl)-6-cyano-1,2,3,4-tetrahydroisoquinoline;

trans-(E)-6-Cyano-2-(2-(1-(4-(3-(3-methylaminocarbonyl)phenylpropenoyl)amino)cyclohexyl)ethyl)-1,2,3,4-tetrahydroisoquinoline;

trans-(E)-6-Cyano-2-(2-(1-(4-(3-(4-methylaminocarbonyl)phenylpropenoyl)amino)cyclohexyl)ethyl)-1,2,3,4-tetrahydroisoquinoline;

trans-7-Cyano-2-(2-(1-(4-(6-indolyl)carboxamido)cyclohexyl)ethyl)-1,2,3,4-tetrahydroisoquinoline;

trans-2-(2-(1-(4-(2-(5-Chloro)indolyl)carboxamido)cyclohexyl)ethyl)-7-cyano-1,2,3,4-tetrahydroisoquinoline;

trans-7-Cyano-2-(2-(1-(4-(3-thienyl)carboxamido)cyclohexyl)ethyl)-1,2,3,4-tetrahydroisoquinoline;

trans-2-(2-(1-(4-(2-(3-Chloro)benzo[b]thienyl)carboxamido)cyclohexyl)ethyl)-7-cyano-1,2,3,4-tetrahydroisoquinoline;

trans-7-Cyano-2-(2-(1-(4-(6-quinolinyl)carboxamido)cyclohexyl)ethyl)-1,2,3,4-tetrahydroisoquinoline;

trans-(E)-7-Cyano-2-(2-(1-(4-(3-(2-(3,4-dimethyl)thieno[2,3-b]thiophenyl)propenoyl)amino)cyclohexyl)ethyl)-1,2,3,4-tetrahydroisoquinoline;

trans-(E)-7-Cyano-2-(2-(1-(4-(3-(3-methylaminocarbonyl)phenylpropenoyl)amino)cyclohexyl)ethyl-1,2,3,4-tetrahydroisoquinoline;

trans-(E)-7-Cyano-2-(2-(1-(4-(3-(3-methoxy)phenylpropenoyl)amino)cyclohexyl)ethyl)-1,2,3,4-tetrahydroisoquinoline;

trans-(E)-2-(2-(1-(4-(3-(3-Acetyl)phenylpropenoyl)amino)cyclohexyl)ethyl)-7-cyano-1,2,3,4-tetrahydroisoquinoline;

trans-(E)-2-(2-(1-(4-(3-(3-Chloro)phenylpropenoyl)amino)cyclohexyl)ethyl)-7-cyano-1,2,3,4-tetrahydroisoquinoline;

trans-(E)-7-Cyano-2-(2-(1-(4-(3-(3-thienyl)propenoyl)amino)cyclohexyl)ethyl)-1,2,3,4-tetrahydroisoquinoline;

trans-(E)-2-(2-(1-(4-(3-(2-Acetamido)phenylpropenoyl)amino)cyclohexyl)ethyl)-7-cyano-1,2,3,4-tetrahydroisoquinoline;

trans-2-(2-(1-(4-Benzamido)cyclohexyl)ethyl)-7-cyano-1,2,3,4-tetrahydroisoquinoline;

trans-(E)-7-Cyano-2-(2-(1-(4-(3-(2-naphthyl)propenoyl)amino)cyclohexyl)eyhyl)-1,2,3,4-tetrahydroisoquinoline;

trans-6-Cyano-2-(2-(1-(4-(2-indolyl)carboxamido)cyclohexyl)ethyl)-1,2,3,4-tetrahydroisoquinoline;

trans-(E)-7-Cyano-2-(2-(1-(4-(3-(2-thienyl)propenoyl)amino)cyclohexyl)ethyl)-1,2,3,4-tetrahydroisoquinoline;

trans-2-(2-(1-(4-(2-Benzo[b]thienyl)carboxamido)cyclohexyl)ethyl)-7-cyano-1,2,3,4-tetrahydroisoquinoline;

trans-7-Cyano-2-(2-(1-(4-(6-(pyrrolo[3,2-c]pyridyl)carboxamido)cyclohexyl)eyhyl)-1,2,3,4-tetrahydroisoquinoline;

trans-(E)-2-(2-(1-(4-(3-(4-Chloro)phenylpropenoyl)amino)cyclohexyl)ethyl)-7-cyano-1,2,3,4-tetrahydroisoquinoline;

trans-(E)-7-Cyano-2-(2-(1-(4-(3-(3,4-methylenedioxy)phenylpropenoyl)amino)cyclohexyl)ethyl)-1,2,3,4-tetrahydroisoquinoline;

trans-(E)-7-Cyano-2-(2-(1-(4-(3-(5-(1,2-dihydro-2-oxo)-(3H)-indolyl)propenoyl)amino)cyclohexyl)ethyl)-1,2,3,4-tetrahydroisoquinoline;

trans-(E)-2-(2-(1-(4-(3-(3-Acetamido)phenylpropenoyl)amino)cyclohexyl)ethyl)-7-cyano-1,2,3,4-tetrahydroisoquinoline;

trans-2-(2-(1-(4-(2-Benzo[b]furanyl)carboxamido)cyclohexyl)ethyl)-7-cyano-1,2,3,4-tetrahydroisoquinoline;

trans-(E)-2-(2-(1-(4-(3-(4-Acetyl)phenylpropenoyl)amino)cyclohexyl)ethyl)-7-cyano-1,2,3,4-tetrahydroisoquinoline;

trans-(E)-7-Cyano-2-(2-(1-(4-(3-(4-methylsulfonyl)phenylpropenoyl)amino)cyclohexyl)ethyl)-1,2,3,4-tetrahydroisoquinoline;

trans-(E)-7-Cyano-2-(2-(1-(4-(3-(4-methoxy)phenylpropenoyl)amino)cyclohexyl)ethyl)-1,2,3,4-tetrahydroisoquinoline;

trans-(E)-7-Cyano-2-(2-(1-(4-(3-(4-methylaminocarbonyl)phenylpropenoyl)amino)cyclohexyl)ethyl)-1,2,3,4-tetrahydroisoquinoline;

trans-7-Cyano-2-(2-(1-(4-(3-quinolinyl)carboxamido)cyclohexyl)ethyl)-1,2,3,4-tetrahydroisoquinoline;

trans-2-(2-(1-(4-(5-Benzimidazolyl)carboxamido)cyclohexyl)ethyl)-7-cyano-1,2,3,4-tetrahydroisoquinoline;

trans-7-Cyano-2-(2-(1-(4-(2-(3-methyl)indolyl)carboxamido)cyclohexyl)ethyl)-1,2,3,4-tetrahydroisoquinoline;

trans-7-Cyano-2-(2-(1-(4-(5-(2-methyl)benzimidazolyl)carboxamido)cyclohexyl)ethyl)-1,2,3,4-tetrahydroisoquinoline;

trans-6-Cyano-2-(2-(1-(4-(5-(2-methyl)benzimidazolyl)carboxamido)cyclohexyl)ethyl)-1,2,3,4-tetrahydroisoquinoline;

trans-2-(2-(1-(4-(2-(5-Acetyl)indolyl)carboxamido)cyclohexyl)ethyl)-7-cyano-1,2,3,4-tetrahydroisoquinoline;

trans-2-(2-(1-(4-(2-(6-Acetyl)indolyl)carboxamido)cyclohexyl)ethyl)-7-cyano-1,2,3,4-tetrahydroisoquinoline;

trans-2-(2-(1-(4-(2-(6-Acetyl)indolyl)carboxamido)cyclohexyl)ethyl-6-cyano-1,2,3,4-tetrahydroisoquinoline;

trans-7-Cyano-2-(2-(1-(4-(2-(6-methylsulfonyl)indolyl)carboxamido)cyclohexyl)ethyl-1,2,3,4-tetrahydroisoquinoline;

trans-7-Cyano-2-(2-(1-(4-(5-(1,2-dihydro-2-oxo)-(3H)-indolyl)carboxamido)cyclohexyl)ethyl)-1,2,3,4-tetrahydroisoquinoline;

trans-6-Cyano-2-(2-(1-(4-(5-(1,2-dihydro-2-oxo)-(3H)-indolyl)carboxamido)cyclohexyl)ethyl)-1,2,3,4-tetrahydroisoquinoline;

trans-6-Cyano-2-(2-(1-(4-(2-(4-methylthio)indolyl)carboxamido)cyclohexyl)eyhyl)-1,2,3,4-tetrahydroisoquinoline;

trans-6-Cyano-2-(2-(1-(4-(2-(5-methoxy)indolyl)carboxamido)cyclohexyl)ethyl)-1,2,3,4-tetrahydroisoquinoline;

trans-6-Cyano-2-(2-(1-(4-(2-(5-methylsulfonyl)indolyl)carboxamido)cyclohexyl)ethyl)-1,2,3,4-tetrahydroisoquinoline;

trans-(E)-6-Cyano-2-(2-(1-(4-(3-(2-indolyl)propenoyl)amino)cyclohexyl)ethyl)-1,2,3,4-tetrahydroisoquinoline;

trans-(E)-7-Cyano-2-(2-(1-(4-(3-(2-indolyl)propenoyl)amino)cyclohexyl)ethyl)-1,2,3,4-tetrahydroisoquinoline;

trans-(E)-7-Cyano-2-(2-(1-(4-(3-(3-indolyl)propenoyl)amino)cyclohexyl)ethyl)-1,2,3,4-tetrahydroisoquinoline;

trans-2-(2-(1-(4-(2-(7-Acetyl)indolyl)carboxamido)cyclohexyl)ethyl)-7-cyano-1,2,3,4-tetrahydroisoquinoline;

trans-7-Cyano-2-(2-1-(4-(3-pyridyl)carboxamido)cyclohexyl)ethyl)-1,2,3,4-tetrahydroisoquinoline;

trans-6-Cyano-2-(2-(1-(4-(2-(6-fluoro)indolyl)carboxamido)cyclohexyl)ethyl)-1,2,3,4-tetrahydroisoquinoline;

trans-6-Cyano-2-(2-(1-(4-(2-(6-methoxy)indolyl)carboxamido)cyclohexyl)ethyl)-1,2,3,4-tetrahydroisoquinoline;

trans-6-Cyano-2-(2-(1-(4-(2-(6-methyl)indolyl)carboxamido)cyclohexyl)ethyl)-1,2,3,4-tetrahydroisoquinoline;

trans-2-(2-(1-(4-(2-(7-Acetyl)indolyl)carboxamido)cyclohexyl)ethyl)-6-cyano-1,2,3,4-tetrahydroisoquinoline;

trans-7-Cyano-2-(2-(1-(4-(2-(5-cyano)indolyl)carboxamido)cyclohexyl)ethyl)-1,2,3,4-tetrahydroisoquinoline;

trans-6-Cyano-2-(2-(1-(4-(2-(5-cyano)indolyl)carboxamido)cyclohexyl)ethyl)-1,2,3,4-tetrahydroisoquinoline;

trans-7-Cyano-2-(2-(1-(4-(2-(7-cyano)indolyl)carboxamido)cyclohexyl)ethyl)-1,2,3,4-tetrahydroisoquinoline;

trans-6-Cyano-2-(2-(1-(4-(2-(7-cyano)indolyl)carboxamido)cyclohexyl)ethyl)-1,2,3,4-tetrahydroisoquinoline;

trans-5-Cyano-2-(2-(1-(4-(2-indolyl)carboxamido)cyclohexyl)ethyl)-1,2,3,4-tetrahydroisoquinoline;

trans-(E)-5-Cyano-2-(2-(1-(4-(3-phenylpropenoyl)amino)cyclohexyl)ethyl)-1,2,3,4-tetrahydroisoquinoline;

trans-7-Cyano-2-(2-(1-(4-(2-(4-methylsulfonyl)indolyl)carboxamido)cyclohexyl)ethyl)-1,2,3,4-tetrahydroisoquinoline;

(±)-trans-7-Cyano-2-(2-(1-(4-(2-(4-methylsulfinyl)indolyl)carboxamido)cyclohexyl)ethyl)-1,2,3,4-tetrahydroisoquinoline;

trans-7-Cyano-2-(2-(1-(4-(4-pyridyl)carboxamido)cyclohexyl)ethyl)-1,2,3,4-tetrahydroisoquinoline;

trans-7-Cyano-2-(2-(1-(4-(4-quinolinyl)carboxamido)cyclohexyl)ethyl)-1,2,3,4-tetrahydroisoquinoline;

trans-6-Cyano-2-(2-(1-(4-(4-quinolinyl)carboxamido)cyclohexyl)ethyl)-1,2,3,4-tetrahydroisoquinoline;

trans-(E)-6-Cyano-2-(2-(1-(4-(3-(2-fluoro)phenylpropenoyl)amino)cyclohexyl)ethyl)-1,2,3,4-tetrahydroisoquinoline;

trans-(E)-6-Cyano-2-(2-(1-(4-(3-(2-methoxy)phenylpropenoyl)amino)cyclohexyl)ethyl)-1,2,3,4-tetrahydroisoquinoline;

trans-(E)-2-(2-(1-(4-(3-(2-Chloro)phenylpropenoyl)amino)cyclohexyl)ethyl)-6-cyano-1,2,3,4-tetrahydroisoquinoline;

trans-(E)-6-Cyano-2-(2-(1-(4-(3-(2-methyl)phenylpropenoyl)amino)cyclohexyl)ethyl)-1,2,3,4-tetrahydroisoquinoline;

trans-(E)-6-Cyano-2-(2-(1-(4-(3-(3-fluoro)phenylpropenoyl)amino)cyclohexyl)ethyl)-1,2,3,4-tetrahydroisoquinoline;

trans-(E)-6-Cyano-2-(2-(1-(4-(3-(2,6-difluoro)phenylpropenoyl)amino)cyclohexyl)ethyl)-1,2,3,4-tetrahydroisoquinoline;

trans-(E)-6-Cyano-2-(2-(1-(4-(3-(2,3-methylenedioxy)phenylpropenoyl)amino)cyclohexyl)ethyl)-1,2,3,4-tetrahydroisoquinoline;

trans-(E)-6-Cyano-2-(2-(1-(4-(3-(2,3-difluoro)phenylpropenoyl)amino)cyclohexyl)ethyl)-1,2,3,4-tetrahydroisoquinoline;

trans-2-(2-(1-(4-(4-Quinolinyl)carboxamido)cyclohexyl)ethyl)-6-trifluoromethyl-1,2,3,4-tetrahydroisoquinoline;

trans-2-(2-(1-(4-(4-Quinolinyl)carboxamido)cyclohexyl)ethyl)-6-trifluoromethoxy)-1,2,3,4-tetrahydroisoquinoline;

trans-(E)-6-Cyano-2-(2-(1-(4-(3-(3-methylsulfonyloxy)phenylpropenoyl)amino)cyclohexyl)ethyl)-1,2,3,4-tetrahydroisoquinoline;

trans-(E)-2-(2-(1-(4-(3-(7-Benzo[b]furanyl)propenoyl)amino)cyclohexyl)ethyl)-6-cyano-1,2,3,4-tetrahydroisoquinoline;

trans-6-Cyano-2-(2-(1-(4-(4-(6-methoxy)quinolinyl)carboxamido)cyclohexyl)ethyl)-1,2,3,4-tetrahydroisoquinoline;

trans-(E)-6-Cyano-2-(2-(1-(4-(3-(1-naphthyl)propenoyl)amino)cyclohexyl)ethyl)-1,2,3,4-tetrahydroisoqinoline;

trans-2-(2-(1-(4-(4-Quinolinyl)carboxamido)cyclohexyl)ethyl)-5-trifluoromethyl-1,2,3,4-tetrahydroisoquinoline;

trans-(E)-2-(2-(1-(4-(3-(3-Cyano)phenylpropenoyl)amino)cyclohexyl)ethyl)-5-trifluoromethyl-1,2,3,4-tetrahydroisoquinoline;

trans-(E)-2-(2-(1-(4-(3-Phenylpropenoyl)amino)cyclohexyl)ethyl)-5-trifluoromethyl-1,2,3,4-tetrahydroisoquinoline;

trans-(E)-2-(2-(1-(4-(3-(3-Acetamido)phenylpropenoyl)amino)cyclohexyl)ethyl)-5-trifluoromethyl-1,2,3,4-tetrahydrosioquinoline;

trans-(E)-6-Cyano-2-(2-(1-(4-(3-(4-quinolinyl)propenoyl)amino)cyclohexyl)ethyl)-1,2,3,4-tetrahydroisoquinoline;

trans-5,6-Difluoro-2-(2-(1-(4-(4-quinolinyl)carboxamido)cyclohexyl)ethyl-1,2,3,4-tetrahydroisoquinoline;

trans-(E)-5,6-Difluoro-2-(2-(1-(4-(3-phenylpropenoyl)amino)cyclohexyl)ethyl)-1,2,3,4-tetrahydroisoquinoline;

trans-(E)-5,6-Difluoro-2-(2-(1-(4-(3-(3-methylsulfonamido)phenylpropenoyl)amino)cyclohexyl)ethyl)-1,2,3,4-tetrahydroisoquinoline;

trans-(E)-6-Cyano-2-(2-(1-(4-(3-(1-(4-fluoro)naphthyl)propenoyl)amino)cyclohexyl)ethyl)-1,2,3,4-tetrahydroisoquinoline;

trans-(E)-2-(2-(1-(4-(3-(4-Benzo[b]furanyl)propenoyl)amino)cyclohexyl)ethyl)-6-cyano-1,2,3,4-tetrahydroisoquinoline;

trans-(E)-2-(2-(1-(4-(3-(2-Cyano)phenylpropenoyl)amino)cyclohexyl)ethyl)-5-trifluoromethyl-1,2,3,4-tetrahydroisoquinoline;

trans-(E)-2-(2-(1-(4-(3-(4-Cyano)phenylpropenoyl)amino)cyclohexyl)ethyl)-5-trifluoromethyl-1,2,3,4-tetrahydroisoquinoline;

trans-6-Pentafluoroethyl-2-(2-(1-(4-(4-quinolinyl)carboxamido)cyclohexyl)ethyl)-1,2,3,4-tetrahydroisoquinoline;

trans-6-Cyano-2-(2-(1-(4-(4-(6-fluoro)quinolinyl)carboxamido)cyclohexyl)ethyl)-1,2,3,4-tetrahydroisoquinoline;

trans-6-Cyano-2-(2-(1-(4-(1-isoquinolinyl)carboxamido)cyclohexyl)ethyl)-1,2,3,4-tetrahydroisoquinoline;

trans-(E)-2-(2-(1-(4-(3-(3-Acetamido)phenylpropenoyl)amino)cyclohexyl)eyhyl)-5-pentafluoroethyl-1,2,3,4-tetrahydroisoquinoline;

trans-6-Cyano-2-(2-(1-(4-(4-(3-fluoro)quinolinyl)carboxamido)cyclohexyl)ethyl)-1,2,3,4-tetrahydroisoquinoline;

trans-6-Cyano-2-(2-(1-(4-(5-isoquinolinyl)carboxamido)cyclohexyl)ethyl)-1,2,3,4-tetrahydroisoquinoline;

trans-6-Cyano-2-(2-(1-(4-(4-(7-fluoro)quinolinyl)carboxamido)cyclohexyl)eyhyl)-1,2,3,4-tetrahydroisoquinoline;

trans-6-Cyano-2-(2-(1-(4-(5-(I,2-dihydro-2-oxo)quinolinyl)carboxamido)cyclohexyl)ethyl)-1,2,3,4-tetrahydroisoquinoline;

trans-6-Cyano-2-(2-(1-(4-(5-(2,3-dihydro-3-oxo)-4H-benzoxazinyl)-carboxamido)cyclohexyl)ethyl)-1,2,3,4-tetrahydroisoquinoline;

trans-(E)-8-Cyano-2-(2-(1-(4-(3-phenylpropenoyl)amino)cyclohexyl)ethyl)-1,2,3,4-tetrahydroisoquinoline;

trans-8-Cyano-2-(2-(1-(4-(2-indolyl)carboxamido)cyclohexyl)ethyl)-1,2,3,4-tetrahydroisoquinoline;

trans-7-Cyano-2-(2-(1-(4-(2-indolyl)carboxamido)cyclohexyl)ethyl)-6-methyl-1,2,3,4-tetrahydroisoquinoline;

trans-6-Cyano-2-(2-(1-(4-(2-naphthyl)carboxamido)cyclohexyl)ethyl)-1,2,3,4-tetrahydroisoquinoline;

trans-(E)-7-Cyano-6-methyl-2-(2-(1-(4-(3-phenylpropenoyl)amino)cyclohexyl)ethyl)-1,2,3,4-tetrahydroisoquinoline;

trans-2-(2-(1-(4-(4-(4-Acetyl)phenyl)benzoyl)aminocyclohexyl)ethyl)-5-cyano-1,2,3,4-tetrahydroisoquinoline;

trans-(E)-2-(2-(1-(4-(3-(3-Acetamido)phenylpropenoyl)amino)cyclohexyl)ethyl)-6-cyano-1,2,3,4-tetrahydroisoquinoline;

trans-(E)-6-Cyano-2-(2-(1-(4-(3-(3-methoxy)phenylpropenoyl)amino)cyclohexyl)eyhyl)-1,2,3,4-tetrahydroisoquinoline;

trans-(E)-2-(2-(1-(4-(3-(3-Chloro)phenylpropenoyl)amino)cyclohexyl)ethyl)-6-cyano-1,2,3,4-tetrahydroisoquinoline;

trans-2-(2-(1-(4-(4-Cinnolinyl)carboxamido)cyclohexyl)ethyl)-7-cyano-1,2,3,4-tetrahydroisoquinoline;

trans-(E)-6-Cyano-2-(2-(1-(4-(3-(4-fluoro)phenylpropenoyl)amino)cyclohexyl)ethyl)-1,2,3,4-tetrahydroisoquinoline;

trans-(E)-6-Cyano-2-(2-(1-(4-(3-(2,5-difluoro)
phenylpropenoyl)amino)cyclohexyl)eyhyl)-1,2,3,4-
tetrahydroisoquinoline;

trans-6-Cyano-2-(2-(1-(4-(5-quinolinyl)carboxamido)
cyclohexyl)ethyl)-1,2,3,4-tetrahydroisoquinoline;

trans-(E)-6-Bromo-2-(2-(1-(4-(3-(3-methylsulfonyl)
phenylpropenoyl)amino)cyclohexyl)ethyl)-1,2,3,4-
tetrahydroisoquinoline;

trans-(E)-2-(2-(1-(4-(3-(3-Methylsulfonyl)
phenylpropenoyl)amino)cyclohexyl)ethyl)-6-
trifluoromethyl-1,2,3,4-tetrahydroisoquinoline;

trans-(E)-2-(2-(1-(4-(3-(3-Methylsulfonyl)
phenylpropenoyl)amino)cyclohexyl)ethyl)-6-
trifluoromethoxy-1,2,3,4-tetrahydroisoquinoline;

trans-(E)-6-Cyano-2-(2-(1-(4-(3-(2,4-difluoro)
phenylpropenoyl)amino)cyclohexyl)ethyl)-1,2,3,4-
tetrahydroisoquinoline;

trans-2-(2-(1-(4-(3-Benzo[b]furanyl)carboxamido)
cyclohexyl)ethyl)-6-cyano-1,2,3,4-
tetrahydroisoquinoline;

trans-6-Cyano-2-(2-(1-(4-(7-indolyl)carboxamido)
cyclohexyl)ethyl)-1,2,3,4-tetrahydroisoquinoline;

trans-6-Cyano-2-(2-(1-(4-(4-(8-fluoro)quinolinyl)
carboxamido)cyclohexyl)ethyl)-1,2,3,4-
tetrahydroisoquinoline;

trans-6-Cyano-2-(2-(1-(4-(4-(8-bromo)quinolinyl)
carboxamido)cyclohexyl)ethyl)-1,2,3,4-
tetrahydroisoquinoline;

trans-6-Cyano-2-(2-(1-(4-(4-(8-cyano)quinolinyl)
carboxamido)cyclohexyl)ethyl)-1,2,3,4-
tetrahydroisoquinoline;

trans-6-Cyano-2-(2-(1-(4-(5-(8-fluoro)quinolinyl)
carboxamido)cyclohexyl)ethyl)-1,2,3,4-
tetrahydroisoquinoline;

trans-6-Cyano-2-(2-(1-(4-(4-(7-cyano)quinolinyl)
carboxamido)cyclohexyl)ethyl)-1,2,3,4-
tetrahydroisoquinoline;

trans-2-(2-(1-(4-(3-(7-Fluoro)benzo[b]furanyl)
carboxamido)cyclohexyl)ethyl)-6-cyano-1,2,3,4-
tetrahydroisoquinoline;

trans-2-(2-(1-(4-(3-(5-Cyano)benzo[b]furanyl)
carboxamido)cyclohexyl)ethyl)-6-cyano-1,2,3,4-
tetrahydroisoquinoline;

trans-6-Cyano-2-(2-(1-(4-(4-(3-methoxy)quinolinyl)
carboxamido)cyclohexyl)ethyl)-1,2,3,4-
tetrahydroisoquinoline;

trans-6-Cyano-2-(2-(1-(4-(5-(8-chloro)quinolinyl)
carboxamido)cyclohexyl)ethyl)-1,2,3,4-
tetrahydroisoquinoline;

trans-6-Cyano-2-(2-(1-(4-(3-pyrrolo[2,3-b]pyridyl)
carboxamido)cyclohexyl)ethyl)-1,2,3,4-
tetrahydroisoquinoline;

trans-2-(2-(4-(3-(7-Cyano)benzofuranyl)carboxamido)
cyclohexyl)ethyl)-6-cyano-1,2,3,4-
tetrahydroisoquinoline;

trans-(E)-2-(2-(1-(4-(3-(3-Acetamido)phenylpropenoyl)
amino)cyclohexyl)ethyl)-6-cyano-1,2,3,4-
tetrahydroisoquinoline;

trans-(E)-6-Cyano-2-(2-(1-(4-(3-(3-methoxy)
phenylpropenoyl)amino)cyclohexyl)eyhyl)-1,2,3,4-
tetrahydroisoquinoline;

trans-(E)-2-(2-(1-(4-(3-(3-Chloro)phenylpropenoyl)
amino)cyclohexyl)ethyl)-6-cyano-1,2,3,4-
tetrahydroisoquinoline;

trans-2-(2-(1-(4-(4-Cinnolinyl)carboxamido)cyclohexyl)
ethyl)-7-cyano-1,2,3,4-tetrahydroisoquinoline;

trans-(E)-6-Cyano-2-(2-(1-(4-(3-(4-fluoro)
phenylpropenoyl)amino)cyclohexyl)ethyl)-1,2,3,4-
tetrahydroisoquinoline;

trans-(E)-6-Cyano-2-(2-(1-(4-(3-(2,5-difluoro)
phenylpropenoyl)amino)cyclohexyl)eyhyl)-1,2,3,4-
tetrahydroisoquinoline;

trans-6-Cyano-2-(2-(1-(4-(5-quinolinyl)carboxamido)
cyclohexyl)ethyl)-1,2,3,4-tetrahydroisoquinoline;

trans-(E)-6-Bromo-2-(2-(1-(4-(3-(3-methylsulfonyl)
phenylpropenoyl)amino)cyclohexyl)ethyl)-1,2,3,4-
tetrahydroisoquinoline;

trans-(E)-2-(2-(1-(4-(3-(3-Methylsulfonyl)
phenylpropenoyl)amino)cyclohexyl)ethyl)-6-
trifluoromethyl-1,2,3,4-tetrahydroisoquinoline;

trans-(E)-2-(2(1-(4-(3-(3-Methylsulfonyl)
phenylpropenoyl)amino)cyclohexyl)ethyl)-6-
trifluoromethoxy-1,2,3,4-tetrahydroisoquinoline;

or a salt thereof.

7. trans-6-Cyano-2-(2-(1-(4-(4-quinolinyl)carboxamido) cyclohexyl)ethyl)-1,2,3,4-tetrahydroisoquinoline or a salt thereof.

8. A salt according to claim 7 which is the mono hydrochloride or monomesylate salt.

9. A pharmaceutical composition comprising a compound of formula (I) as claimed in claim 1 or a physiologically acceptable salt thereof and a physiologically acceptable carrier therefor.

10. A method of treating a condition which requires modulation of a dopamine receptor which comprises administering to a subject in need thereof an effective amount of a compound of formula (I) according to claim 1 or a physiologically acceptable salt thereof.

11. The method of claim 10, wherein the dopamine receptor is a dopamine $D_3$ receptor.

12. The method of claim 10, wherein the compound of formula (I) is a dopamine antagonist.

13. The method of claim 10, wherein the condition is a psychotic condition.

14. The method of claim 10, wherein the condition is schizophrenia.

15. A pharmaceutical composition comprising a compound of formula (I) as claimed in claim 2 or a physiologically acceptable salt thereof and a physiologically acceptable carrier thereof.

16. A pharmaceutical composition comprising a compound of formula (I) as claimed in claim 3 or a physiologically acceptable salt thereof and a physiologically acceptable carrier thereof.

17. A process for preparing a compound of formula (I) which process comprises one of the following processes:

67

(a) reacting a compound of formula(II):

Formula (II)

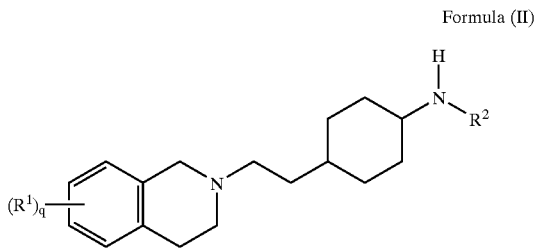

with a compound of formula (III):

A—COX                                 Formula (III)

wherein $R^1$, $R^2$, q, and A are as defined in claim 1, and X is a halogen atom or the residue of an activated ester; or (b) reacting a compound of formula (II) with a compound A—Br, or A—I, or A—$OSO_2CF_3$ in the presence of carbon monoxide and a catalyst, wherein A is as defined in claim 1;

(c) or, wherein $R^1$ is $Ar^3$—Z and Z is a bond, reacting a compound of formula (IV):

Formula (IV)

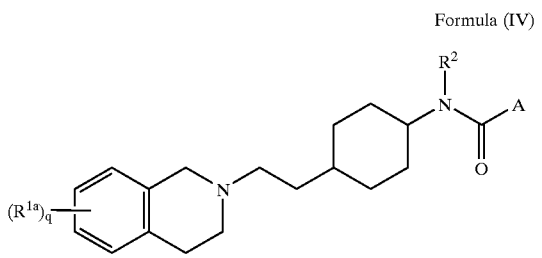

wherein $Ar^3$, A, $R^2$ and q are as defined in claim 1, and one $R^{1a}$ represents a group W wherein W is a halogen atom or a trifluoromethylsulfonyloxy group, or W is a group M selected from a boron derivative or a metal function, and when q is 2 the other $R^{1a}$ is $R^1$, as defined in claim 1;

with a compound $Ar^3$—$W^1$, wherein $W^1$ is a halogen atom or a trifluoromethylsulfonyloxy group when W is a group M selected from a boron derivative or a metal function, or $W^1$ is a group M selected from a boron derivative or a metal function when W is a halogen atom or a trifluoromethylsulfonyloxy group;

(d) or, wherein $R^1$ is $Ar^3$—Z and Z is O or S, reacting a compound of formula (V):

Formula (V)

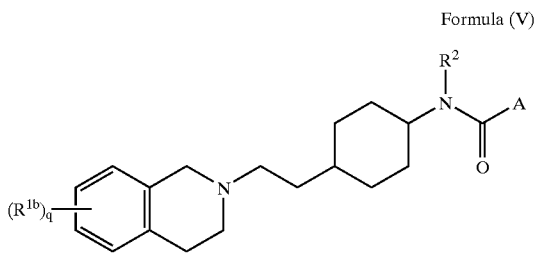

wherein A, $R^2$ and q are as defined in claim 1, and one $R^{1b}$ represents a group ZH and when q is 2 the other $R^{1b}$ represents $R^1$;

with a reagent serving to introduce the group $Ar^3$;

(e) or, wherein A is a group of the formula (b) and Y is a bond, reacting a compound of formula (VI):

68

Formula (VI)

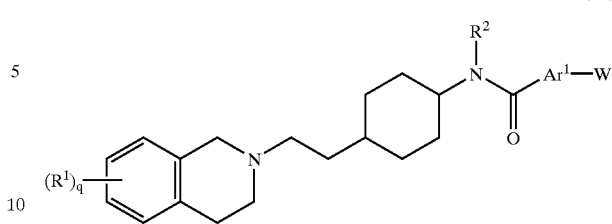

wherein $R^1$, $R^2$, q and $Ar^1$ are as defined in claim 1, with a compound $Ar^2$—$W^1$, wherein $W^1$ is a halogen atom or a trifluoromethylsulfonyloxy group when W is a group M, or $W^1$ is a group M when W is a halogen atom or a trifluoromethylsulfonyloxy group; or (f) interconversion of one compound of formula (I) to a different compound of formula (I) by (i) alkylation of a compound (I) wherein $R^2$ represents hydrogen, (ii) conversion of one $R^1$ from alkoxy to hydroxy, or (iii) conversion of $R^1$ from hydroxy to sulfonyloxy, (iv) conversion of a compound wherein Y represents S to a compound wherein Y is $SO_2$, or (v) conversion of Y from CO to $CH_2$; or (g) separating cis- and trans-isomers of compounds of formula (I) by conventional methods; or (h) separating cis- and trans-isomers of compounds of formula (I) made by any one of processes (a) through (f), by conventional methods;

and optionally thereafter forming a salt of formula (I).

18. The method of claim 10, wherein the condition is drug dependency.

19. The method of claim 18, wherein the compound of formula (I) is trans-6-Cyano-2-(2-(1-(4-(3-pyrrolo[2,3-b]pyridyl)carboxamido)cyclohexyl)ethyl)-1,2,3,4-tetrahydroisoquinoline.

20. A compound of formula (I) which is trans-6-Cyano-2-(2-(1-(4-(3-pyrrolo[2,3-b]pyridyl)carboxamido)cyclohexyl)ethyl)-1,2,3,4-tetrahydroisoquinoline or a salt thereof.

21. A salt according to claim 20 which is the mono hydrochloride or monomesylate salt.

22. A pharmaceutical composition comprising a compound of formula (I) as claimed in claim 20 or a physiologically acceptable salt thereof and a physiologically acceptable carrier thereof.

23. A pharmaceutical composition comprising a compound of formula (I) as claimed in claim 7 or a physiologically acceptable salt thereof and a physiologically acceptable carrier thereof.

24. A compound or salt according to claim 1 wherein A represents a group of formula (a), (b) or (c), and wherein Ar is an optionally substituted phenyl ring or an optionally substituted 5- or 6-membered aromatic heterocyclic ring, or an optionally substituted bicyclic aromatic or heteroaromatic ring system.

25. A compound or salt according to claim 1 wherein A represents a group of formula (a), (b) or (c), and wherein Ar is an optionally substituted phenyl ring or an optionally substituted 5- or 6-membered aromatic heterocyclic ring, or an optionally substituted bicyclic aromatic or heteroaromatic ring system, with the proviso that $R^1$ is not pentafluoroethyl.

26. A compound of formula (I) which is:
trans-2-(2-(1-(4-(4-(4-Acetyl)phenyl)benzoyl)aminocyclohexyl)ethyl)-6-cyano-1,2,3,4-tetrahydroisoquinoline;

trans-6-Cyano-2-(2-(1-(4-(1-naphthyl)carboxamido)cyclohexyl)ethyl)-1,2,3,4-tetrahydroisoquinoline;

trans-(E)-6-Cyano-2-(2-(1-(4-(3-(2-fluoro)phenylpropenoyl)amino)cyclohexyl)ethyl)-1,2,3,4-tetrahydroisoquinoline;

trans-(E)-6-Cyano-2-(2-(1-(4-(3-(2-methoxy)phenylpropenoyl)amino)cyclohexyl)ethyl)-1,2,3,4-tetrahydroisoquinoline;

trans-(E)-2-(2-(1-(4-(3-(2-Chloro)phenylpropenoyl)amino)cyclohexyl)ethyl)-6-cyano-1,2,3,4-tetrahydroisoquinoline;

trans-(E)-6-Cyano-2-(2-(1-(4-(3-(2-methyl)phenylpropenoyl)amino)cyclohexyl)ethyl)-1,2,3,4-tetrahydroisoquinoline;

trans-(E)-6-Cyano-2-(2-(1-(4-(3-(3-fluoro)phenylpropenoyl)amino)cyclohexyl)ethyl)-1,2,3,4-tetrahydroisoquinoline;

trans-(E)-6-Cyano-2-(2-(1-(4-(3-(2,6-difluoro)phenylpropenoyl)amino)cyclohexyl)ethyl)-1,2,3,4-tetrahydroisoquinoline;

trans-(E)-6-Cyano-2-(2-(1-(4-(3-(2,3-methylenedioxy)phenylpropenoyl)amino)cyclohexyl)ethyl)-1,2,3,4-tetrahydroisoquinoline;

trans-(E)-6-Cyano-2-(2-(1-(4-(3-(2,3-difluoro)phenylpropenoyl)amino)cyclohexyl)ethyl)-1,2,3,4-tetrahydroisoquinoline;

trans-2-(2-(1 (4-(4-Quinolinyl)carboxamido)cyclohexyl)ethyl)-6-trifluoromethyl-1,2,3,4-tetrahydroisoquinoline;

trans-2-(2-(1-(4-(4-Quinolinyl)carboxamido)cyclohexyl)ethyl)-6-trifluoromethoxy)-1,2,3,4-tetrahydroisoquinoline;, trans-(E)-6-Cyano-2-(2-(1-(4-(3-(3-methylsulfonyloxy)phenylpropenoyl)amino)cyclohexyl)ethyl)-1,2,3,4-tetrahydroisoquinoline;

trans-(E)-2-(2-(1-(4-(3-(7-Benzo[b]furanyl)propenoyl)amino)cyclohexyl)ethyl)-6-cyano-1,2,3,4-tetrahydroisoquinoline;

trans-6Cyano-2-(2-(1-(4-(4-(6-methoxy)quinolinyl)carboxamido)cyclohexyl)ethyl)-1,2,3,4-tetrahydroisoquinoline;

trans-(E)-6-Cyano-2-(2-(1-(4-(3-(1-naphthyl)propenoyl)amino)cyclohexyl)ethyl-1,2,3,4-tetrahydroisoqinoline;

trans-2-(2-(1-(4-(4-Quinolinyl)carboxamido)cyclohexyl)ethyl)-5-trifluoromethyl-1,2,3,4-tetrahydroisoquinoline;

trans-(E)-2-(2-(1-(4-(3-(3-Cyano)phenylpropenoyl)amino)cyclohexyl)ethyl)-5-trifluoromethyl-1,2,3,4-tetrahydroisoquinoline;

trans-(E)-2-(2-(1-(4-(3-Phenylpropenoyl)amino)cyclohexyl)ethyl)-5-trifluoromethyl-1,2,3,4-tetrahydroisoquinoline;

trans-(E)-2-(2-(1-(4-(3-(3-Acetamido)phenylpropenoyl)amino)cyclohexyl)ethyl)-5-trifluoromethyl-1,2,3,4-tetrahydrosioquinoline;

trans-(E)-6-Cyano-2-(2-(1-(4-(3-(4-quinolinyl)propenoyl)amino)cyclohexyl)ethyl)-1,2,3,4-tetrahydroisoquinoline;

trans-5,6-Difluoro-2-(2-(1-(4-(4-quinolinyl)carboxamido)cyclohexyl)ethyl-1,2,3,4-tetrahydroisoquinoline;

trans-(E)-5,6-Difluoro-2-(2-(1-(4-(3-phenylpropenoyl)amino)cyclohexyl)ethyl)-1,2,3,4-tetrahydroisoquinoline;

trans-(E)-5,6-Difluoro-2-(2-(1-(4-(3-(3-methylsulfonamido)phenylpropenoyl)amino)cyclohexyl)ethyl)-1,2,3,4-tetrahydroisoquinoline;

trans-(E)-6-Cyano-2-(2-(1-(4-(3-(1-(4-fluoro)naphthyl)propenoyl)amino)cyclohexyl)ethyl)-1,2,3,4-tetrahydroisoquinoline;

trans-(E)-2-(2-(1-(4-(3-(4-Benzo[b]furanyl)propenoyl)amino)cyclohexyl)ethyl)-6-cyano-1,2,3,4-tetrahydroisoquinoline;

trans-(E)-2-(2-(1-(4-(3-(2-Cyano)phenylpropenoyl)amino)cyclohexyl)ethyl)-5-trifluoromethyl-1,2,3,4-tetrahydroisoquinoline;

trans-(E)-2-(2-(1-(4-(3-(4-Cyano)phenylpropenoyl)amino)cyclohexyl)ethyl)-5-trifluoromethyl-1,2,3,4-tetrahydroisoquinoline;

trans-6-Pentafluoroethyl-2-(2-(1-(4-(4-quinolinyl)carboxamido)cyclohexyl)ethyl)-1,2,3,4-tetrahydroisoquinoline;

trans-6-Cyano-2-(2-(1-(4-(4-(6-fluoro)quinolinyl)carboxamido)cyclohexyl)ethyl)-1,2,3,4-tetrahydroisoquinoline;

trans-6-Cyano-2-(2-(1-(4-(1-isoquinolinyl)carboxamido)cyclohexyl)ethyl)-1,2,3,4-tetrahydroisoquinoline;

trans-(E)-2-(2-(1-(4-(3-(3-Acetamido)phenylpropenoyl)amino)cyclohexyl)eyhyl)-5-pentafluoroethyl-1,2,3,4-tetrahydroisoquinoline;

trans-6-Cyano-2-(2-(1-(4-(4-(3-fluoro)quinolinyl)carboxamido)cyclohexyl)ethyl)-1,2,3,4-tetrahydroisoquinoline;

trans-6-Cyano-2-(2-(1-(4-(5-isoquinolinyl)carboxamido)cyclohexyl)ethyl)-1,2,3,4-tetrahydroisoquinoline;

trans-6-Cyano-2-(2-(1-(4-(4-(7-fluoro)quinolinyl)carboxamido)cyclohexyl)eyhyl)-1,2,3,4-tetrahydroisoquinoline;:

trans-6-Cyano-2-(2-(1-(4-(5-(1,2-dihydro-2-oxo)quinolinyl)carboxamido)cyclohexyl)ethyl)-1,2,3,4-tetrahydroisoquinoline;

trans-6-Cyano-2-(2-(1-(4-(5-(2,3-dihydro-3-oxo)-4H-benzoxazinyl)-carboxamido)cyclohexyl)ethyl)-1,2,3,4-tetrahydroisoquinoline;

trans-(E)-8-Cyano-2-(2-(1-(4-(3-phenylpropenoyl)amino)cyclohexyl)ethyl)-1,2,3,4-tetrahydroisoquinoline;

trans-8-Cyano-2-(2-(1-(4-(2-indolyl)carboxamido)cyclohexyl)ethyl)-1,2,3,4-tetrahydroisoquinoline;

trans-7-Cyano-2-(2-(1-(4-(2-indolyl)carboxamido)cyclohexyl)ethyl)-6-methyl-1,2,3,4-tetrahydroisoquinoline;

trans-6-Cyano-2-(2-(1-(4-(2-naphthyl)carboxamido)cyclohexyl)ethyl)-1,2,3,4-tetrahydroisoquinoline;

trans -(E)-7-Cyano-6-methyl-2-(2-(1-(4-(3-phenylpropenoyl)amino)cyclohexyl)ethyl)-1,2,3,4-tetrahydroisoquinoline;

trans-2-(2-(1-(4-(4-(4-Acetyl)phenyl)benzoyl)aminocyclohexyl)ethyl)-5-cyano-1,2,3,4-tetrahydroisoquinoline;

trans-(E)-6-Cyano-2-(2-(1-(4-(3-(2,4-difluoro)phenylpropenoyl)amino)cyclohexyl)ethyl)-1,2,3,4-tetrahydroisoquinoline;

trans-2-(2-(1-(4-(3-Benzo[b]furanyl)carboxamido)cyclohexyl)ethyl)-6-cyano-1,2,3,4-tetrahydroisoquinoline;

trans-6-Cyano-2-(2-(1-(4-(7-indolyl)carboxamido)cyclohexyl)ethyl)-1,2,3,4-tetrahydroisoquinoline;

trans-6-Cyano-2-(2-(1-(4-(4-(8-fluoro)quinolinyl)carboxamido)cyclohexyl)ethyl)-1,2,3,4-tetrahydroisoquinoline;

trans-6-Cyano-2-(2-(1-(4-(4-(8-bromo)quinolinyl)carboxamido)cyclohexyl)ethyl)-1,2,3,4-tetrahydroisoquinoline;

trans-6-Cyano-2-(2-(1-(4-(4-(8-cyano)quinolinyl)carboxamido)cyclohexyl)ethyl)-1,2,3,4-tetrahydroisoquinoline;

trans-6-Cyano-2-(2-(1-(4-(5-(8-fluoro)quinolinyl)carboxamido)cyclohexyl)ethyl)-1,2,3,4-tetrahydroisoquinoline;

trans-6-Cyano-2-(2-(1-(4-(4-(7-cyano)quinolinyl)carboxamido)cyclohexyl)ethyl)-1,2,3,4-tetrahydroisoquinoline;

trans-2-(2-(1-(4-(3-(7-Fluoro)benzo[b]furanyl)carboxamido)cyclohexyl)ethyl)-6-cyano-1,2,3,4-tetrahydroisoquinoline;

trans-2-(2-(1-(4-(3-(5-Cyano)benzo[b]furanyl)carboxamido)cyclohexyl)ethyl)-6-cyano-1,2,3,4-tetrahydroisoquinoline;

trans-6-Cyano-2-(2-(1-(4-(4-(3-methoxy)quinolinyl)carboxamido)cyclohexyl)ethyl)-1,2,3,4-tetrahydroisoquinoline;

trans-6-Cyano-2-(2-(1-(4-(5-(8-chloro)quinolinyl)carboxamido)cyclohexyl)ethyl)-1,2,3,4-tetrahydroisoquinoline;

trans-6-Cyano-2-(2-(1-(4-(3-pyrrolo[2,3-b]pyridyl)carboxamido)cyclohexyl)ethyl)-1,2,3,4-tetrahydroisoquinoline;

trans-2-(2-(4-(3-(7-Cyano)benzo[b]furanyl)carboxamido)cyclohexyl)ethyl)-6-cyano-1,2,3,4-tetrahydroisoquinoline;

or a salt thereof.

* * * * *